US007250128B2

(12) United States Patent
Unger et al.

(10) Patent No.: US 7,250,128 B2
(45) Date of Patent: Jul. 31, 2007

(54) METHOD OF FORMING A VIA IN A MICROFABRICATED ELASTOMER STRUCTURE

(75) Inventors: Marc A. Unger, South San Francisco, CA (US); Hou-Pu Chou, Sunnyvale, CA (US); Todd A. Thorsen, Pasadena, CA (US); Axel Scherer, Laguna Beach, CA (US); Stephen R. Quake, San Marino, CA (US); Jian Liu, Pasadena, CA (US); Mark L. Adams, Pasadena, CA (US); Carl L. Hansen, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 330 days.

(21) Appl. No.: 11/111,264

(22) Filed: Apr. 20, 2005

(65) Prior Publication Data

US 2006/0054228 A1 Mar. 16, 2006

Related U.S. Application Data

(60) Division of application No. 09/997,205, filed on Nov. 28, 2001, now Pat. No. 6,929,030, which is a continuation-in-part of application No. 09/826,583, filed on Apr. 6, 2001, now Pat. No. 6,899,137, which is a continuation-in-part of application No. 09/724,784, filed on Nov. 28, 2000, now Pat. No. 7,144,616, which is a continuation-in-part of application No. 09/605,520, filed on Jun. 27, 2000.

(60) Provisional application No. 60/186,856, filed on Mar. 3, 2000, now abandoned, provisional application No. 60/147,199, filed on Aug. 3, 1999, now abandoned, provisional application No. 60/141,503, filed on Jun. 28, 1999, now abandoned.

(51) Int. Cl.
*B29C 39/02* (2006.01)

(52) U.S. Cl. .................. 264/155; 264/238; 264/250; 264/310; 264/319

(58) Field of Classification Search .............. None
See application file for complete search history.

(56) References Cited

U.S. PATENT DOCUMENTS 3,570,515 A 3/1971 Kinner
(Continued)

FOREIGN PATENT DOCUMENTS

EP 0 592 094 A2 4/1994
(Continued)

OTHER PUBLICATIONS

Ahn et al., "Fluid Micropumps Based on Rotary Magnetic Actuators," Proceedings of 1995 IEEE Micro Electro Mechanical Systems Workshop (MEMS '95), held in Amsterdam, Netherlands on Jan. 29-Feb. 2, 1995, pp. 408-412.
(Continued)

*Primary Examiner*—Edmund H. Lee
(74) *Attorney, Agent, or Firm*—Townsend and Townsend and Crew LLP

(57) ABSTRACT

A method of fabricating an elastomeric structure, comprising: forming a first elastomeric layer on top of a first micromachined mold, the first micromachined mold having a first raised protrusion which forms a first recess extending along a bottom surface of the first elastomeric layer; forming a second elastomeric layer on top of a second micromachined mold, the second micromachined mold having a second raised protrusion which forms a second recess extending along a bottom surface of the second elastomeric layer; bonding the bottom surface of the second elastomeric layer onto a top surface of the first elastomeric layer such that a control channel forms in the second recess between the first and second elastomeric layers; and positioning the first elastomeric layer on top of a planar substrate such that a flow channel forms in the first recess between the first elastomeric layer and the planar substrate.

4 Claims, 61 Drawing Sheets

U.S. PATENT DOCUMENTS

| | | | |
|---|---|---|---|
| 3,747,628 | A | 7/1973 | Holster et al. |
| 4,046,159 | A | 9/1977 | Pegourie |
| 4,119,368 | A | 10/1978 | Yamakazi |
| 4,153,855 | A | 5/1979 | Feingold |
| 4,245,673 | A | 1/1981 | Bouteille et al. |
| 4,434,704 | A | 3/1984 | Surjaatmadja |
| 4,848,722 | A | 7/1989 | Webster |
| 4,898,582 | A | 2/1990 | Faste |
| 4,992,312 | A | 2/1991 | Frisch |
| 5,085,562 | A | 2/1992 | Van Lintel |
| 5,088,515 | A | 2/1992 | Kamen |
| 5,096,388 | A | 3/1992 | Weinberg |
| 5,126,115 | A | 6/1992 | Fujita et al. |
| 5,164,558 | A | 11/1992 | Huff et al. |
| 5,171,132 | A | 12/1992 | Miyazaki et al. |
| 5,224,843 | A | 7/1993 | Van Lintel |
| 5,259,737 | A | 11/1993 | Kamisuki et al. |
| 5,265,327 | A | 11/1993 | Faris et al. |
| 5,290,240 | A | 3/1994 | Horres, Jr. |
| 5,336,062 | A | 8/1994 | Richter |
| 5,346,372 | A | 9/1994 | Naruse et al. |
| 5,375,979 | A | 12/1994 | Trah |
| 5,376,252 | A | 12/1994 | Ekstrom et al. |
| 5,400,741 | A | 3/1995 | DeTitta et al. |
| 5,423,287 | A | 6/1995 | Usami et al. |
| 5,529,465 | A | 6/1996 | Zengerle et al. |
| 5,593,130 | A | 1/1997 | Hansson et al. |
| 5,642,015 | A | 6/1997 | Whitehead et al. |
| 5,659,171 | A | 8/1997 | Young et al. |
| 5,660,370 | A | 8/1997 | Webster |
| 5,681,024 | A | 10/1997 | Lisec et al. |
| 5,705,018 | A | 1/1998 | Hartley |
| 5,759,014 | A | 6/1998 | Van Lintel |
| 5,775,371 | A | 7/1998 | Pan et al. |
| 5,788,468 | A | 8/1998 | Dewa et al. |
| 5,836,750 | A | 11/1998 | Cabuz |
| 5,842,787 | A | 12/1998 | Kopf-Sill et al. |
| 5,875,817 | A | 3/1999 | Carter |
| 5,876,187 | A | 3/1999 | Afromowitz |
| 5,932,799 | A | 8/1999 | Moles |
| 5,942,443 | A | 8/1999 | Parce et al. |
| 5,965,237 | A * | 10/1999 | Bruin et al. ............... 428/156 |
| 6,007,309 | A | 12/1999 | Hartley |
| 6,043,080 | A | 3/2000 | Lipshutz et al. |
| 6,123,769 | A | 9/2000 | Sanjoh |
| 6,155,282 | A | 12/2000 | Zachary et al. |
| 6,174,365 | B1 | 1/2001 | Sanjoh |
| 6,296,673 | B1 | 10/2001 | Santarsiero et al. |
| 6,345,502 | B1 | 2/2002 | Tai et al. |
| 6,409,832 | B2 | 6/2002 | Weigl et al. |
| 6,767,706 | B2 | 7/2004 | Quake et al. |
| 6,793,753 | B2 | 9/2004 | Unger et al. |
| 6,899,137 | B2 | 5/2005 | Unger et al. |
| 6,929,030 | B2 | 8/2005 | Unger et al. |
| 2001/0027745 | A1 | 10/2001 | Weigl et al. |
| 2001/0033796 | A1 | 10/2001 | Unger et al. |
| 2002/0029814 | A1 | 3/2002 | Unger et al. |
| 2002/0037499 | A1 | 3/2002 | Quake et al. |
| 2002/0144738 | A1 | 10/2002 | Unger et al. |
| 2003/0019833 | A1 | 1/2003 | Unger et al. |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |
| EP | 0 845 603 A1 | 6/1998 |
| EP | 0 999 055 A2 | 5/2000 |
| GB | 2 155 152 A | 9/1985 |
| GB | 2 308 460 A | 6/1997 |
| JP | 1-283112 * | 11/1989 |
| WO | WO 98/07069 A1 | 2/1998 |
| WO | WO 99/00655 A2 | 1/1999 |
| WO | WO 99/04361 A1 | 1/1999 |
| WO | WO 99/17093 A1 | 4/1999 |
| WO | WO 99/52633 A1 | 10/1999 |
| WO | WO 00/00678 A1 | 1/2000 |
| WO | WO 00/43748 A1 | 7/2000 |
| WO | WO 00/60345 A1 | 10/2000 |
| WO | WO 01/09595 A2 | 2/2001 |
| WO | WO 01/09595 A3 | 2/2001 |

OTHER PUBLICATIONS

Andersson et al. "Consecutive Microcontact Printing—Ligands for Asymmetric Catalysis in Silicon Channel" Sensors&Actuators, B. 3997, 2001, pp. 1-7.

Benard et al., "A Titanium-Nickel Shape-Memory Alloy Actuated Micropump," Proceedings of Transducers '97, 1997 International Conference on Solid-State Sensors and Actuators, held in Chicage, Il., Jun. 16-19, 1997, 1:361-364 (1997).

Brechtel et al.; "Control of the electroosmotic flow by metal-salt-containing buffers", J Chromatography A, 1995, pp. 97-105, vol. 716.

Bryzek et al.; "Micromachines on the March", IEEE Spectrum, 1994, pp. 20-31, vol. 31, No. 5.

Buchaillot et al.; "Silicon nitride thin films Young's modulus determination by an optical non-destructive method", Jpn. J Appl Phys, 1995, pp. L794-L797, vol. 36, No. 2:6B.

Chiu et al.; "Patterned Deposition of Cells and Proteins onto Surfaces by Using Three-Dimensional Microfluidic Systems", Proc. Natl. Acad. Sci., 2000, pp. 2408-2413, vol. 97, No. 6.

Chou et al. "A microfabricated device for sizing and sorting DNA molecules", Applied Physical Sciences, Biophysics, Proc. Natl. Acad. Sci., 1999, pp. 11-13, vol. 96, U.S.A.

Delamarche et al.; "Patterned delivery of immunoglobulins to surfaces using microfluidic networks", Science, 1997, pp. 779-781, vol. 276.

Duffy et al. "Patterning Electroluminescence Materials with Feature Sizes as Small as 5µm Using Elastomeric Membranes as Masks for Dry Lift-Off", Advanced Materials, 1999, pp. 546-552, vol. 11, No. 7.

Duffy et al. "Rapid Prototyping of Microfluidic Switches in Poly(dimethylsiloxane) and Their Actuation by Electro-Osmotic Flow" Journal of Microeng, 1999, pp. 211-217, vol. 9.

Duffy et al. "Rapid Prototyping of Microfluidic Systems in Poly(dimethylsiloxane)", Analytical Chemistry, 1998, pp. 4974-4984, vol. 70, No. 23.

Effenhauser et al.; "Integrated capillary electrophoresis on flexible silicone microdevices: Analysis of DNA restriction fragments and detection of single DNA molecules on microchips", Anal. Chem, 1997, pp. 3451-3457, vol. 69.

Effenhauser et al.; "Integrated chip-based capillary electrophoresis", Electrophoresis, 1997, pp. 2203-2213, vol. 18.

Fahrenberg et al. "A microvalve system fabricated by thermoplastic molding", J Micromech Microeng, 1995, pp. 169-171, vol. 5.

Fu et al.; "A microfabricated fluorescence-activated cell-sorter", Nature Biotechnology, 1999, pp. 1109-1111, vol. 17.

Gass et al., "Integrated flow-regulated silicon micropump," Sensors and Actuators A Physical, 1994, p. 335-338, vol. 43.

Gerlach, T., "Pumping Gases by a Silicon Micro Pump with Dynamic Passive Valves," Proceedings of Transducers '97, 1997 International Conference on Solid-State Sensors and Actuators, held in Chicago, Il., Jun. 16-19, 1997, pp. 357-360, vol. 1.

Goll et al., "Microvalves with bistable buckled polymer diaphragms," J. Micromech. Microeng., 1996, pp. 77-79, vol. 6.

Gravesen et al.; "Microfluids—A Review", Journal Micromech Microeng, 1993, pp. 168-192, vol. 3.

Harrison et al., "Micromachining a Miniaturized Capillary Electrophoresis-Based Chemical Analysis System on a Chip," Science, 1993, pp. 895-897, vol. 261.

Hornbeck et al., "Bistable Deformable Mirror Device," Spatial Light Modulators and Applications 1988 Technical Digest Series, vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples in a Poly(dimethylsiloxane)-Based Microfluidic Device," Anal. Chem., 1999, 71(20):4781-4785.

Ikuta et al., "Three dimensional micro integrated fluid systems (MIFS) fabricated by stereo lithography," IEEE Kyushu Institute of Technology, 1994, pp. 1-6.

Jacobson et al., "High-speed separations on a microchip," Anal. Chem., 1994, 66(7):1114-1118.

Jacobson et al., "Microfluidic Devices for Electrokinetically Driven Parallel and Serial Mixing," Anal. Chem., 1999, 71(20):4455-4459.

Jerman, H., "Electrically-Activated, Normally-Closed Diaphragm Valves," Proceedings of Transducers '91, 1991 International Conference on Solid-State Sensors and Actuators, pp. 1045-1048 (1991).

Jung et al., "Chemical and Physical Interactions at Metal/Self-Assembled Organic Monolayer Interfaces," Critical Reviews in Solid State and Material Sciences, 1994, pp. 2-10, vol. 19, No. 1.

Kane et al., "Finite element analysis nonsmooth contact", *Computer Methods in Applied Mechanics and Engineering*, 180(1-2):1-26 (1999).

Kenis et al. "Microfabrication Inside Capillaries Using Multiphase Laminar Flow Patterning," Science, 1999, 285:83-85.

Kim, Enoch et al., "Micromolding in Capillaries: Applications in Material Science," J. American Chemical Society, 118:5722-5731 (1996).

Kopp et al. "Chemical Amplification: Continuous-Flow PCR on a Chip", Science, 1998, 280:1046-1048.

Kuhn et al. "Silicon Charge Electrode Array for Ink Jet Printing", IEEE Transactions on Electron Devices, 1978, pp. 1257-1260, vol. ED-25, No. 10.

Lin et al. "Free-Space Micromachined Optical Switches for Optical Networking," IEEE J. Selected Topics in Quantum Electronics, 1999, pp. 4-9, vol. 5, No. 1.

Lötters et al. "The mechanical properties of the rubber elastic polymer polydimethylsiloxane for sensor applications," J. Micromech. Microeng., 1997, 7:145-147.

Lucy et al., "Characterization of the Cationic Surfactant Induced Reversal of Electroosmotic Flow in Capillary Electrophoresis," Anal. Chem., 1996, pp. 300-305, vol. 68.

Maluf, N., *An Introduction to Microelectromechanical Systems Engineering*, Dec. 1999, pp. 42-45, Artech House Publishers, Boston London.

Muller et al., "Surface-Micromachined Microoptical Elements and Systems," Proceedings of IEEE, 1998, 86(8):1705-1720.

Oakley and Knight, "Adaptive dynamic relaxation algorithm for non-linear hyperelastic structures", *Computer Methods in Applied Mechanics and Engineering*, 126:67-89 (1995).

Ogden, "Elastic Deformations of Rubberlike Solids", in *Mechanics of Solids*, pp. 499-537 (1982).

Olsson et al., "Simulation Studies of Diffuser and Nozzle Elements for Valve-less Micropumps," Proceedings of Transducers '97, 1997 International Conference on Solid-State Sensors and Actuators, held in Chicago, Il., Jun. 16-19, 1997, 2:1039-1042 (1997).

Pethig & Markx "Applications of dielectrophoresis in biotechnology," Tibtech, 15:426-432 (1997).

Phillips, W.C. and Rayment, I. "A systematic method for aligning double focusing mirrors." Methods in Enzymology, 1985, vol. 114 (Wyckoff, Hirs and Timasheff, eds.), 316-329, Academic Press.

Qin et al., "Photolithography with transparent reflective photomasks," J. Vac.Sci. Technology, 16(1):98-103 (1998).

Qin et al., "Elastomeric Light Valves**", Adv. Mater., 1997, pp. 407-410, vol. 9, No. 5.

Quake S.R. and Scherer A.; "From Micro- to Nanofacrication with Soft Materials", Science, Nov. 24, 2000; pp. 1536-1540, vol. 290, No. 5496.

Rapp. R., "LIGA micropump for gases and liquids," Sensors and Actuators A, 1994, pp. 57-61, vol. 40.

Roylance et al., "A Batch-Fabricated Silicon Accelerometer", IEEE Transactions on Electron Devices, Dec. 1979, pp. 1911-1917, vol. ED-26, No. 12.

Schasfoort et al., "Field-Effect Flow Control for Microfabricated Fluidic Networks," Science, 1999, 286:942-945.

Schueller et al., "Fabrication of glassy carbon microstructures by soft lithography," Sensors and Actuators, 72(2):125-139 (1999).

Shoji et al.; "Smallest Dead Volume Microvalves for Integrated Chemical Analyzing Systems", Proceedings of Transducers '91, 1991, pp. 1052-1055, San Francisco.

Shoji, S., "Fluids for Sensor Systems", Topics in Current Chemistry, 1998, pp. 162-188, vol. 194, Springer Verlag Berlin Heidelberg.

Smits, J.G., "Piezoelectric Micropump with Three Valves Working Peristaltically", Sensors and Actuators, 1990, pp. 203-206, vol. A21-A23.

Sohn et al., "Capacitance cytometry: Measuring biological cells one by one," PNAS, 97(20):10687-10690 (2000).

Tufte et al., "Silicon Diffused-Element Piezoresistive Diaphragms," J. Appl. Phys., Nov. 1962, pp. 3322-3327, vol. 33, No. 11.

Ullmann's Encyclopedia of Industrial Chemistry, Sections 6 to 6.3, Topic: Carbon Black, Sixth Edition, 1999.

Underwood et al., "Dynamic relaxation", in *Computational Methods for Transient Dynamic Analysis*, Belytschko and Hughes, eds., pp. 245-265, Elsevier Science Publishers, Amsterdam (1983).

Unger, Marc A. et al. "Monolithic Microfabricated Valves and Pumps by Multilayer Soft Lithography" Science, Apr. 7, 2000, vol. 288, 113-116.

Van De Pol et al., "Micro Liquid Handling Devices—A Review", Micro Systems Technologies, 1990, pp. 799-805, vol. 90.

Van De Pol, F.C.M. et al. "A Thermo-Pneumatic Actuation Principle for a Microminiature Pump and Other Micromechanical Devices" Sensors and Actuators, May 3, 1989, pp. 139-143, vol. 17, Nos. 1-2.

Vieider et al.; "A Pneumatically Actuated Micro Valve with a Silicon Rubber Membrane for Integration with Fluid Handling Systems", Proceedings of Transducers '95, the 8th International Conference on Solid-State Sensors and Actuators and Eurosensors IX, held in Stockholm, Sweden on Jun. 25-29, 1995, pp. 284-286, Stockholm, Sweden.

Washizu et al., "Molecular Dielectrophoresis of Biopolymers," IEEE Transactions on Industry Applications, 1994, 30(4):835-843.

Wu, S. et al. "MEMS Flow Sensors for Nano-fluidic Applications", Sensors and Actuators A: Physical, 2001, vol. 89, Nos. 1-2, pp. 152-158.

Xia et al., "Complex Optical Surfaces Formed by Replica Molding Against Elastomeric Masters," Science, 1996, 273:347-349.

Xia et al., "Soft Lithography," Angew. Chem. Int. Ed., 1998, 37:551-575.

Xia, et al. "Micromolding in Capillaries: Applications in Material Science" J. American Chemical Society, 1996, pp. 5722-5731; vol. 118.

Xia, Y. et al., "Micromolding of Polymers in Capillaries: Applications in Microfabrication," Chemistry of Materials, 1996, pp. 1558-1567, vol. 8, No. 7.

Yang et al. "A Mems Thermopneumatic Silicone Membrane Valve", Proceedings of IEEE 10th Annual International Workshop on MicroElectro Mechanical Systems, Sensors and Actuators, 1998, A64(1):101-108.

Yang et al., "A MEMS Thermopneumatic silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118.

Yazdi et al. "Micromachined Inertial Sensors," Proceedings of IEEE, 1998, 86(8):1640-1659.

Young et al. "Contoured elastic-membrane microvalves for microfluidic network integration," J. Biomechanical Engineering, 1999, 121:2-6.

Zengerle et al., "A Micro Membrane Pump with Electrostatic Actuation," 1992 IEEE Conf. on Micro Electro Mechanical Systems, held Feb. 4-7, 1992 in Travemude Germany, pp. 19-24.

Zengerle et al., "Performance Simulation of Microminiaturized Membrane Pumps," from 7th International Conference on Solid-State Sensors and Actuators held Jun. 7-10, 1993 in Yokohama Japan, pp. 106-109.

"Biochips," Nature Biotechnology, vol. 18, Supplement 2000, pp. IT43-IT44, 2000.

"Chapter 9: Microfluidic Devices," Micromachined Transducers Sourcebook, pp. 779-882, 1998.

"Electro Microfluidic Dual In-Line Package (EMDIP)," Sandia National Laboratories, 2 pages, no date.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest, vol. 12, pp. 222-227, 1999.

Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Galambos, Paul et al., "Electrical And Fluidic Packaging Of Surface Micromachined Electro-Microfluidic Devices," 8 pages, no date.

Greene, Chana, "Characterizing The Properties Of PDMS," pp. 1-11, Summer 2000.

Guerin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Hicks, Jennifer, "Genetics And Drug Discovery Dominate Microarray Research," R&D Magazine, pp. 28-33, Feb. 1999.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication in Polydimethylsiloxane (PDMS) Elastomer," Journal of Microelectromechanical Systems, vol. 9, No. 1, pp. 76-81, Mar. 2000.

Kagan, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Khoo, Melvin et al., "A Novel Micromachined Magnetic Membrane Microfluid Pump," pp. 1-4, no date.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Monolithic Integrated Microfluidic DNA Amplification And Capillary Electrophoresis Analysis System," Sensors and Actuators B, vol. 63, pp. 138-146, 2000.

Lammerink, T. S. J. et al., "Modular Concept For Fluid Handling Systems," IEEE, pp. 389-394, 1996.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, Sid, "Fundamental Changes Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems In Poly(dimethylsiloxane)," Electrophoresis, vol. 21, pp. 27-40, 2000.

Oleschuk, Richard D. et al., "Analytical Microdevices For Mass Spectrometry," Trends In Analytical Chemistry, vol. 19, No. 6., pp. 379-388, 2000.

Sanjoh, Akira et al., "Spatiotemporal Protein Crystal Growth Studies Using Microfluidic Silicon Devices," Journal of Crystal Growth, vol. 196, pp. 691-702, 1999.

Thompson, L. F. et al., "Introduction To Microlithography," 185th Meeting of the American Chemical Society, Seattle, WA, pp. 2 cover pages, 1-13, Mar. 20-25, 1983.

Van Den Berg, A. et al., "Micro Total Analysis Systems," Proceedings of the μTAS '94 Workshop, University of Twente, The Netherlands, 17 pages, Nov. 21-22, 1994.

Verpoorte, Elisabeth, M. J. et al., "Three-Dimensional Micro Flow Manifolds For Miniaturized Chemical Analysis Systems," J. Micromech. Microeng., vol. 7, pp. 246-256, 1994.

Wilbur, James L. et al., "Lithographic Molding: A Convenient Route To Structures With Sub-Micrometer Dimensions," Adv. Mater., vol. 7, No. 7, pp. 649-652, 1995.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xu, Bing et al., "Making Negative Poisson's Ratio Microstructures By Soft Lithography," Adv. Mater., vol. 11, No. 14, pp. 1186-1189, 1999.

Yang, Xing et al., "A Lower Power MEMS Silicone/Parylene Valve," Solid-State Sensor and Actuator Workshop, Hilton Head Island, South Carolina, 4 pages, Jun. 7-11, 1998.

"Last Chance For Micromachines," The Economist Technology Quarterly, 8 pages, Dec. 7, 2000.

Black, Harvey, "Tiny Technology Promises Tremendous Profits," The Scientist, vol. 15, No. 21, 4 pages, Oct. 29, 2001.

Calkins, Kathryn, "Mycometrix: Rubber Chips," BioCentury, 2 pages, Oct. 16, 2000.

Chou, Hou-Pu et al:, "A Microfabricated Rotary Pump," Biomedical Microdevices, vol. 3, No. 4, pp. 323-330, 2001.

Fitzgerald, Deborah A., "Making Every Nanoliter Count," The Scientist, vol. 15, No. 21, 8 pages, Oct. 29, 2001.

Goa, Jun et al., "Integrated Microfluidic System Enabling Protein Digestion, Peptide Seperation, And Protein Identification," Analytical Chemistry, vol. 73, No. 11, pp. 2648-2655, Jun. 1, 2001.

Hofmann, Oliver et al., "Modular Approach To Fabrication Of Three-Dimensional Microchannel Systems in PDMS—Application To Sheath Flow Microchips," Lab on a Chip, vol. 1, pp. 108-114, 2001.

Horn, Howard, "Lab Chips Sector: Microtechnologies Are Changing Healthcare And More," Life Sciences, pp. 19-21, Mar. 20, 2001.

Lagally, Eric T. et al., "Fully Integrated PCR-Capillary Electrophoresis Microsystem For DNA Analysis," Lab On A Chip, vol. 1, pp. 102-107, 2001.

Lagally, E. T. et al., "Single-Molecule DNA Amplification And Analysis In An Integrated Microfluidic Device," Analytical Chemistry, vol. 73, pp. 565-570, Feb. 1, 2001.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Van Der Woerd, Mark et al., "Lab-On-A-Chip Based Protein Crystallization," National Aeronautics and Space Administration and Caliper, pp. 1-27, Oct. 25, 2001.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

* cited by examiner

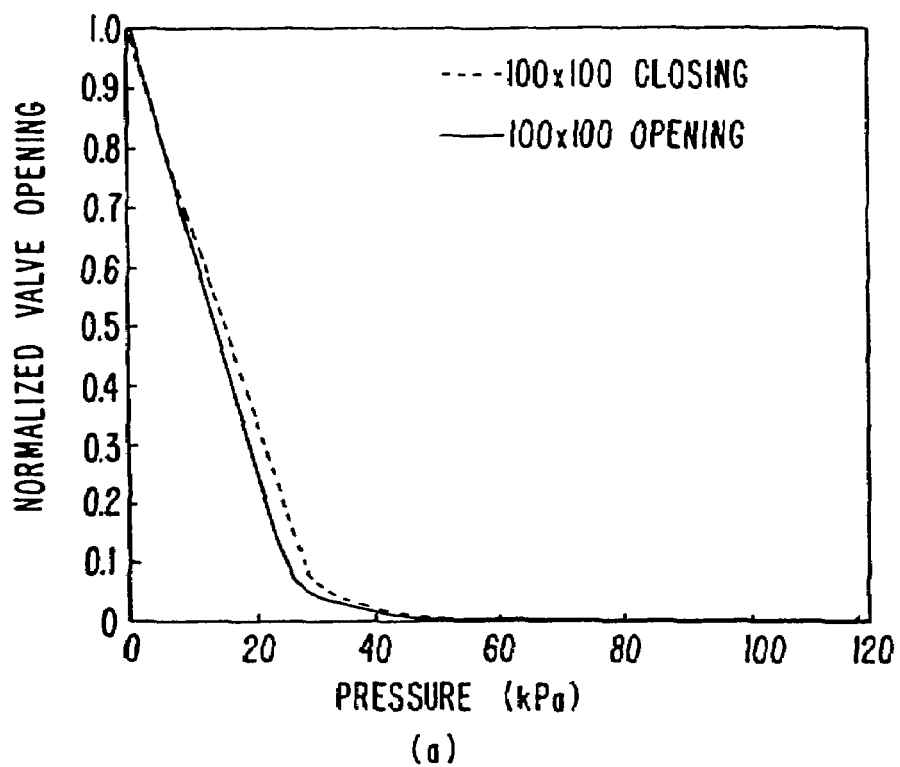
(a)
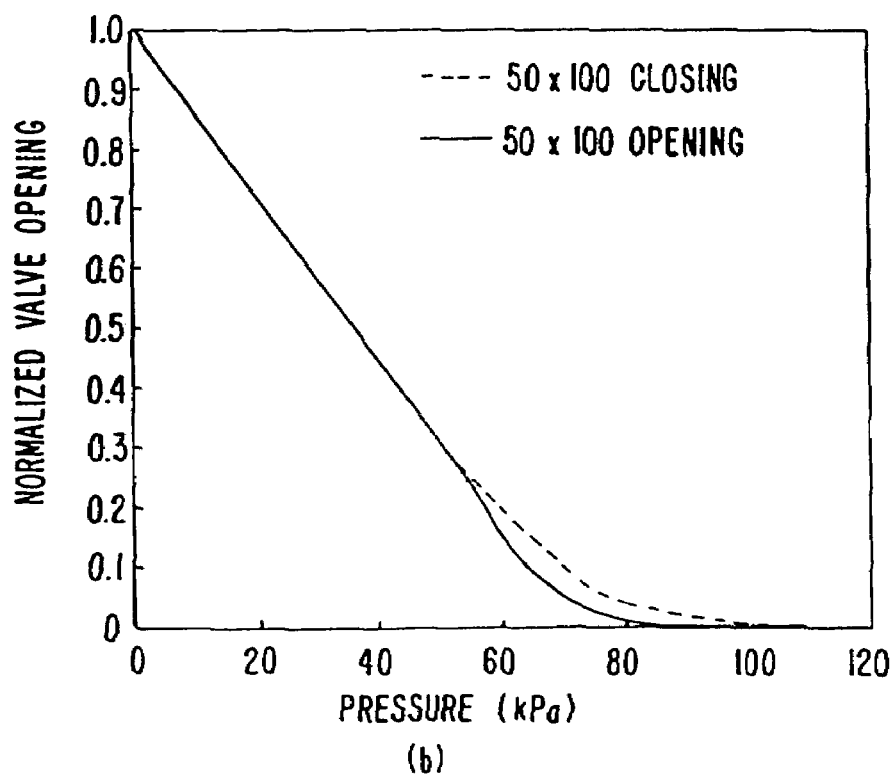
(b)
FIG. 21.

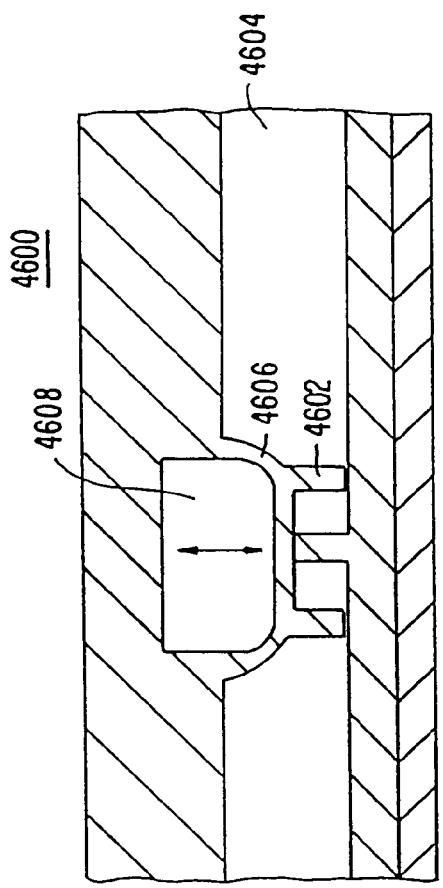
FIG. 46A.
FIG. 46B.
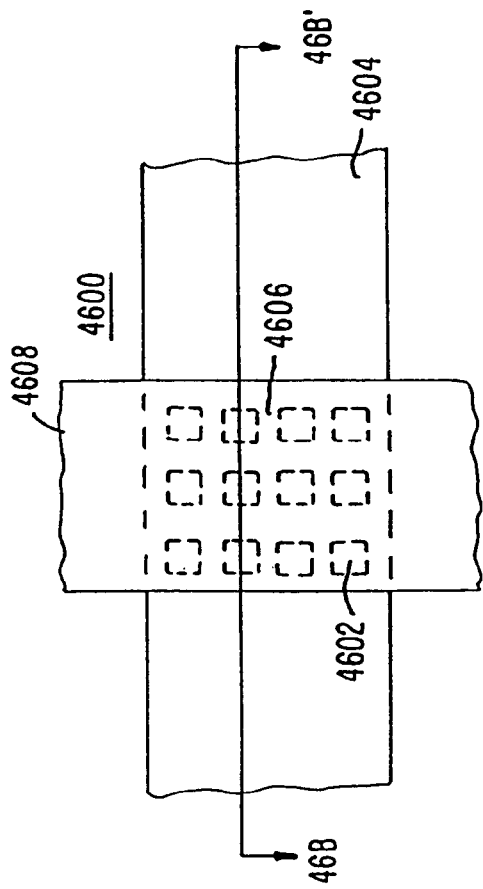
FIG. 45A.
FIG. 45B.

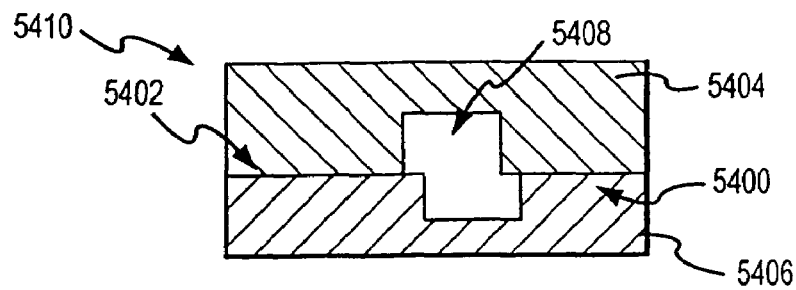
FIG.50
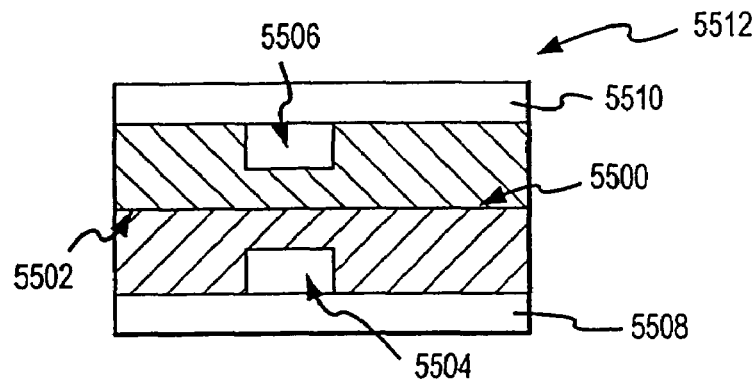
FIG.51
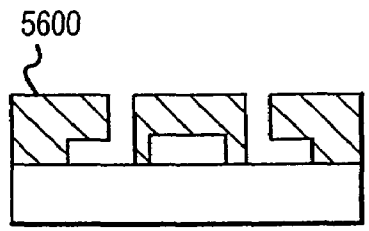
FIG.52A
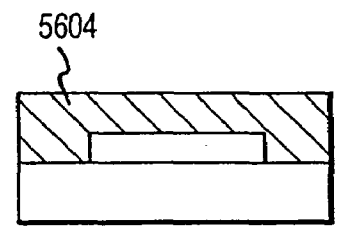
FIG.52B
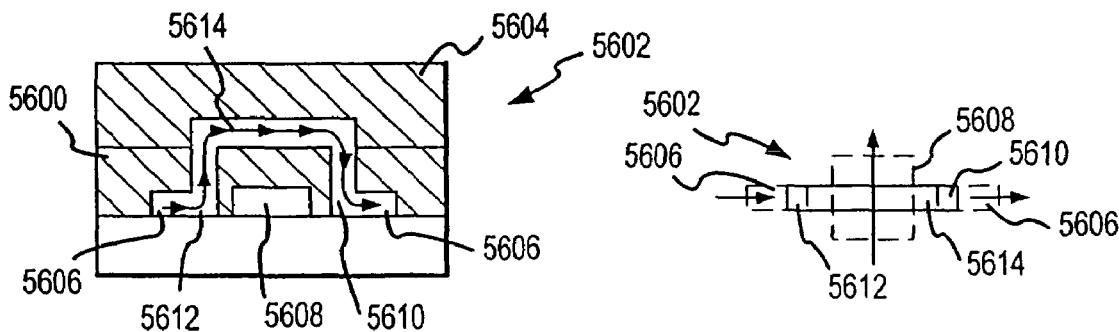
FIG.52C
FIG.52D

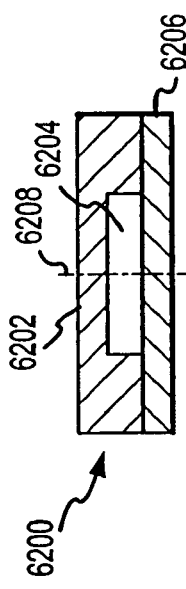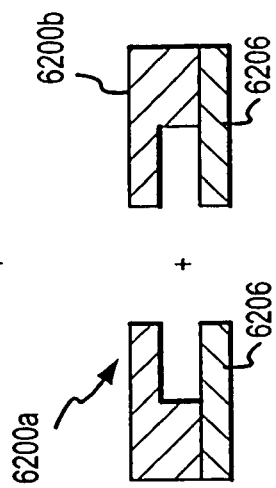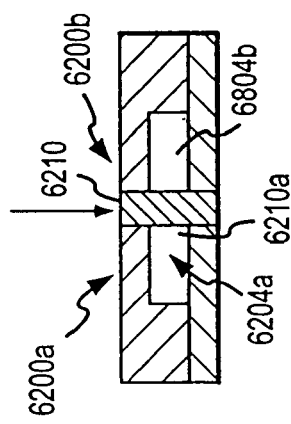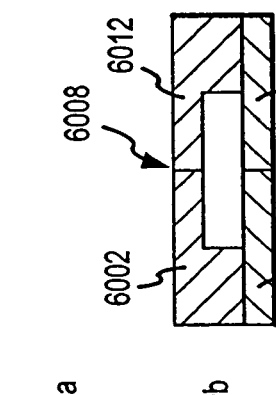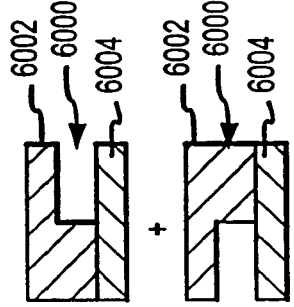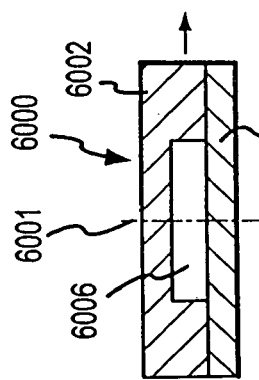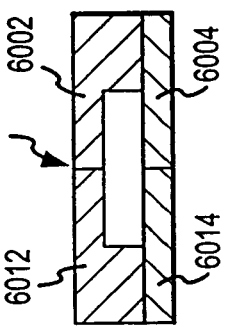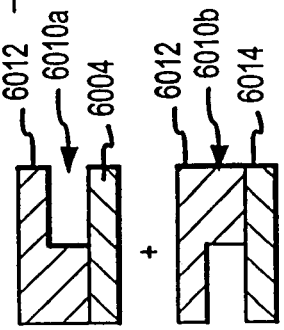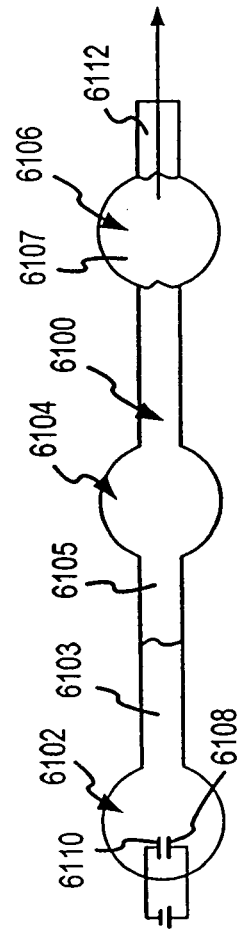

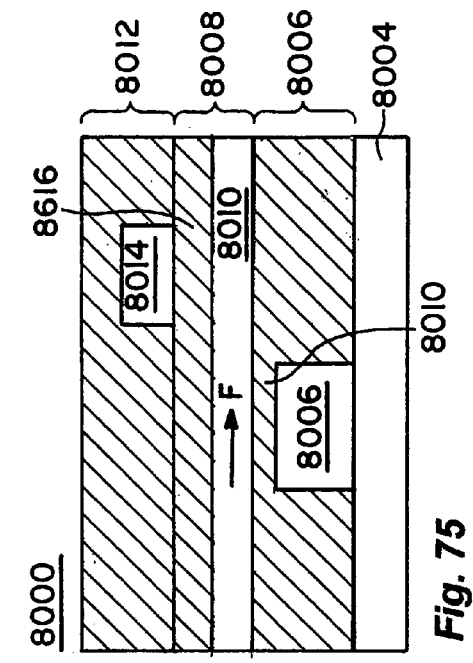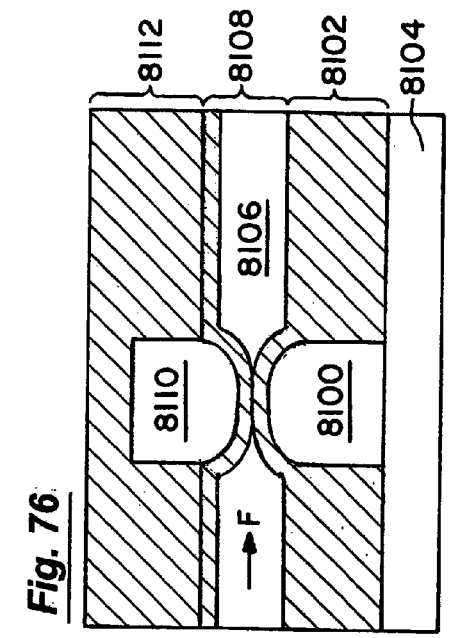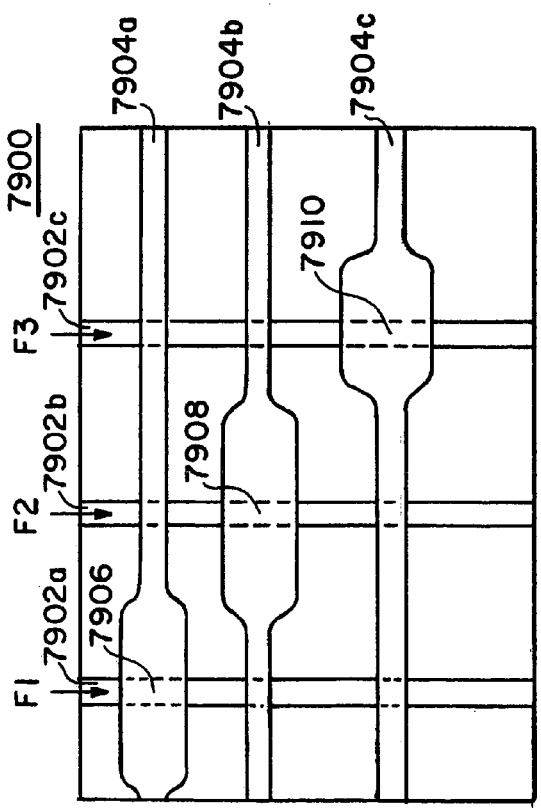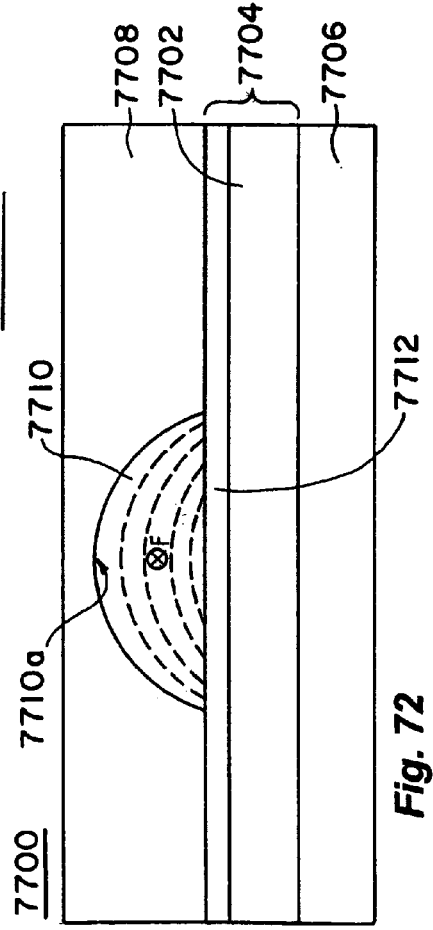

KEY
——— TOP ELASTOMER LAYER
— — — MIDDLE ELASTOMER LAYER
- - - - - BOTTOM ELASTOMER LAYER

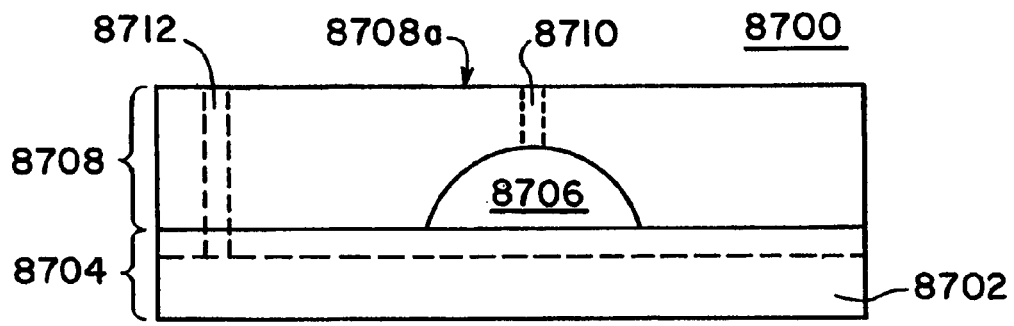
*Fig. 82A*
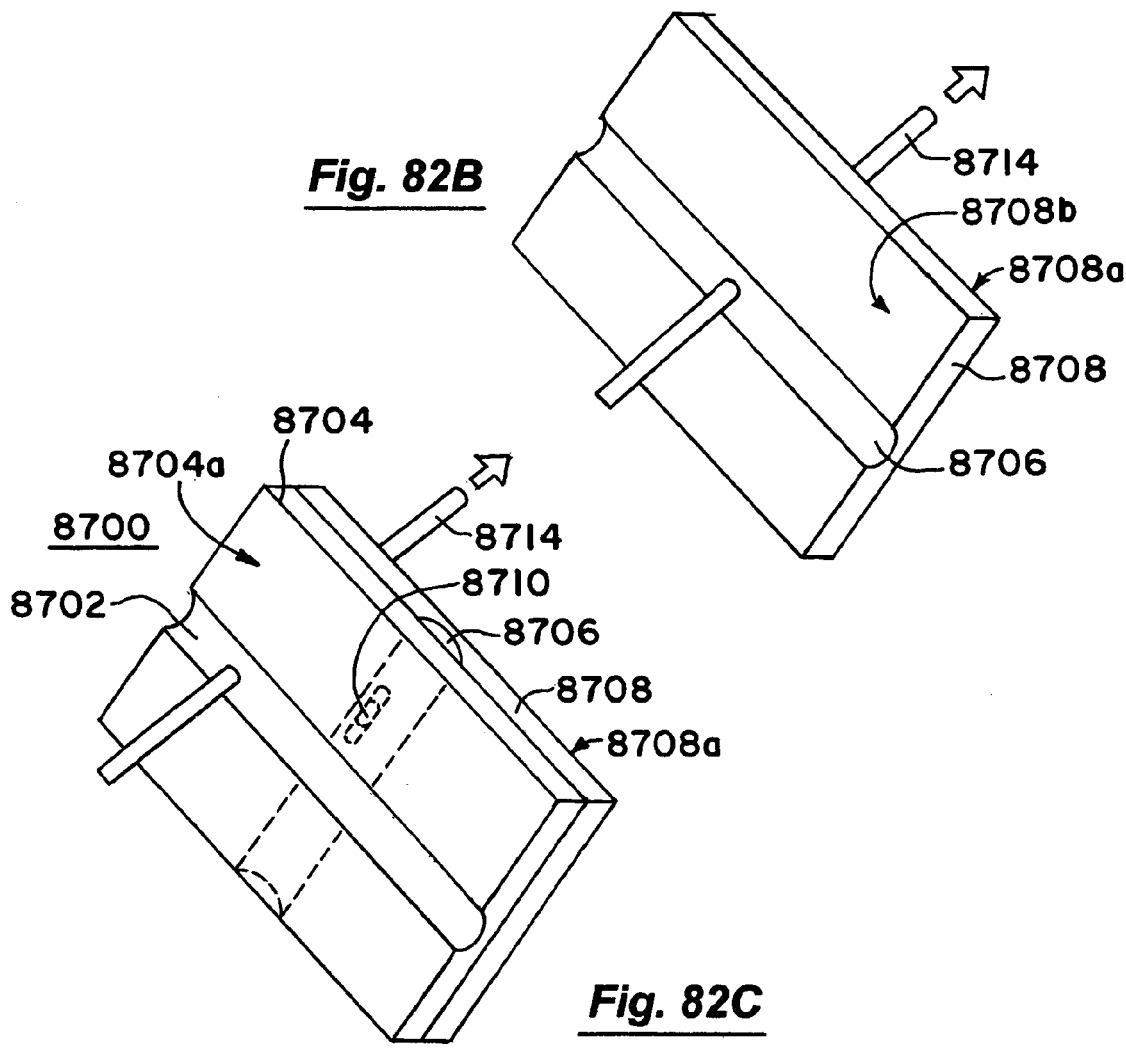
*Fig. 82B*
*Fig. 82C*

METHOD OF FORMING A VIA IN A MICROFABRICATED ELASTOMER STRUCTURE

CROSS-REFERENCE TO RELATED APPLICATIONS

This application is a divisional of U.S. patent application Ser. No. 09/997,205, filed Nov. 28, 2001 ("the '205 application") now U.S. Pat. No. 6,929,030. The '205 application is a continuation-in-part of nonprovisional patent application Ser. No. 09/826,583, filed Apr. 6, 2001 now U.S. Pat. No. 6,899,137, which is a continuation-in-part of nonprovisional patent application Ser. No. 09/724,784, filed Nov. 28, 2000 now U.S. Pat. No. 7,144,616, which is a continuation-in-part of parent nonprovisional patent application Ser. No. 09/605,520, filed Jun. 27, 2000. The parent application claims the benefit of the following previously filed provisional patent applications: U.S. provisional patent application No. 60/141,503 filed Jun. 28, 1999 now abandoned, U.S. provisional patent application No. 60/147,199 filed Aug. 3, 1999 now abandoned, and U.S. provisional patent application No. 60/186,856 filed Mar. 3, 2000 now abandoned, The text of these prior provisional and nonprovisional patent applications are hereby incorporated by reference.

STATEMENT AS TO RIGHTS TO INVENTIONS MADE UNDER FEDERALLY SPONSORED RESEARCH AND DEVELOPMENT

Work described herein has been supported, in part, by National Institute of Health grant HG-01642-02. The United States Government may therefore have certain rights in the invention.

TECHNICAL FIELD

The present invention relates to microfabricated structures and methods for producing microfabricated structures, and to microfabricated systems for regulating fluid-flow.

BACKGROUND OF THE INVENTION

Various approaches to designing micro-fluidic pumps and valves have been attempted. Unfortunately, each of these approaches suffers from its own limitations.

The two most common methods of producing microelectromechanical (MEMS) structures such as pumps and valves are silicon-based bulk micro-machining (which is a subtractive fabrication method whereby single crystal silicon is lithographically patterned and then etched to form three-dimensional structures), and surface micro-machining (which is an additive method where layers of semiconductor-type materials such as polysilicon, silicon nitride, silicon dioxide, and various metals are sequentially added and patterned to make three-dimensional structures).

A limitation of the first approach of silicon-based micro-machining is that the stiffness of the semiconductor materials used necessitates high actuation forces, which in turn result in large and complex designs. In fact, both bulk and surface micro-machining methods are limited by the stiffness of the materials used. In addition, adhesion between various layers of the fabricated device is also a problem. For example, in bulk micro-machining, wafer bonding techniques must be employed to create multilayer structures. On the other hand, when surface micro-machining, thermal stresses between the various layers of the device limits the total device thickness, often to approximately 20 microns. Using either of the above methods, clean room fabrication and careful quality control are required.

SUMMARY OF THE INVENTION

The present invention sets forth systems for fabricating and operating microfabricated structures such as on/off valves, switching valves, and pumps e.g. made out of various layers of elastomer bonded together. The present structures and methods are ideally suited for controlling and channeling fluid movement, but are not so limited.

In a preferred aspect, the present invention uses a multilayer soft lithography process to build integrated (i.e.: monolithic) microfabricated elastomeric structures.

Advantages of fabricating the present structures by binding together layers of soft elastomeric materials include the fact that the resulting devices are reduced by more than two orders of magnitude in size as compared to silicon-based devices. Further advantages of rapid prototyping, ease of fabrication, and biocompatability are also achieved.

In preferred aspects of the invention, separate elastomeric layers are fabricated on top of micromachined molds such that recesses are formed in each of the various elastomeric layers. By bonding these various elastomeric layers together, the recesses extending along the various elastomeric layers form flow channels and control lines through the resulting monolithic, integral elastomeric structure. In various aspects of the invention, these flow channels and control lines which are formed in the elastomeric structure can be actuated to function as micro-pumps and micro-valves, as will be explained.

In further optional aspects of the invention, the monolithic elastomeric structure is sealed onto the top of a planar substrate, with flow channels being formed between the surface of the planar substrate and the recesses which extend along the bottom surface of the elastomeric structure.

In one preferred aspect, the present monolithic elastomeric structures are constructed by bonding together two separate layers of elastomer with each layer first being separately cast from a micromachined mold. Preferably, the elastomer used is a two-component addition cure material in which the bottom elastomeric layer has an excess of one component, while the top elastomeric layer has an excess of another component. In an exemplary embodiment, the elastomer used is silicone rubber. Two layers of elastomer are cured separately. Each layer is separately cured before the top layer is positioned on the bottom layer. The two layers are then bonded together. Each layer preferably has an excess of one of the two components, such that reactive molecules remain at the interface between the layers. The top layer is assembled on top of the bottom layer and heated. The two layers bond irreversibly such that the strength of the interface approaches or equals the strength of the bulk elastomer. This creates a monolithic three-dimensional patterned structure composed entirely of two layers of bonded together elastomer. Additional layers may be added by simply repeating the process, wherein new layers, each having a layer of opposite "polarity" are cured, and thereby bonded together.

In a second preferred aspect, a first photoresist layer is deposited on top of a first elastomeric layer. The first photoresist layer is then patterned to leave a line or pattern of lines of photoresist on the top surface of the first elastomeric layer. Another layer of elastomer is then added and cured, encapsulating the line or pattern of lines of photoresist. A second photoresist layer is added and patterned, and another layer of elastomer added and cured, leaving line and patterns of lines of photoresist encapsulated in a monolithic elastomer structure. This process may be repeated to add more encapsulated patterns and elastomer layers. Thereafter, the photoresist is removed leaving flow channel(s) and control line(s) in the spaces which had been occupied by the photoresist. This process may be repeated to create elastomer structures having a multitude of layers.

An advantage of patterning moderate sized features (>/=10 microns) using a photoresist method is that a high resolution transparency film can be used as a contact mask. This allows a single researcher to design, print, pattern the mold, and create a new set of cast elastomer devices, typically all within 24 hours.

A further advantage of either above embodiment of the present invention is that due to its monolithic or integral nature, (i.e., all the layers are composed of the same material) is that interlayer adhesion failures and thermal stress problems are completely avoided.

Further advantages of the present invention's preferred use of a silicone rubber or elastomer such as RTV 615 manufactured by General Electric, is that it is transparent to visible light, making a multilayer optical trains possible, thereby allowing optical interrogation of various channels or chambers in the microfluidic device. As appropriately shaped elastomer layers can serve as lenses and optical elements, bonding of layers allows the creation of multilayer optical trains. In addition, GE RTV 615 elastomer is biocompatible. Being soft, closed valves form a good seal even if there are small particulates in the flow channel. Silicone rubber is also bio-compatible and inexpensive, especially when compared with a single crystal silicon.

Monolithic elastomeric valves and pumps also avoid many of the practical problems affecting flow systems based on electro-osmotic flow. Typically, electro-osmotic flow systems suffer from bubble formation around the electrodes and the flow is strongly dependent on the composition of the flow medium. Bubble formation seriously restricts the use of electro-osmotic flow in microfluidic devices, making it difficult to construct functioning integrated devices. The magnitude of flow and even its direction typically depends in a complex fashion on ionic strength and type, the presence of surfactants and the charge on the walls of the flow channel. Moreover, since electrolysis is taking place continuously, the eventual capacity of buffer to resist pH changes may also be reached. Furthermore, electro-osmotic flow always occurs in competition with electrophoresis. As different molecules may have different electrophoretic mobilities, unwanted electrophoretic separation may occur in the electro-osmotic flow. Finally, electro-osmotic flow can not easily be used to stop flow, halt diffusion, or to balance pressure differences.

A further advantage of the present monolithic elastomeric valve and pump structures are that they can be actuated at very high speeds. For example, the present inventors have achieved a response time for a valve with aqueous solution therein on the order of one millisecond, such that the valve opens and closes at speeds approaching or exceeding 100 Hz. In particular, a non-exclusive list of ranges of cycling speeds for the opening and closing of the valve structure include between about 0.001 and 10000 ms, between about 0.01 and 1000 ms, between about 0.1 and 100 ms, and between about 1 and 10 ms. The cycling speeds depend upon the composition and structure of a valve used for a particular application and the method of actuation, and thus cycling speeds outside of the listed ranges would fall within the scope of the present invention.

Further advantages of the present pumps and valves are that their small size makes them fast and their softness contributes to making them durable. Moreover, as they close linearly with differential applied pressure, this linear relationship allows fluid metering and valve closing in spite of high back pressures.

In various aspects of the invention, a plurality of flow channels pass through the elastomeric structure with a second flow channel extending across and above a first flow channel. In this aspect of the invention, a thin membrane of elastomer separates the first and second flow channels. As will be explained, downward movement of this membrane (due to the second flow channel being pressurized or the membrane being otherwise actuated) will cut off flow passing through the lower flow channel.

In optional preferred aspects of the present systems, a plurality of individually addressable valves are formed connected together in an elastomeric structure and are then activated in sequence such that peristaltic pumping is achieved. More complex systems including networked or multiplexed control systems, selectably addressable valves disposed in a grid of valves, networked or multiplexed reaction chamber systems and biopolymer synthesis systems are also described.

One embodiment of a microfabricated elastomeric structure in accordance with the present invention comprises an elastomeric block formed with first and second microfabricated recesses therein, a portion of the elastomeric block deflectable when the portion is actuated.

One embodiment of a method of microfabricating an elastomeric structure comprises the steps of microfabricating a first elastomeric layer, microfabricating a second elastomeric layer; positioning the second elastomeric layer on top of the first elastomeric layer, and bonding a bottom surface of the second elastomeric layer onto a top surface of the first elastomeric layer.

A first alternative embodiment of a method of microfabricating an elastomeric structure comprises the steps of forming a first elastomeric layer on top of a first micromachined mold, the first micromachined mold having at least one first raised protrusion which forms at least one first channel in the bottom surface of the first elastomeric layer. A second elastomeric layer is formed on top of a second micromachined mold, the second micromachined mold having at least one second raised protrusion which forms at least one second channel in the bottom surface of the second elastomeric layer. The bottom surface of the second elastomeric layer is bonded onto a top surface of the first elastomeric layer such that the at least one second channel is enclosed between the first and second elastomeric layers.

A second alternative embodiment of a method of microfabricating an elastomeric structure in accordance with the present invention comprises the steps of forming a first elastomeric layer on top of a substrate, curing the first elastomeric layer, and depositing a first sacrificial layer on the top surface of the first elastomeric layer. A portion of the first sacrificial layer is removed such that a first pattern of sacrificial material remains on the top surface of the first elastomeric layer. A second elastomeric layer is formed over the first elastomeric layer thereby encapsulating the first pattern of sacrificial material between the first and second elastomeric layers. The second elastomeric layer is cured and then sacrificial material is removed thereby forming at least one first recess between the first and second layers of elastomer.

An embodiment of a method of actuating an elastomeric structure in accordance with the present invention comprises providing an elastomeric block formed with first and second microfabricated recesses therein, the first and second microfabricated recesses being separated by a portion of the structure which is deflectable into either of the first or second recesses when the other of the first and second recesses. One of the recesses is pressurized such that the portion of the elastomeric structure separating the second recess from the first recess is deflected into the other of the two recesses.

In other optional preferred aspects, magnetic or conductive materials can be added to make layers of the elastomer magnetic or electrically conducting, thus enabling the creation of all elastomer electromagnetic devices.

BRIEF DESCRIPTION OF THE DRAWINGS

Part I—FIGS. 1 to 7A Illustrate Successive Steps of a First Method of Fabricating the Present Invention, as follows.

Figure 7A:
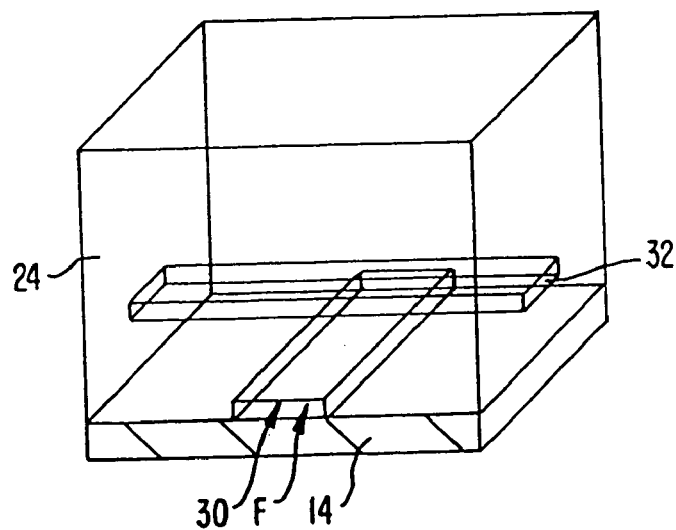
FIG. 7A is an illustration corresponding to FIG. 6, but showing the elastomeric structure sealed onto the planar substrate.
Figure 7B:
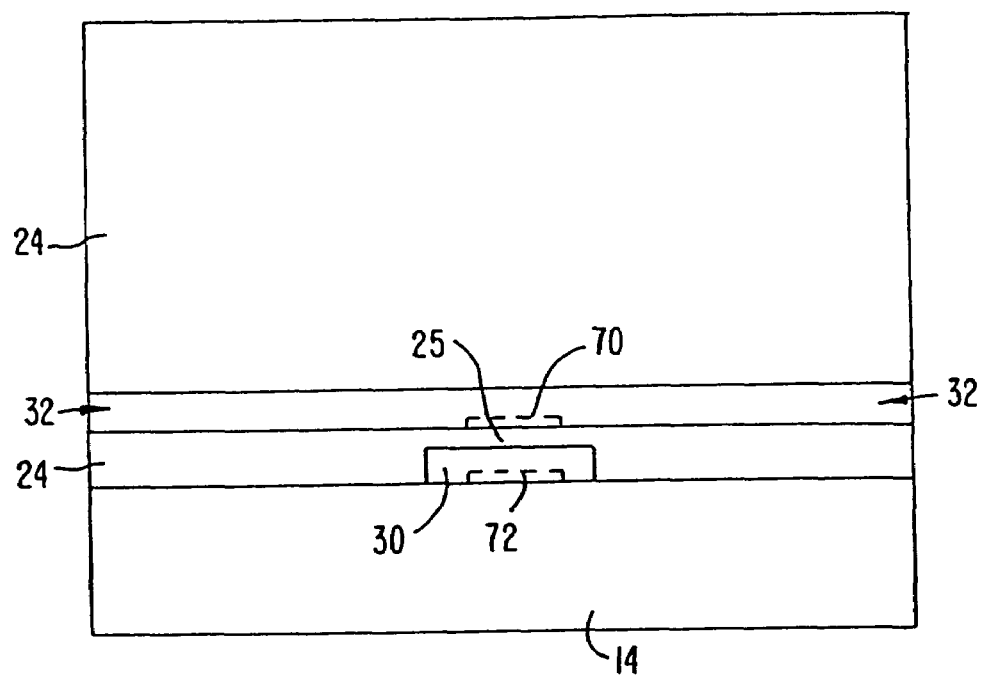
FIG. 7B is a front sectional view corresponding to FIG. 7A, showing an open flow channel.
Figure 7H:
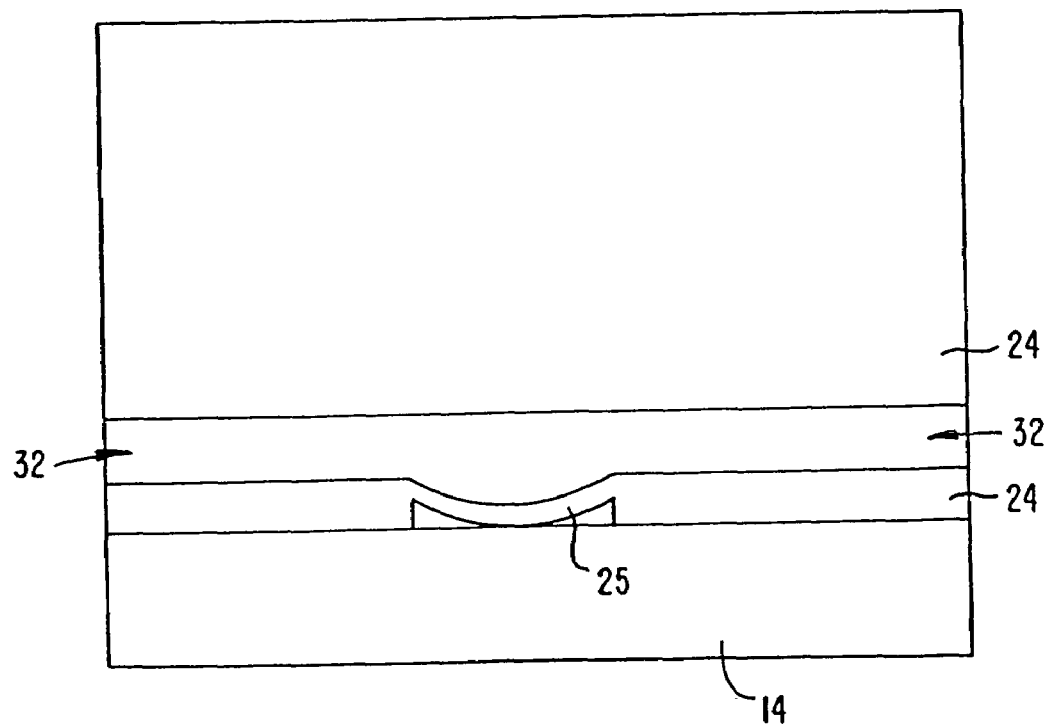
FIGS. 7C-7G are illustrations showing steps of a method for forming an elastomeric structure having a membrane formed from a separate elastomeric layer.

Part II—FIG. 7H Show the Closing of a First Flow Channel by Pressurizing a Second Flow Channel, as Follows:

FIG. 7H corresponds to FIG. 7A, but shows a first flow channel closed by pressurization in second flow channel.

Figure 8:
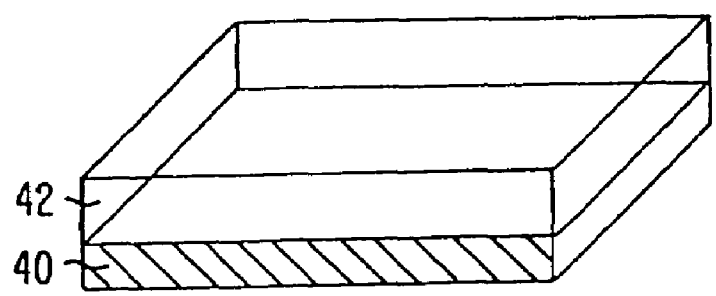

Part III—FIGS. 8 to 18 Illustrate Successive Steps of a Second Method of Fabricating the Present Invention, as Follows:

FIG. 8 is an illustration of a first elastomeric layer deposited on a planar substrate.

Figure 9:
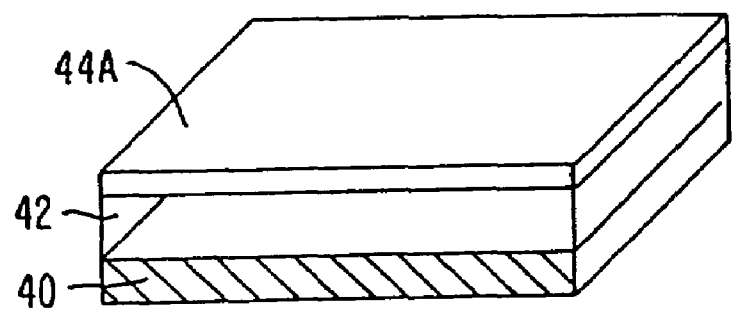

FIG. 9 is an illustration showing a first photoresist layer deposited on top of the first elastomeric layer of FIG. 8.

Figure 10:
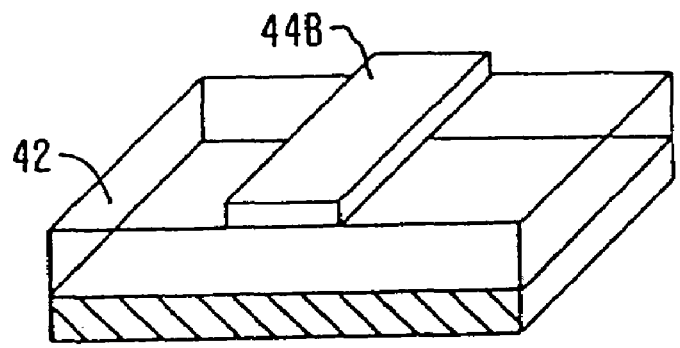

FIG. 10 is an illustration showing the system of FIG. 9, but with a portion of the first photoresist layer removed, leaving only a first line of photoresist.

Figure 11:
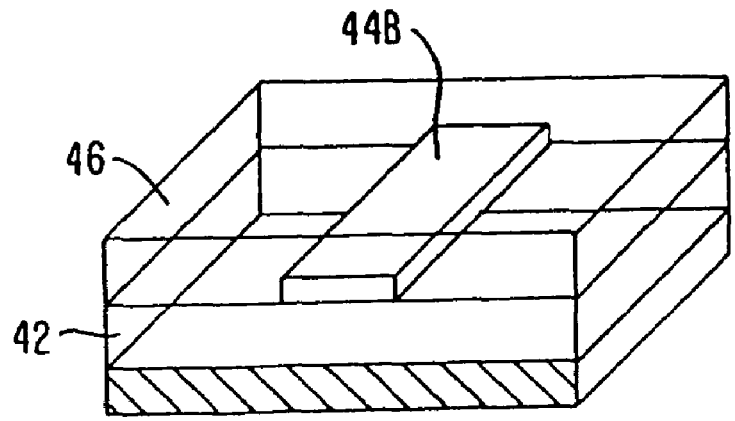

FIG. 11 is an illustration showing a second elastomeric layer applied on top of the first elastomeric layer over the first line of photoresist of FIG. 10, thereby encasing the photoresist between the first and second elastomeric layers.

Figure 12:
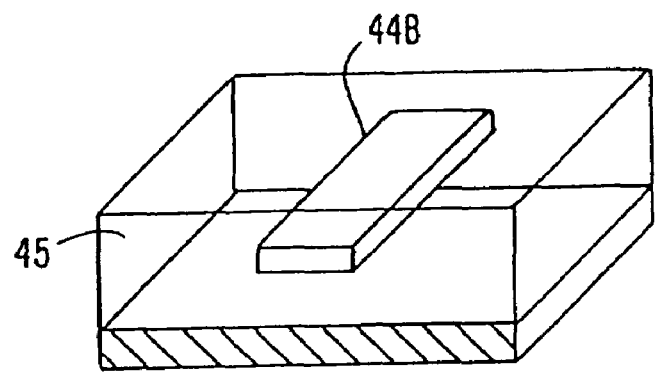

FIG. 12 corresponds to FIG. 11, but shows the integrated monolithic structure produced after the first and second elastomer layers have been bonded together.

Figure 13:
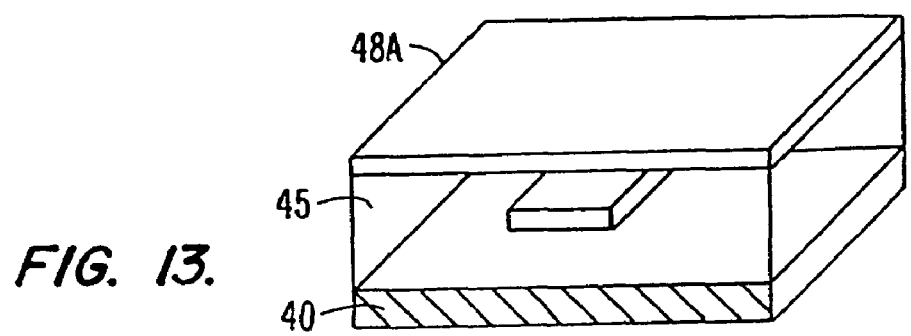

FIG. 13 is an illustration showing a second photoresist layer deposited on top of the integral elastomeric structure of FIG. 12.

Figure 14:
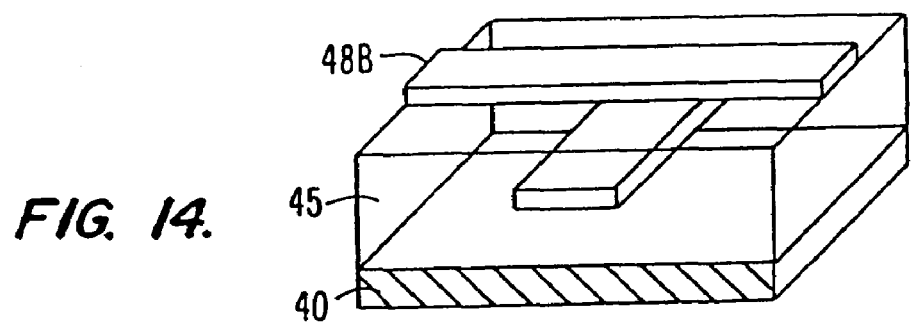

FIG. 14 is an illustration showing the system of FIG. 13, but with a portion of the second photoresist layer removed, leaving only a second line of photoresist.

Figure 15:
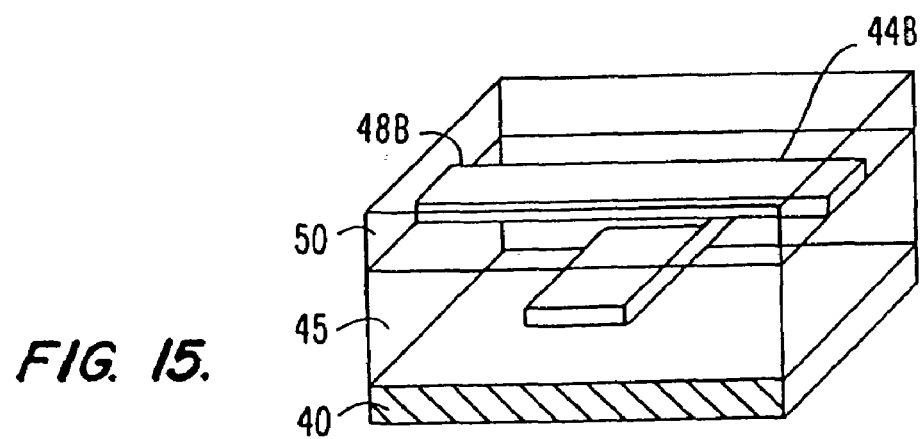

FIG. 15 is an illustration showing a third elastomer layer applied on top of the second elastomeric layer and over the second line of photoresist of FIG. 14, thereby encapsulating the second line of photoresist between the elastomeric structure of FIG. 12 and the third elastomeric layer.

Figure 16:
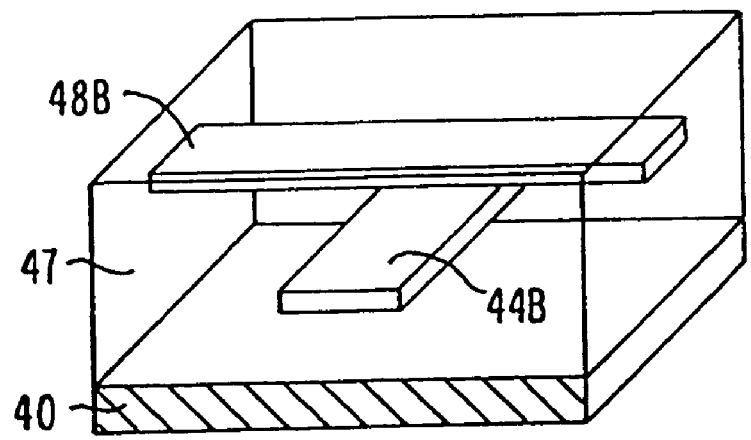

FIG. 16 corresponds to FIG. 15, but shows the third elastomeric layer cured so as to be bonded to the monolithic structure composed of the previously bonded first and second elastomer layers.

Figure 17:
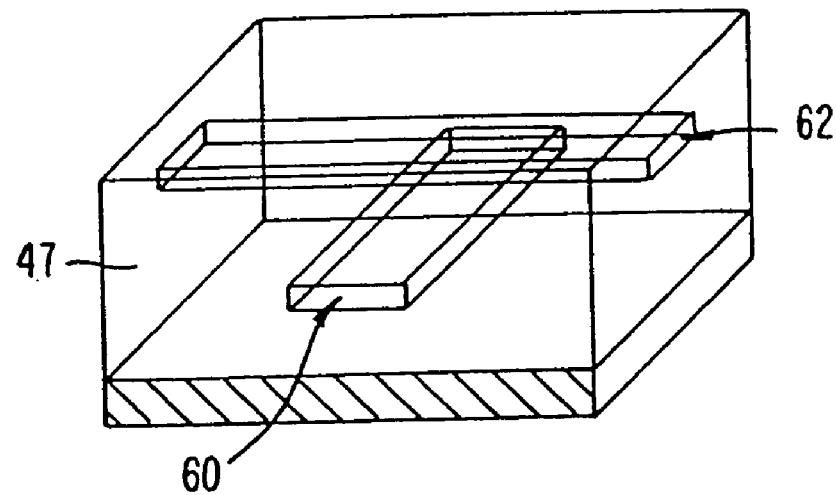

FIG. 17 corresponds to FIG. 16, but shows the first and second lines of photoresist removed so as to provide two perpendicular overlapping, but not intersecting, flow channels passing through the integrated elastomeric structure.

Figure 18:
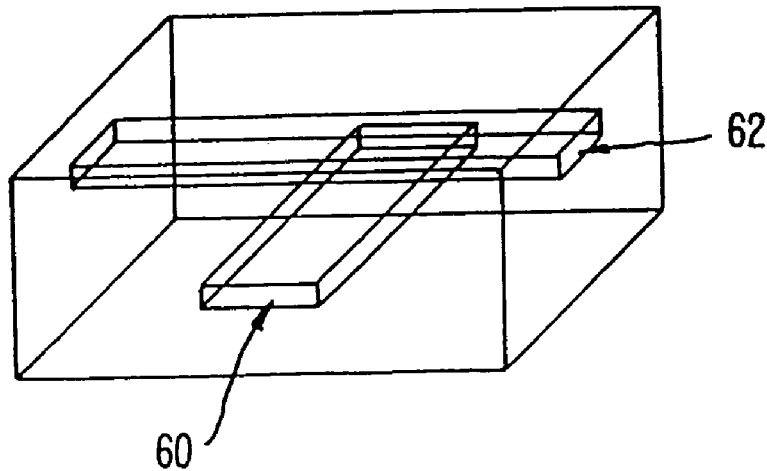

FIG. 18 is an illustration showing the system of FIG. 17, but with the planar substrate thereunder removed.

Figure 19:
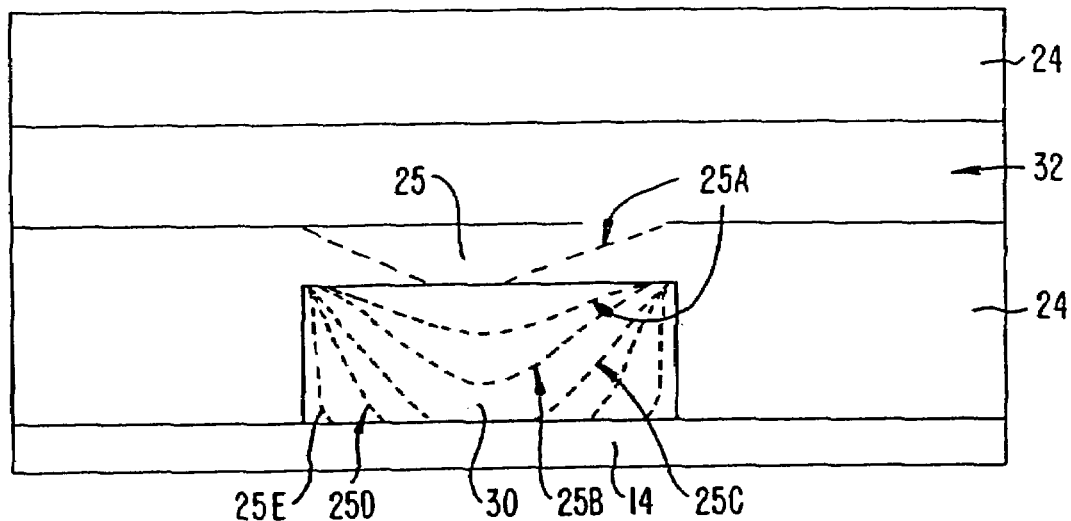
Figure 20:
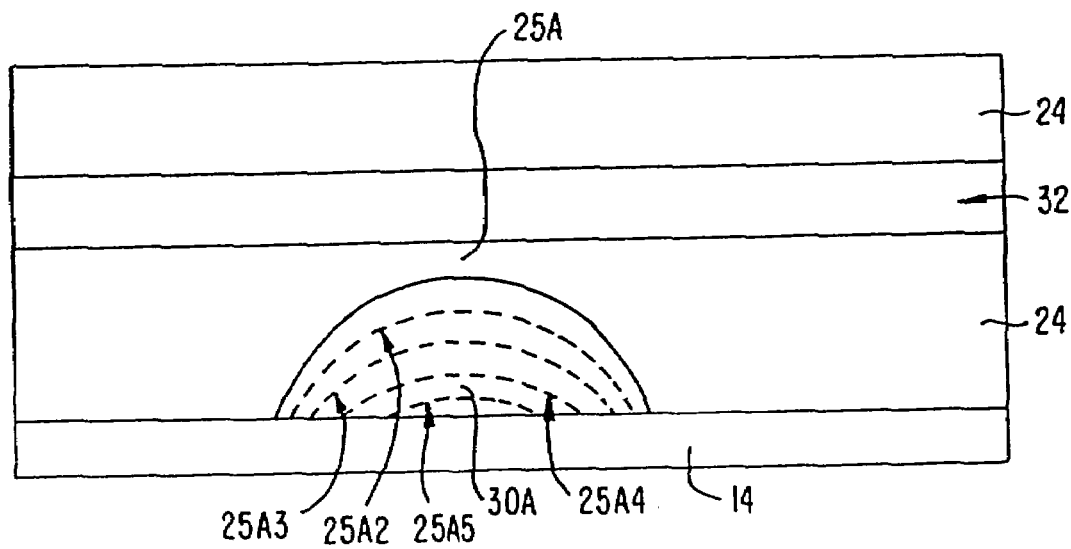

Part IV—FIGS. 19 and 20 Show Further Details of Different Flow Channel Cross-Sections, as Follows:

FIG. 19 shows a rectangular cross-section of a first flow channel.

FIG. 20 shows the flow channel cross section having a curved upper surface.

Part V—FIGS. 21 to 24 Show Experimental Results Achieved by Preferred Embodiments of the Present Microfabricated Valve:

FIG. 21 illustrates valve opening vs. applied pressure for various flow channels.

Figure 22:
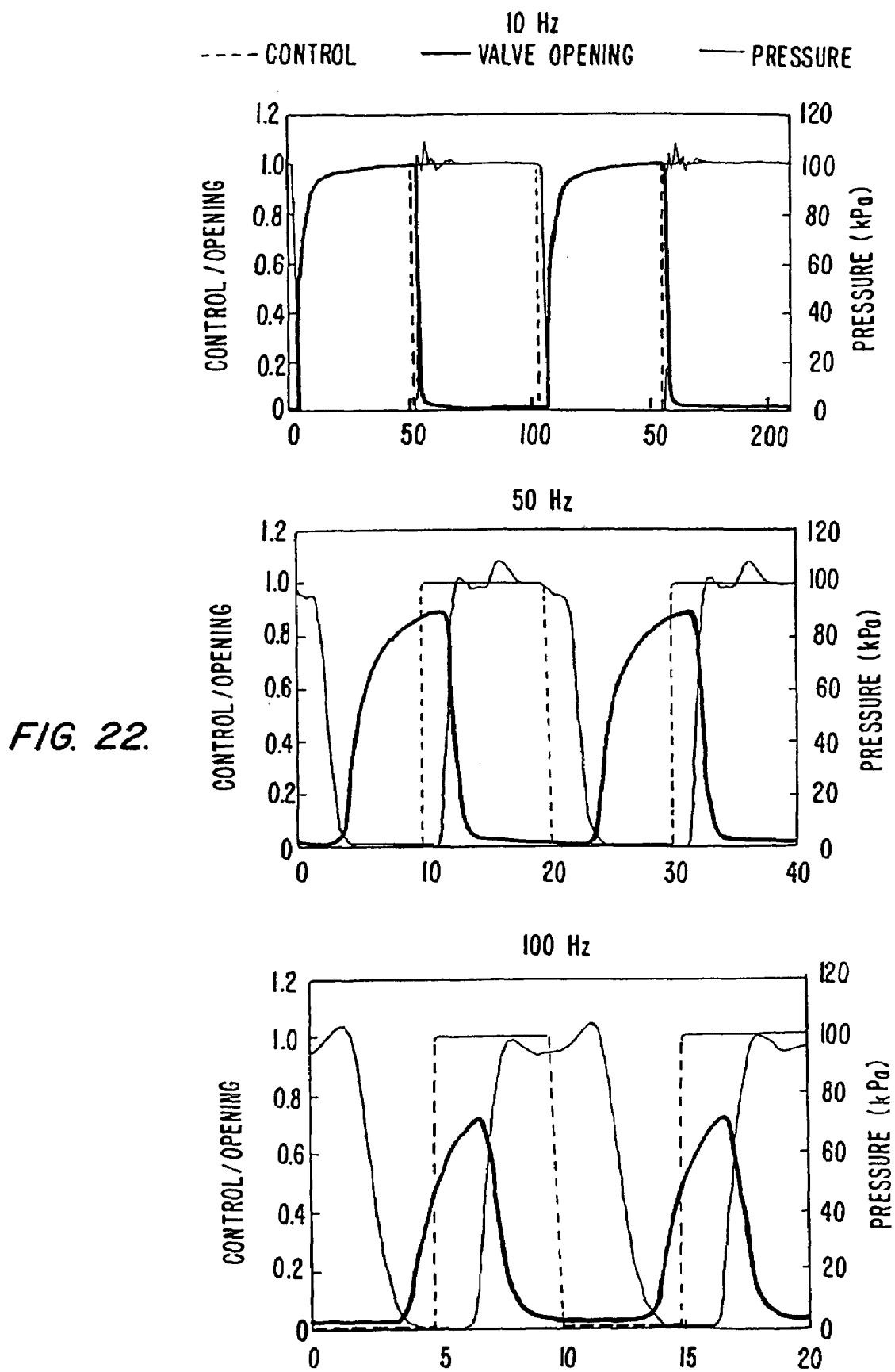

FIG. 22 illustrates time response of a 100 μm×100 μm×10 μm RTV microvalve.

Figure 23A:
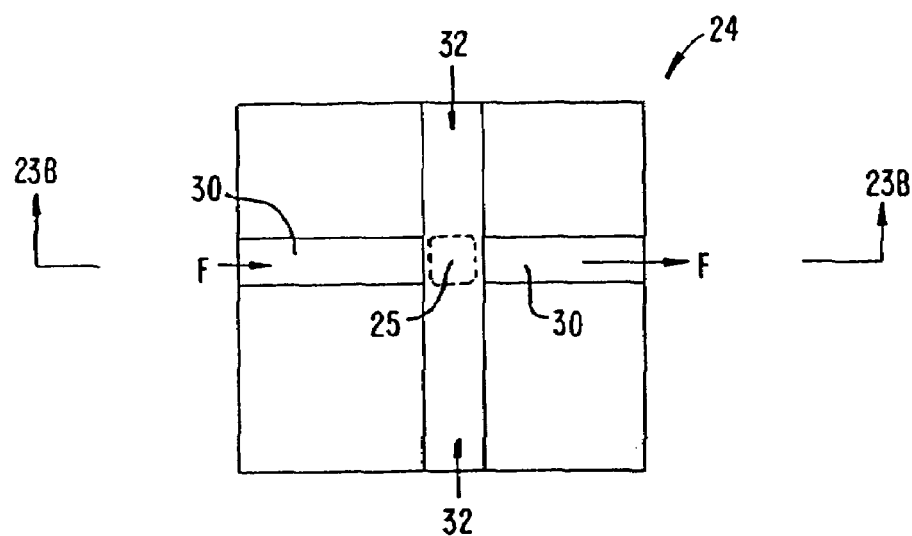

Part VI—FIGS. 23A to 33 Show Various Microfabricated Structures, Networked Together According to Aspects of the Present Invention:

FIG. 23A is a top schematic view of an on/off valve.

Figure 23B:
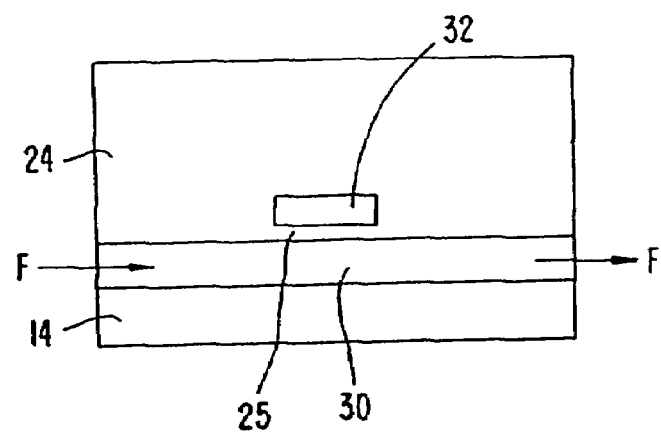

FIG. 23B is a sectional elevation view along line 23B-23B in FIG. 23A

FIG. 24 is a top schematic view of a peristaltic pumping system.

Figure 24A:
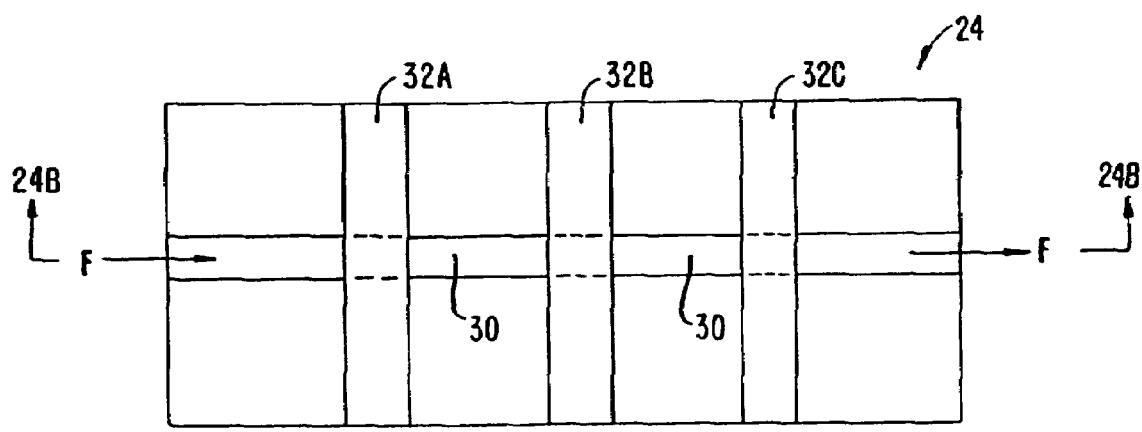
Figure 24B:
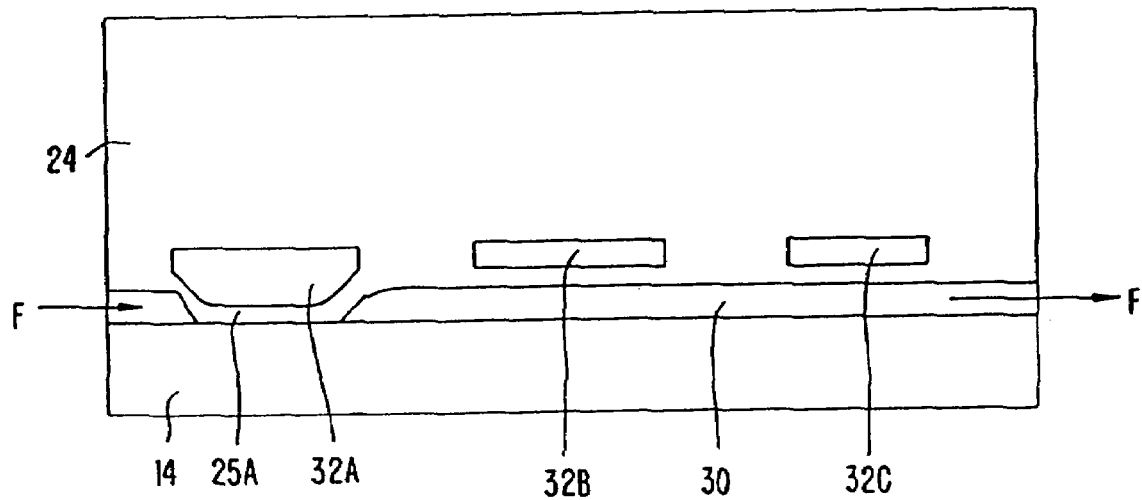

FIG. 24B is a sectional elevation view along line 24B-24B in FIG. 24A

Figure 25:
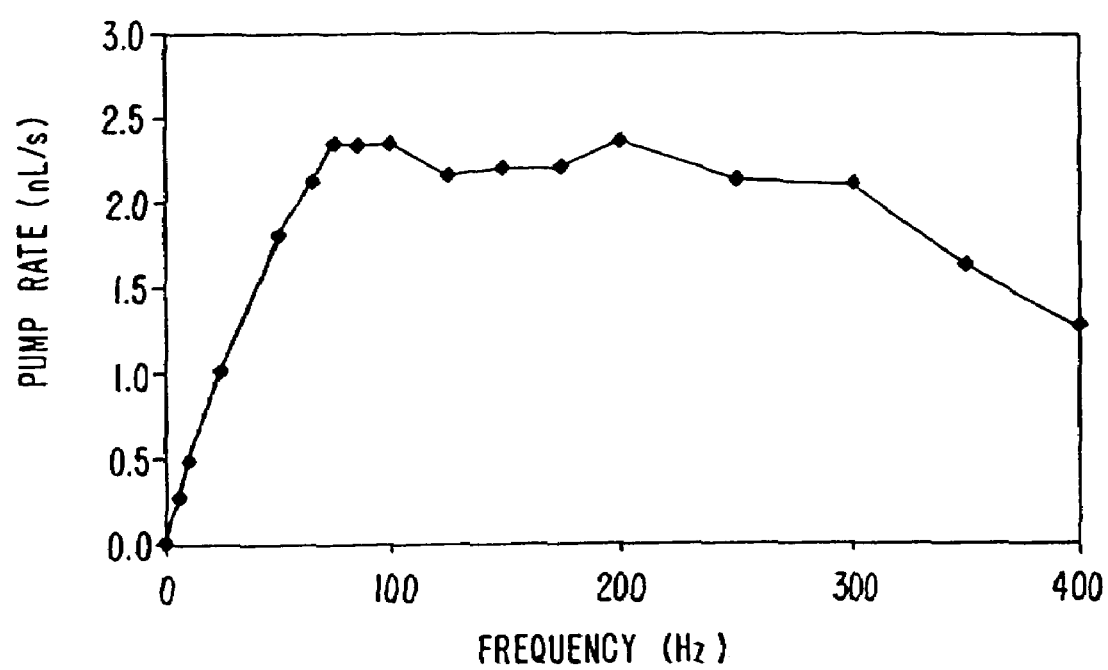

FIG. 25 is a graph showing experimentally achieved pumping rates vs. frequency for an embodiment of the peristaltic pumping system of FIG. 24.

Figure 26A:
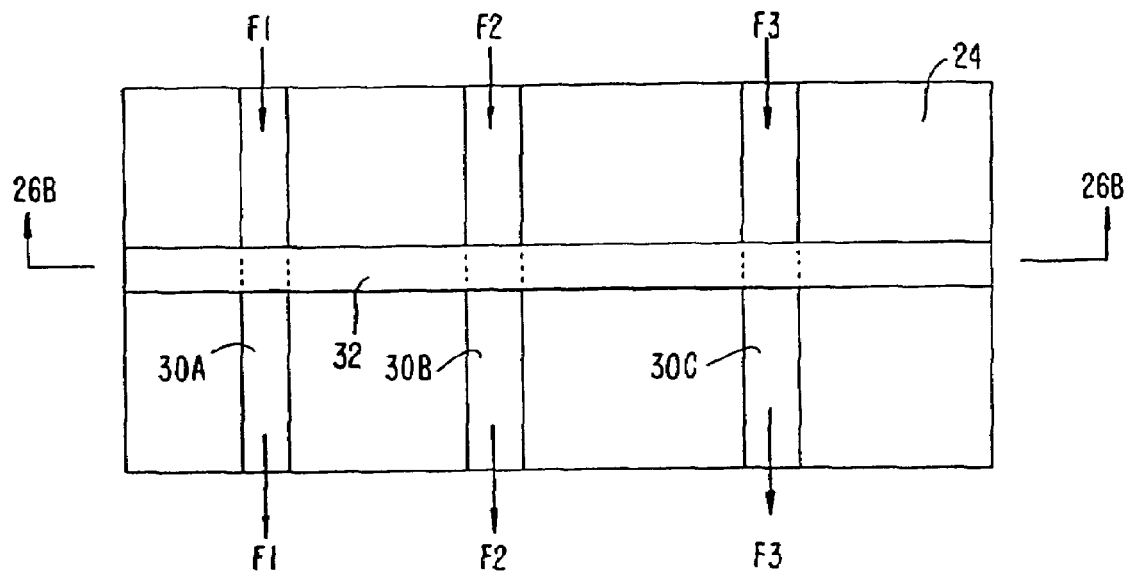

FIG. 26A is a top schematic view of one control line actuating multiple flow lines simultaneously.

Figure 26B:
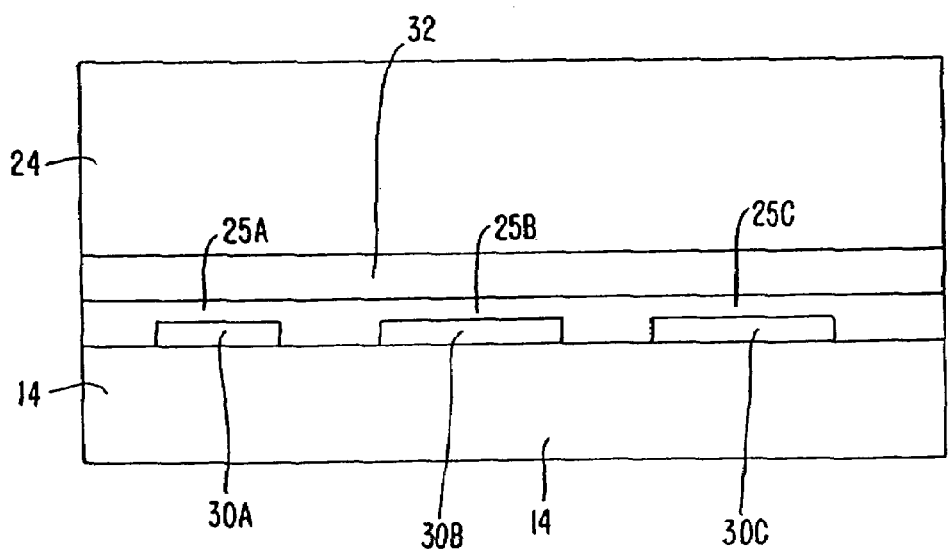

FIG. 26B is a sectional elevation view along line 26B-26B in FIG. 26A

Figure 27:
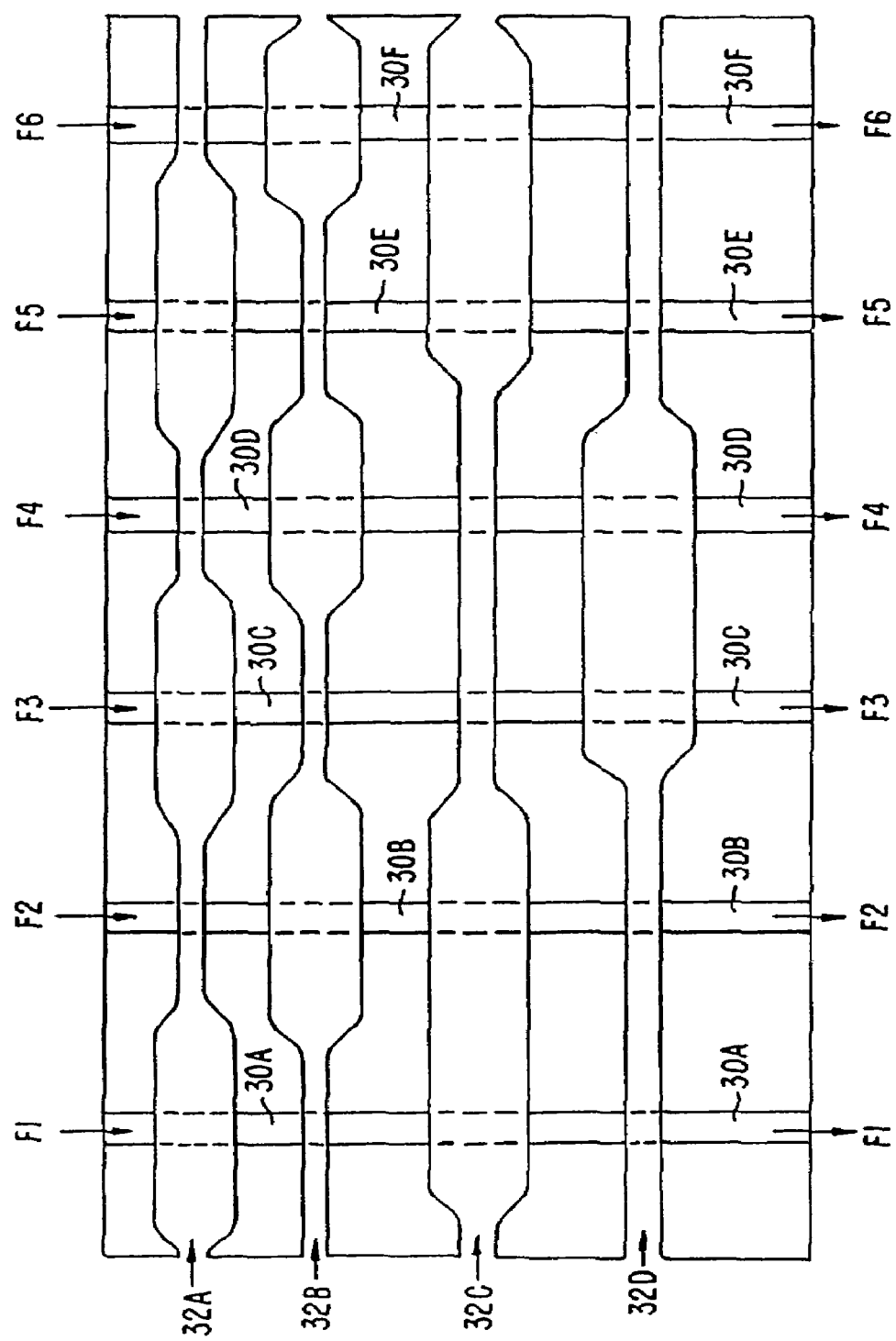

FIG. 27 is a schematic illustration of a multiplexed system adapted to permit flow through various channels.

Figure 28A:
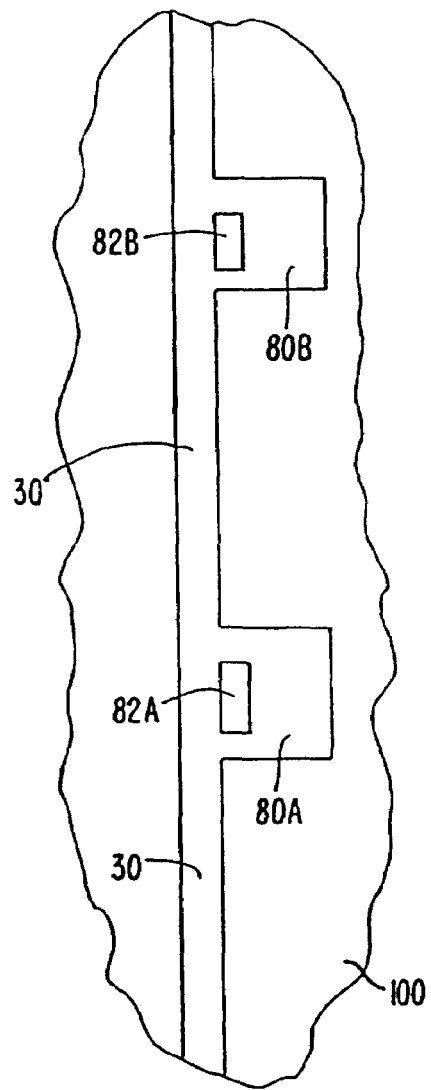

FIG. 28A is a plan view of a flow layer of an addressable reaction chamber structure.

Figure 28B:
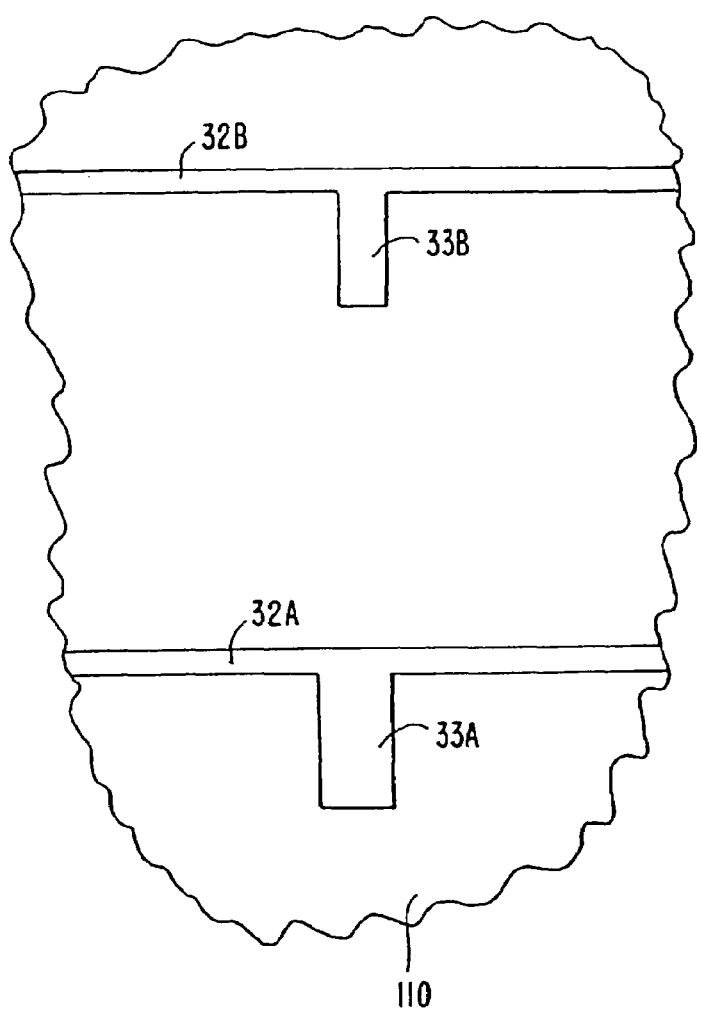

FIG. 28B is a bottom plan view of a control channel layer of an addressable reaction chamber structure.

Figure 28C:
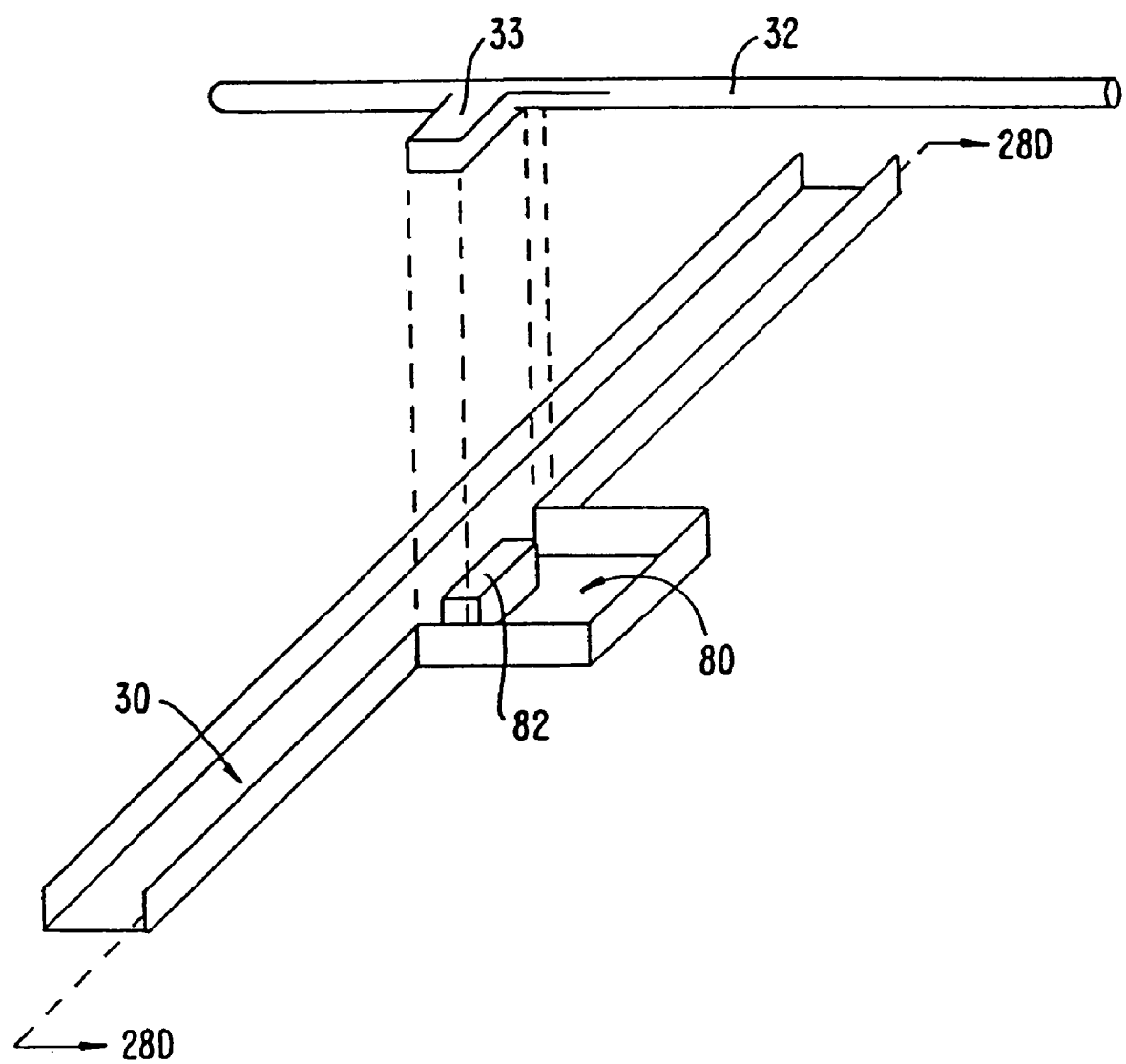

FIG. 28C is an exploded perspective view of the addressable reaction chamber structure formed by bonding the control channel layer of FIG. 28B to the top of the flow layer of FIG. 28A.

Figure 28D:
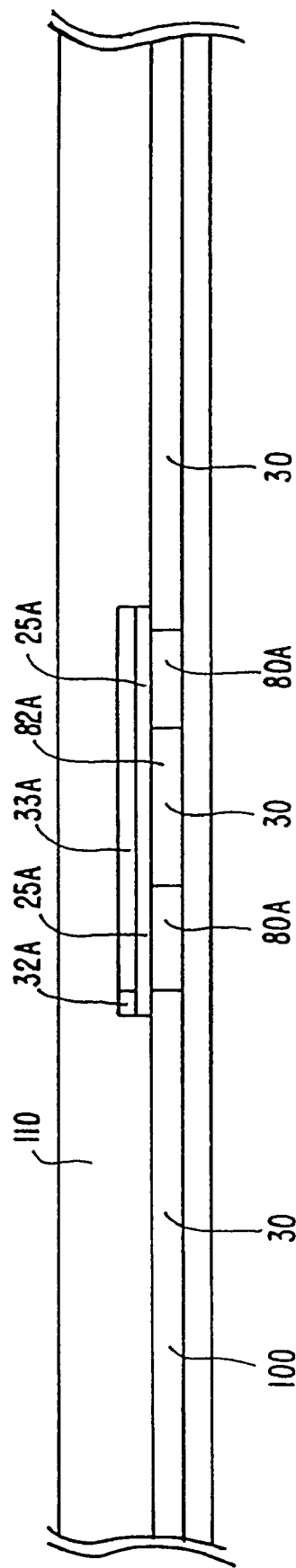

FIG. 28D is a sectional elevation view corresponding to FIG. 28C, taken along line 28D-28D in FIG. 28C.

Figure 29:
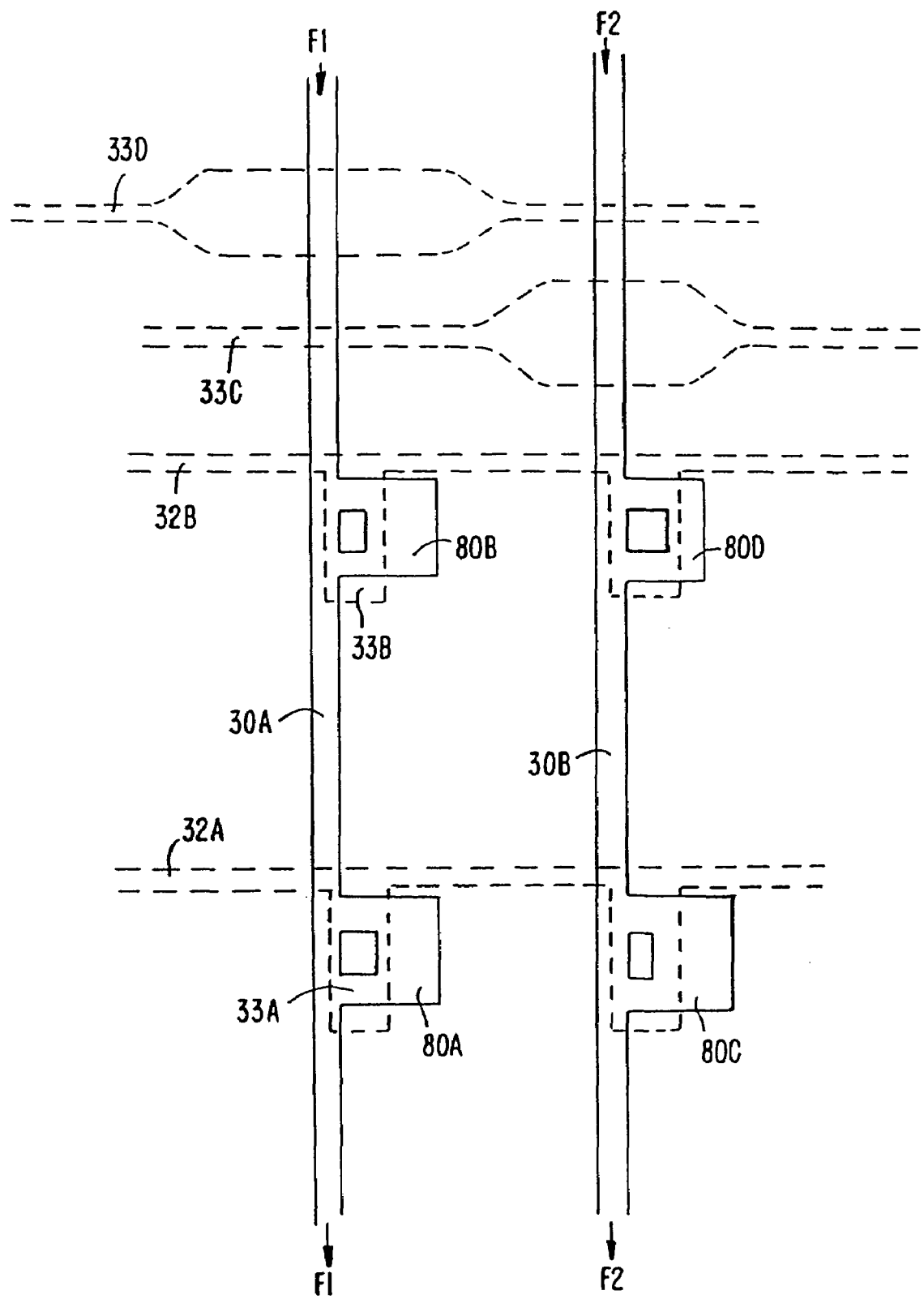

FIG. 29 is a schematic of a system adapted to selectively direct fluid flow into any of an array of reaction wells.

Figure 30:
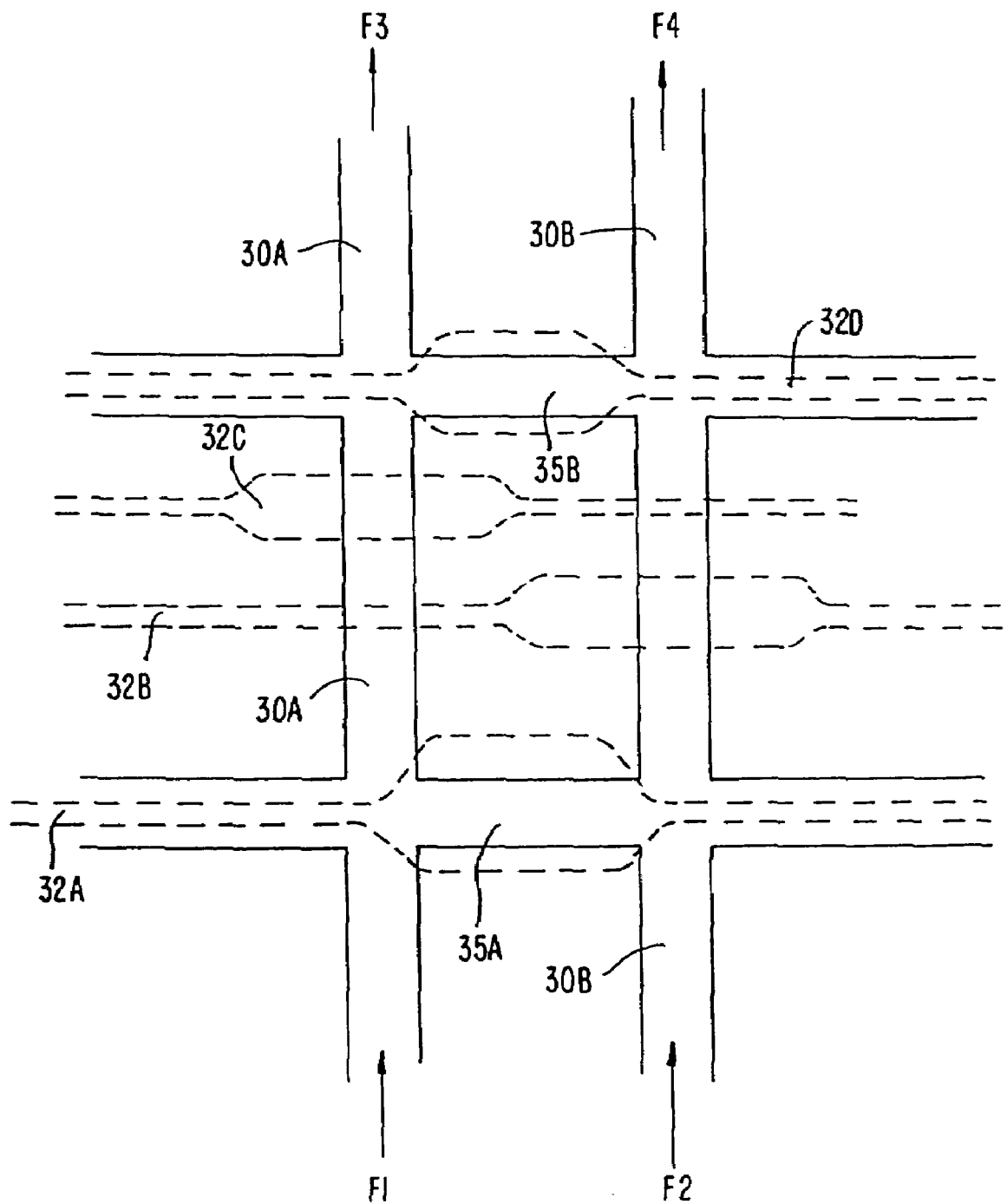

FIG. 30 is a schematic of a system adapted for selectable lateral flow between parallel flow channels.

Figure 31A:
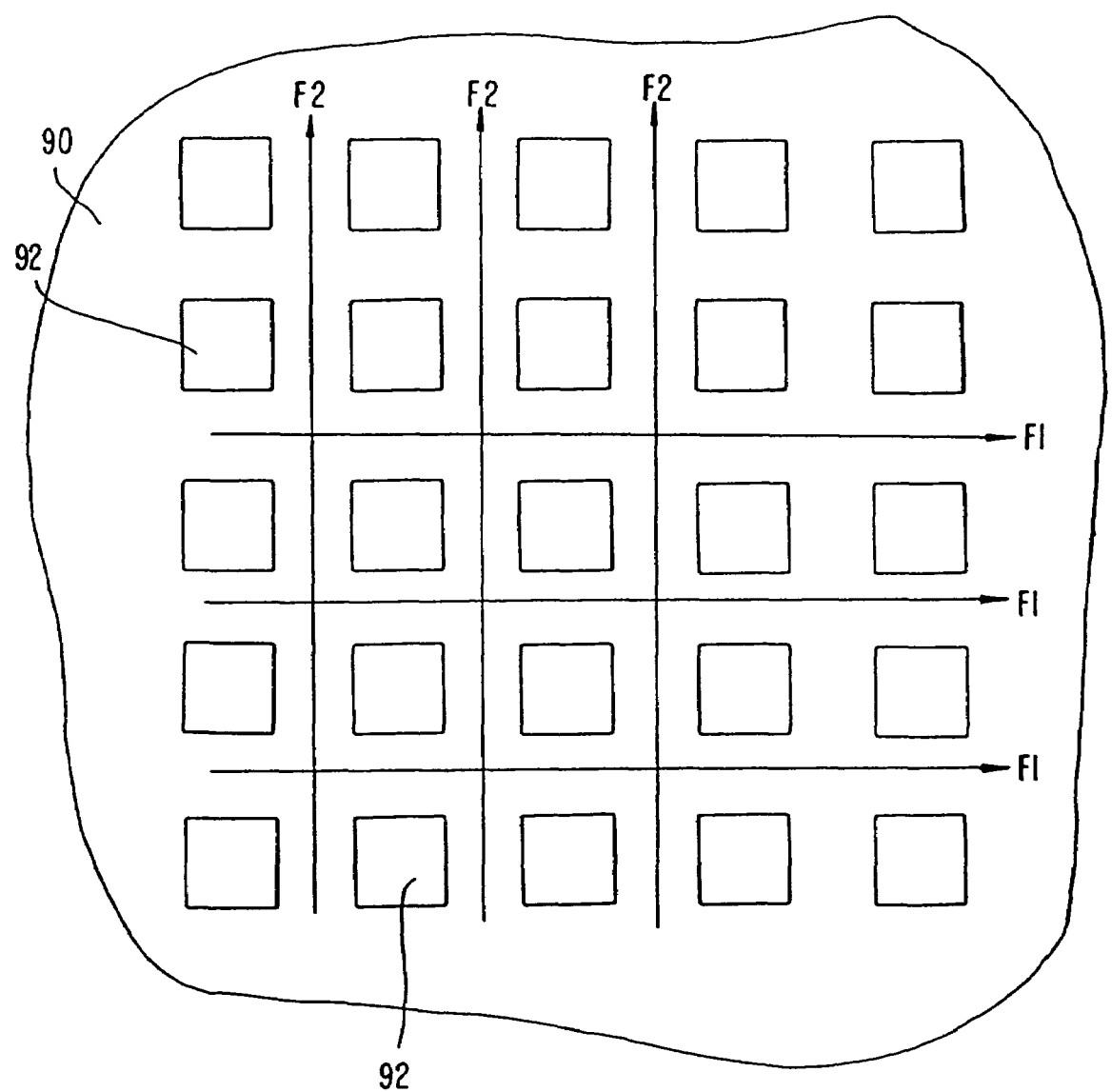

FIG. 31A is a bottom plan view of first layer (i.e.: the flow channel layer) of elastomer of a switchable flow array.

Figure 31B:
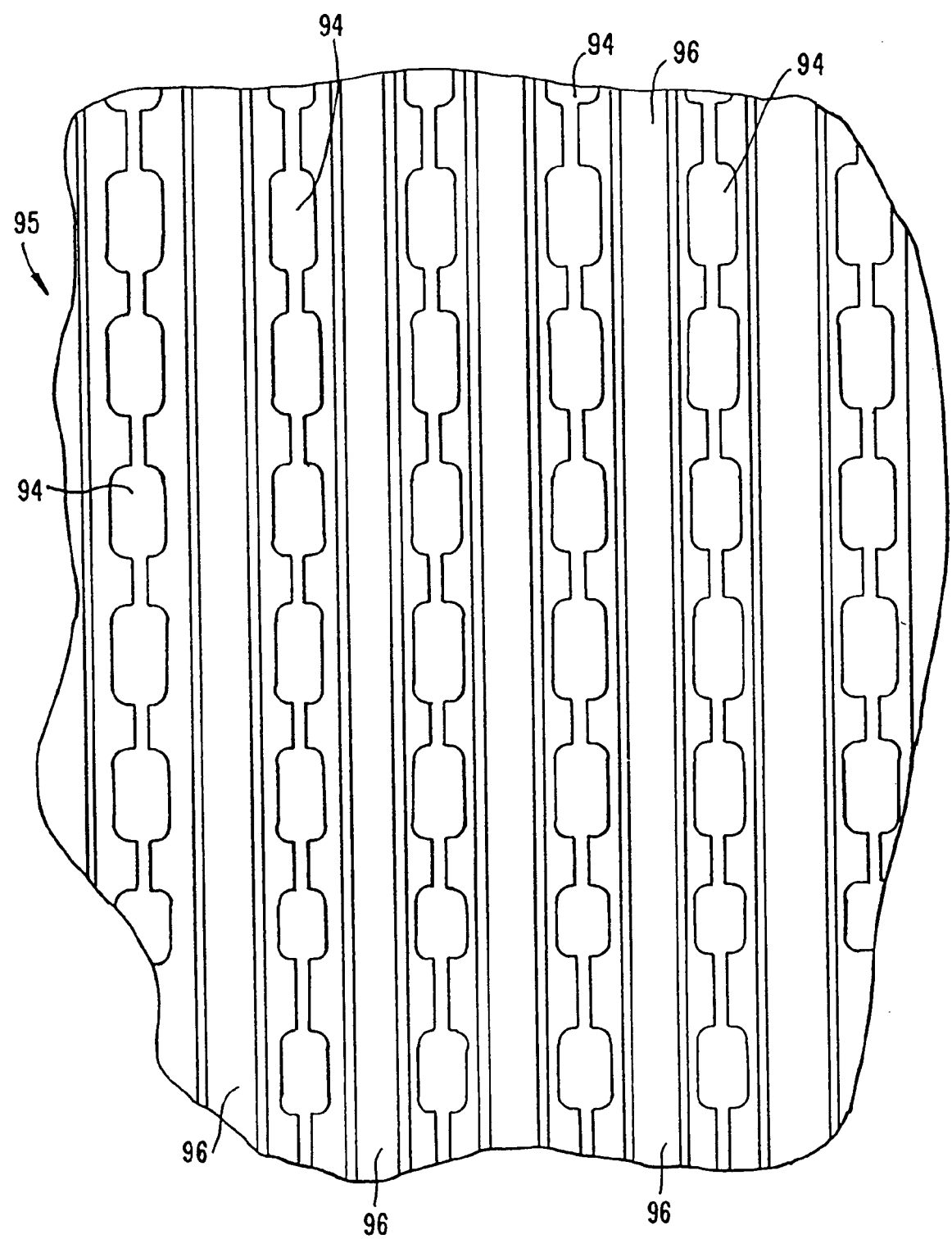

FIG. 31B is a bottom plan view of a control channel layer of a switchable flow array.

Figure 31C:
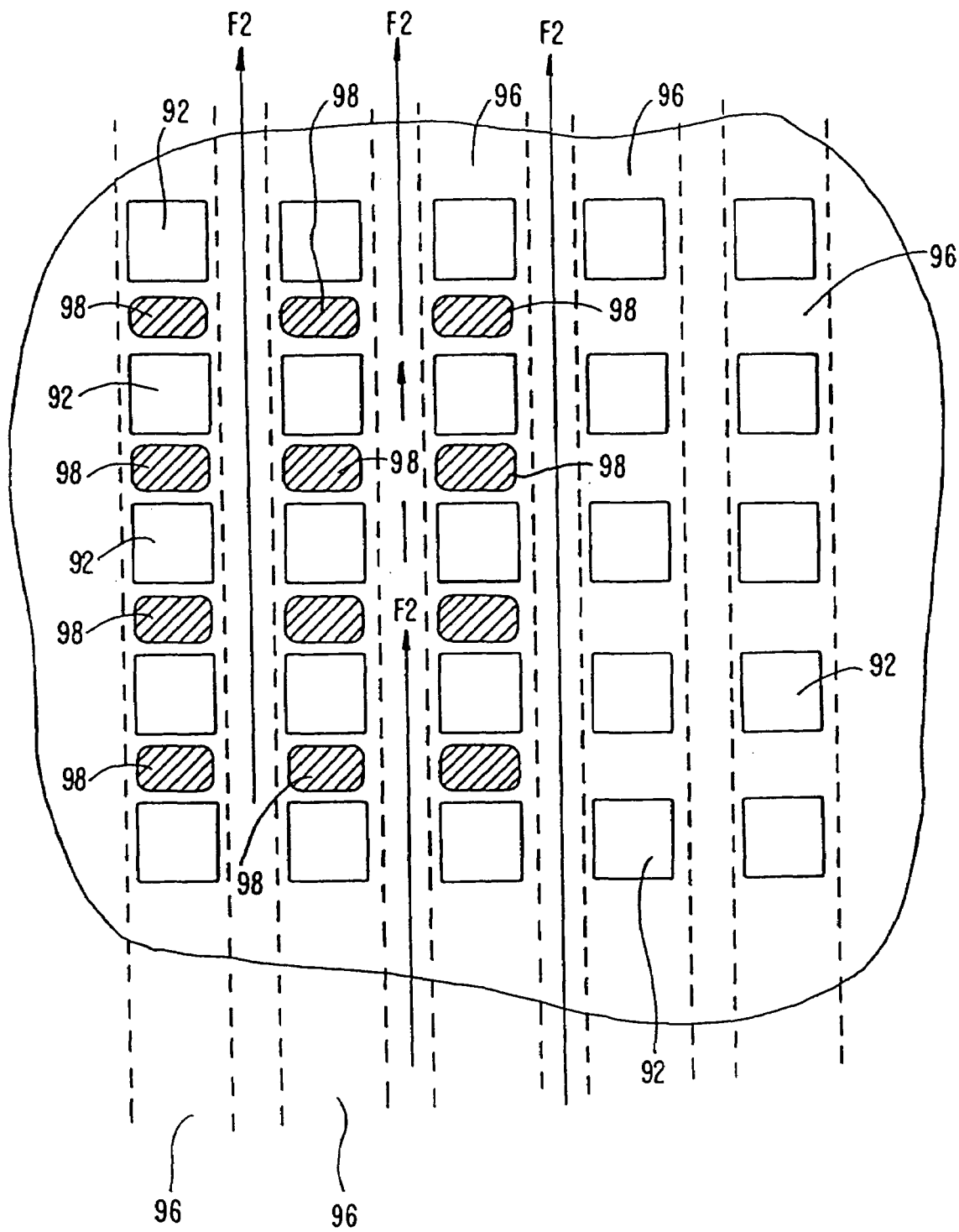

FIG. 31C shows the alignment of the first layer of elastomer of FIG. 31A with one set of control channels in the second layer of elastomer of FIG. 311B.

Figure 31D:
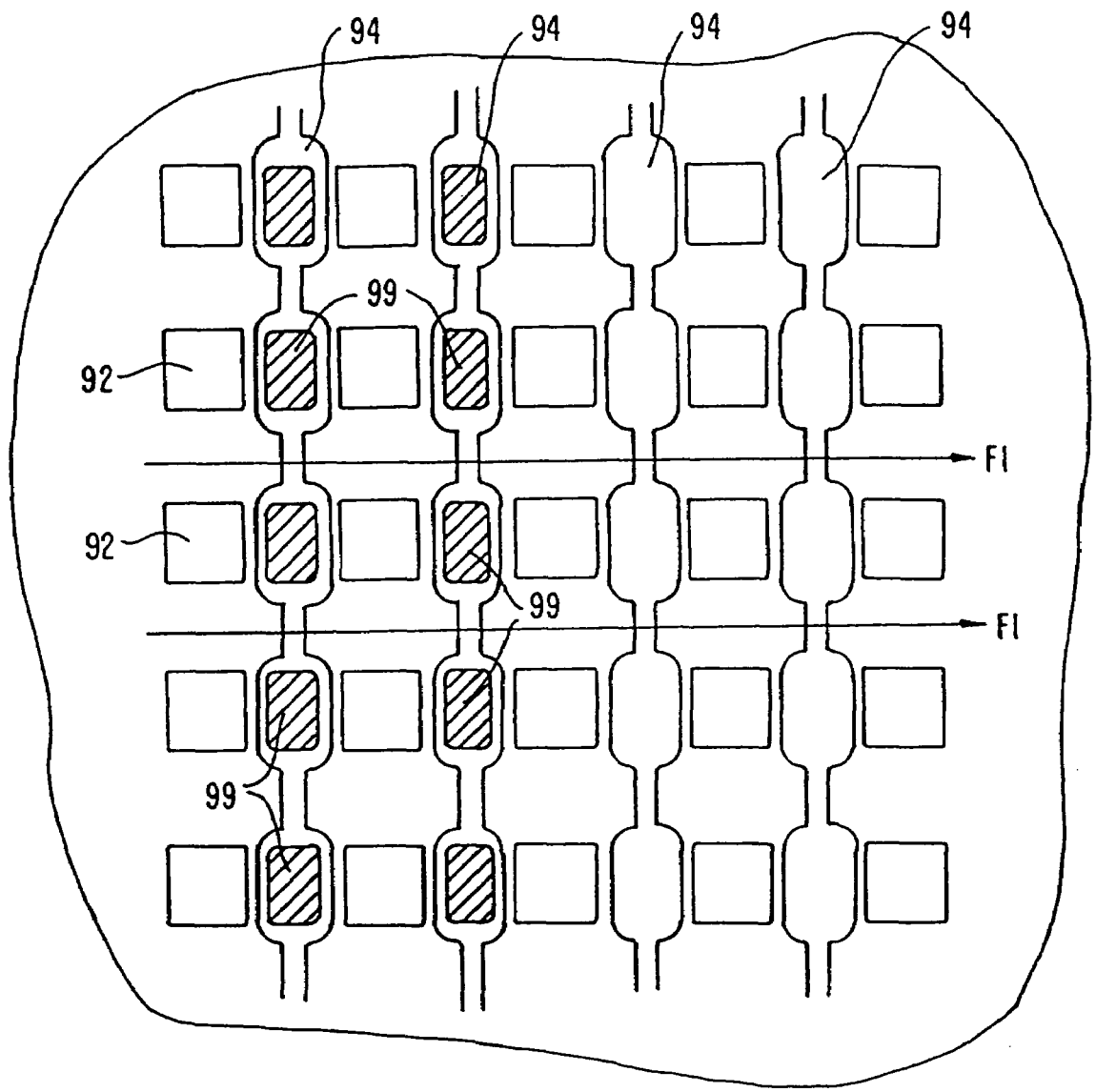

FIG. 31D also shows the alignment of the first layer of elastomer of FIG. 31A with the other set of control channels in the second layer of elastomer of FIG. 31B.

Figure 32:
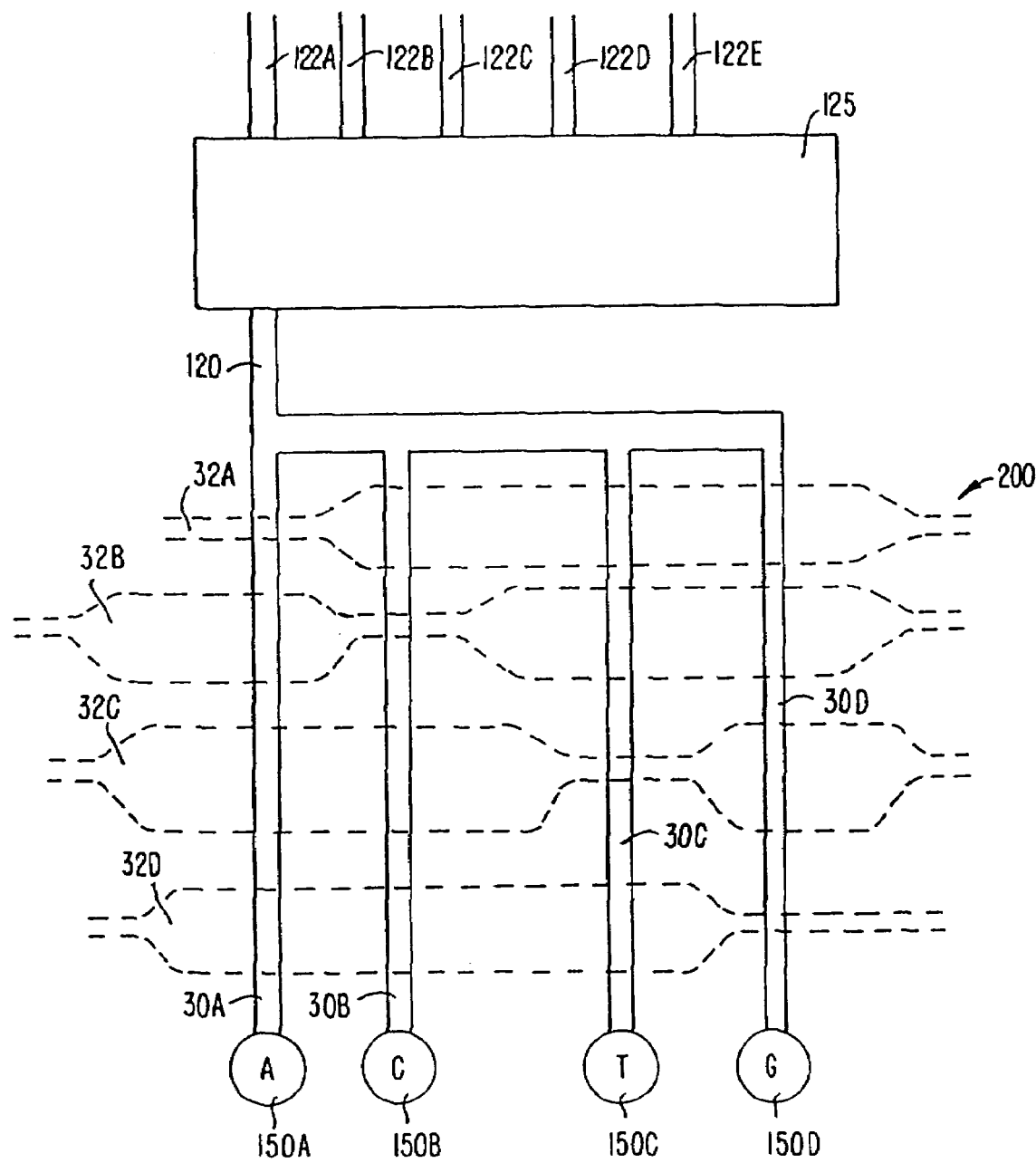

FIG. 32 is a schematic of an integrated system for biopolymer synthesis.

Figure 33:
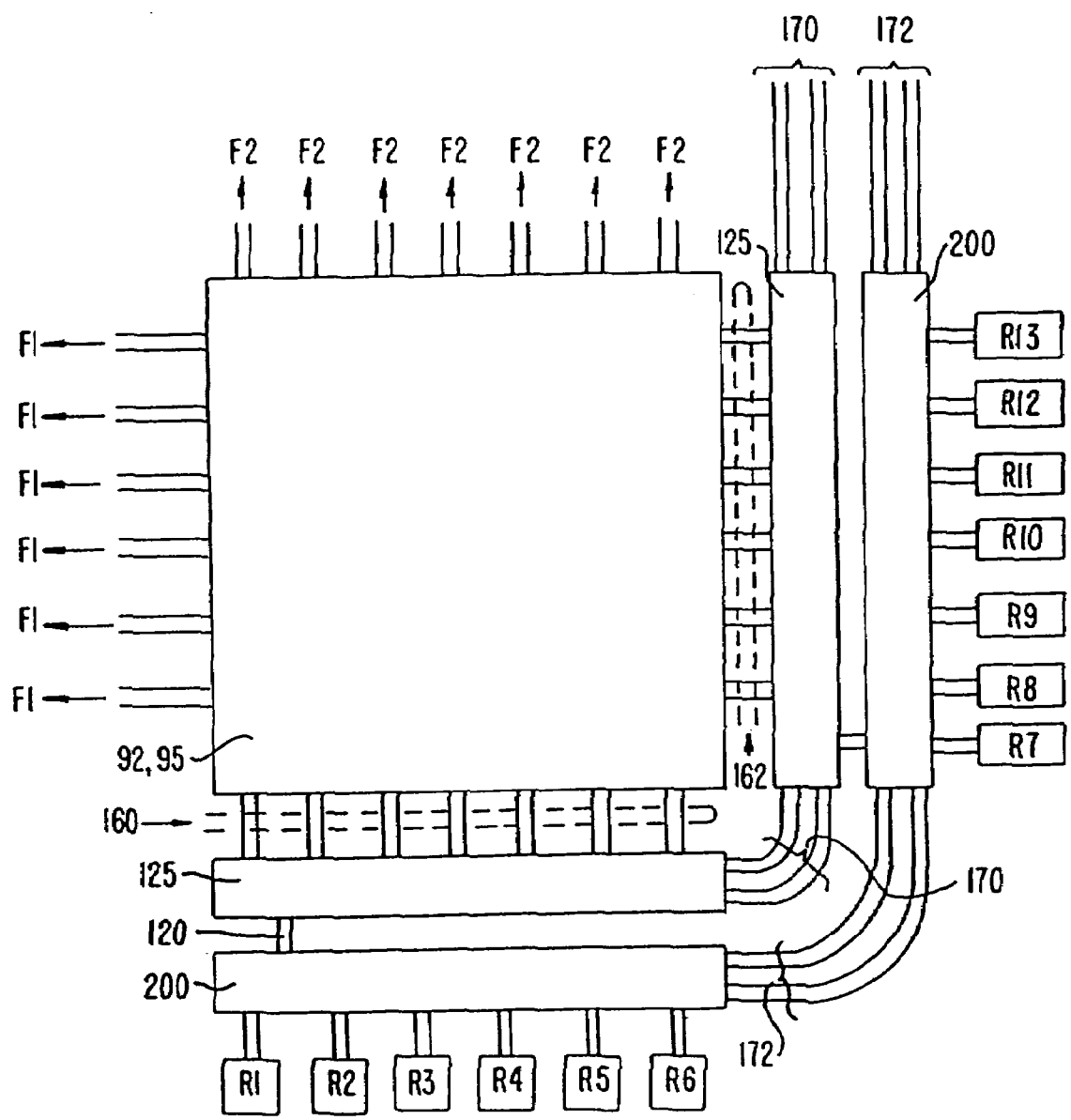

FIG. 33 is a schematic of a further integrated system for biopolymer synthesis.

Figure 34:
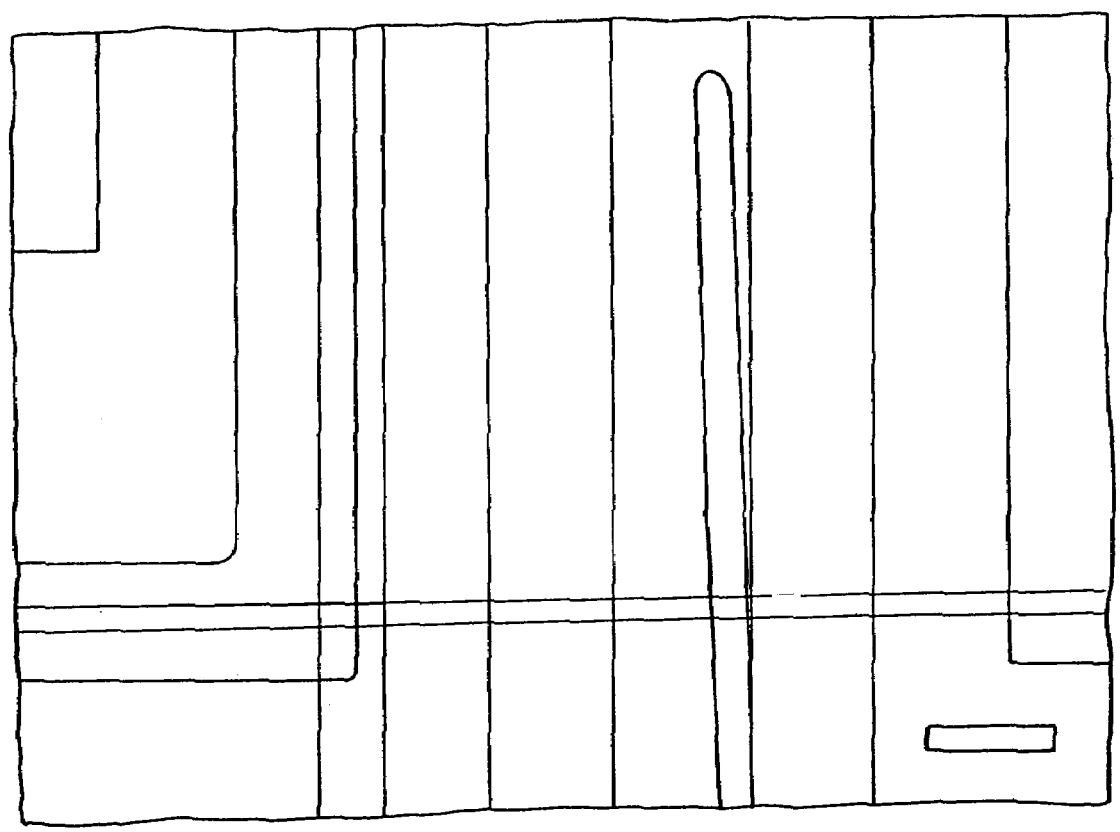

FIG. 34 is an optical micrograph of a section of a test structure having seven layers of elastomer bonded together.

FIGS. 35A-35D show the steps of one embodiment of a method for fabricating an elastomer layer having a vertical via formed therein.

Figure 36:
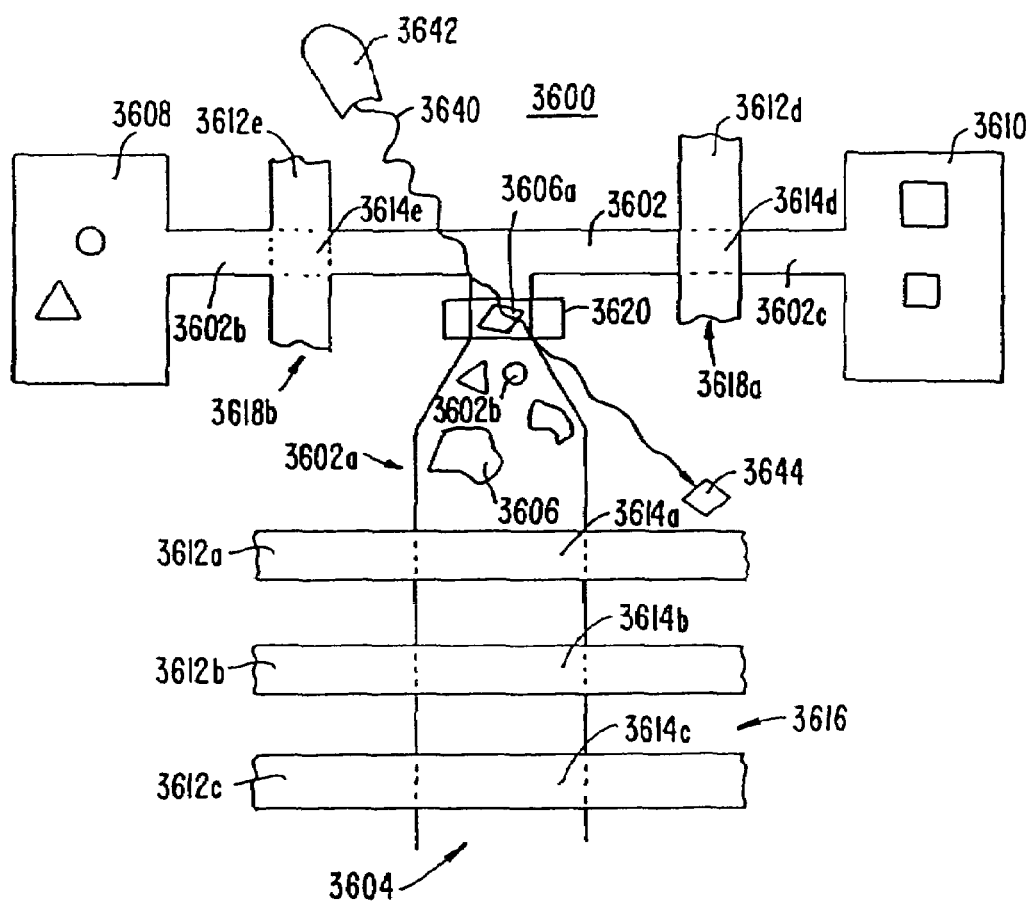

FIG. 36 shows one embodiment of a sorting apparatus in accordance with the present invention.

Figure 37:
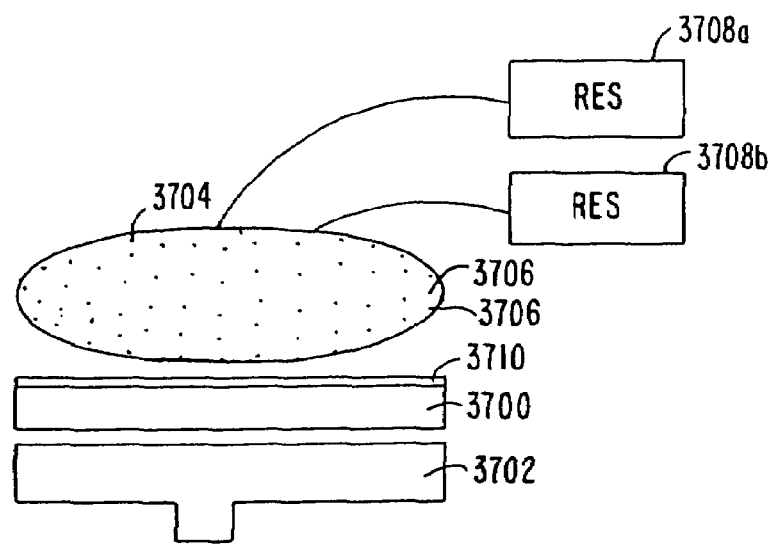

FIG. 37 shows an embodiment of an apparatus for flowing process gases over a semiconductor wafer in accordance with the present invention.

Figure 38A:
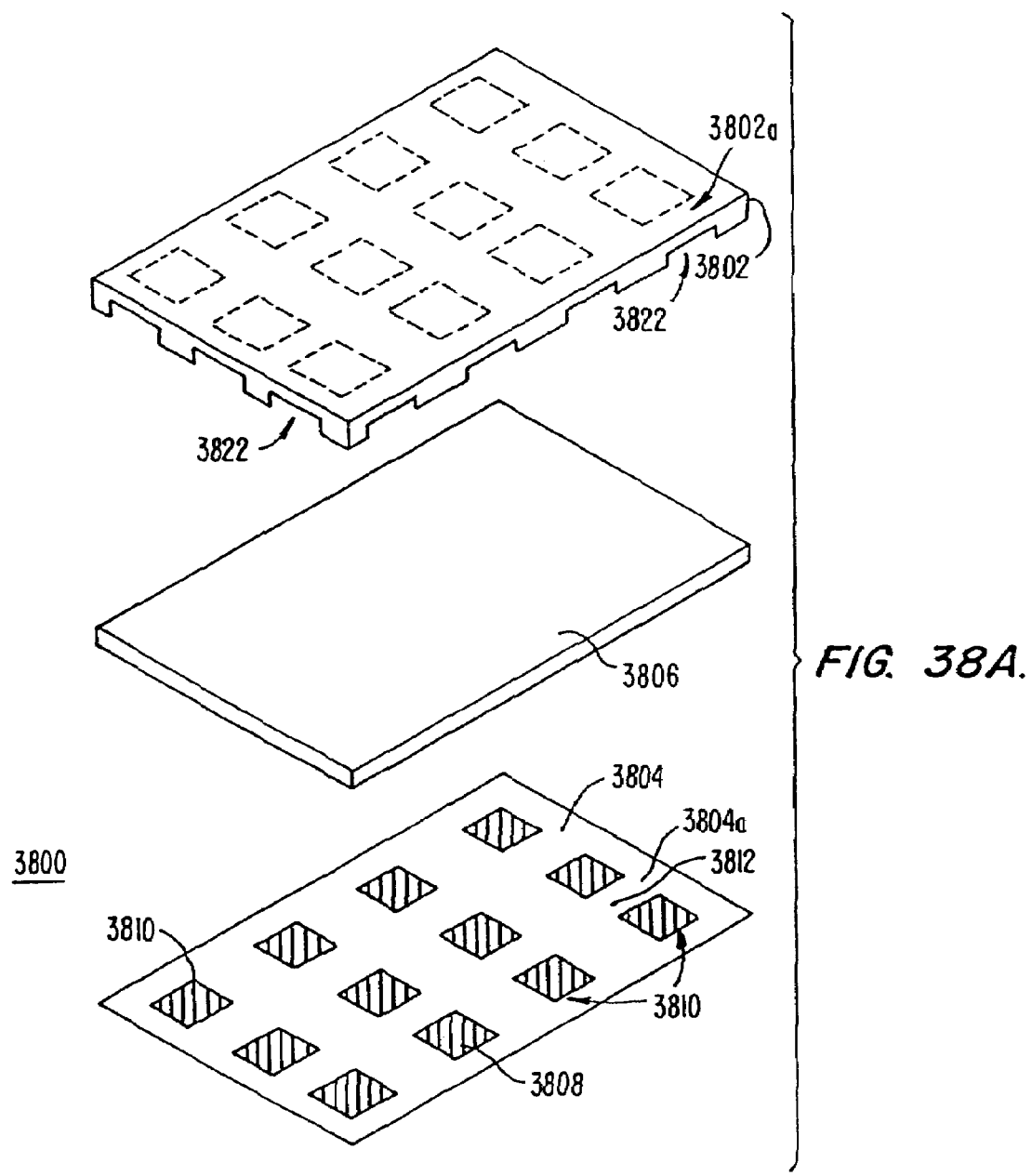

FIG. 38 shows an exploded view of one embodiment of a micro-mirror array structure in accordance with the present invention.

Figure 39:
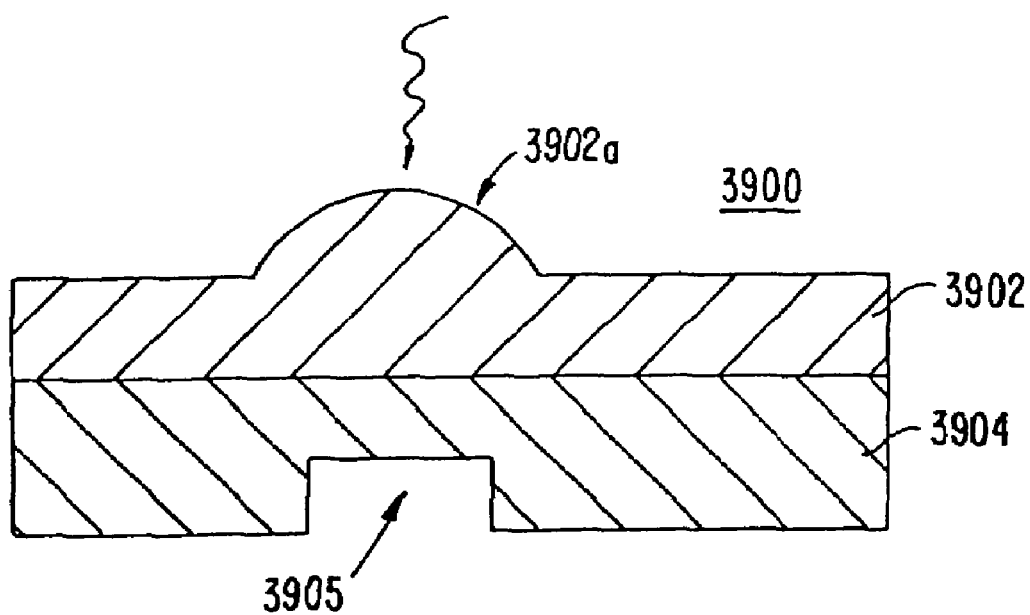

FIG. 39 shows a perspective view of a first embodiment of a refractive device in accordance with the present invention.

Figure 40:
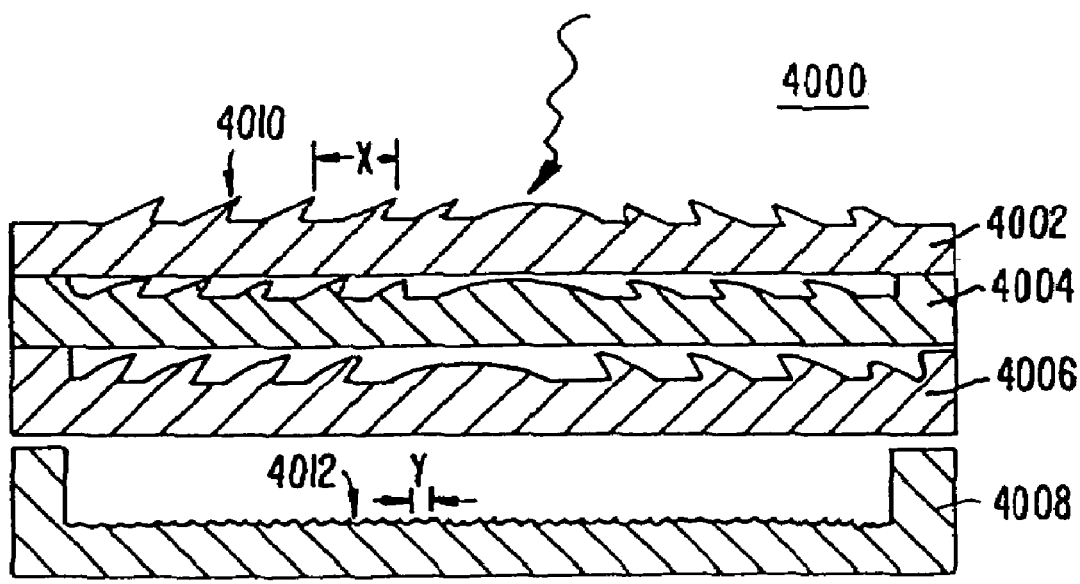

FIG. 40 shows a perspective view of a second embodiment of a refractive device in accordance with the present invention.

Figure 41:
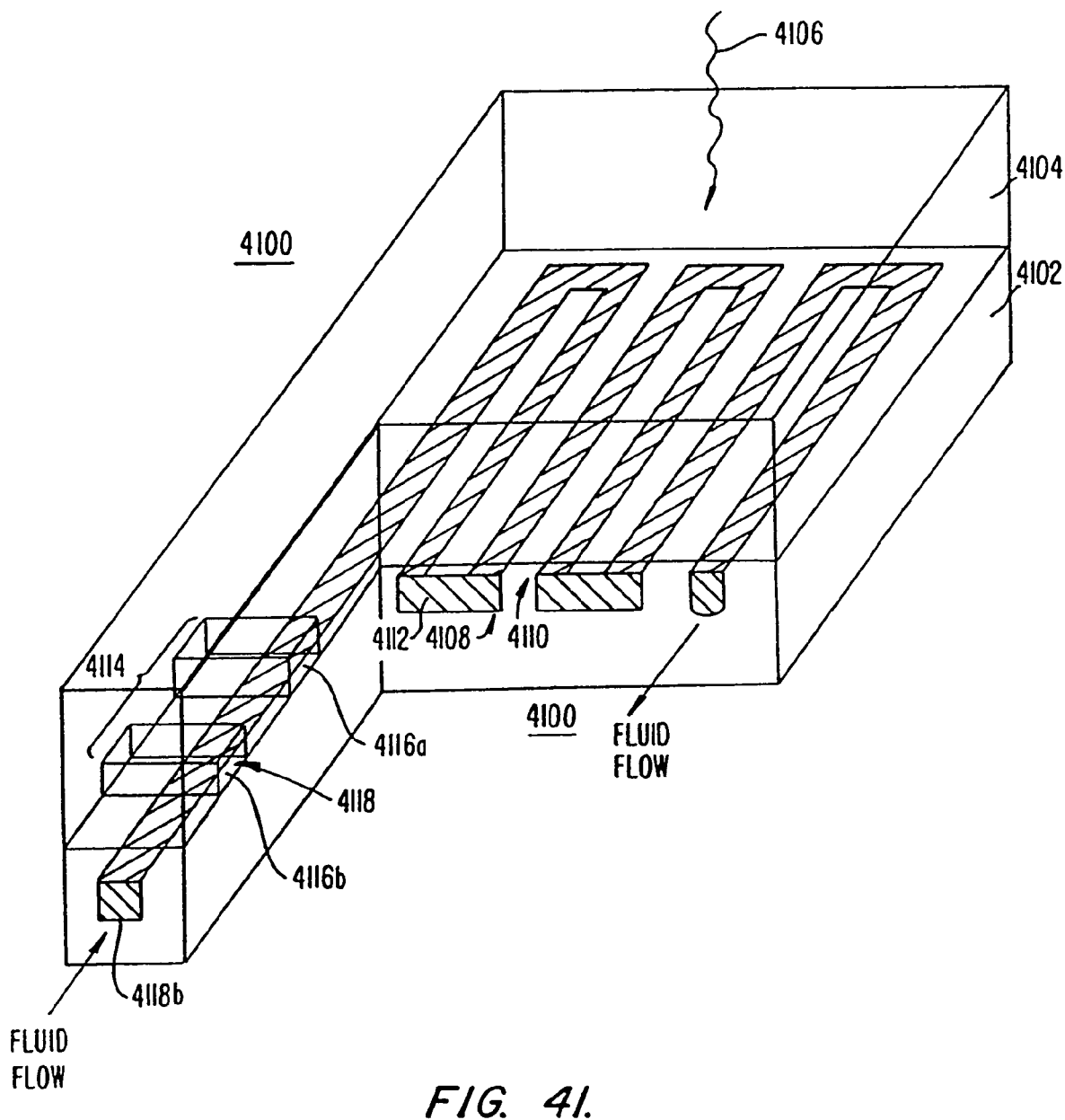

FIG. 41 shows a perspective view of a third embodiment of a refractive device in accordance with the present invention.

FIGS. 42A-42J show views of one embodiment of a normally-closed valve structure in accordance with the present invention.

Figure 43:
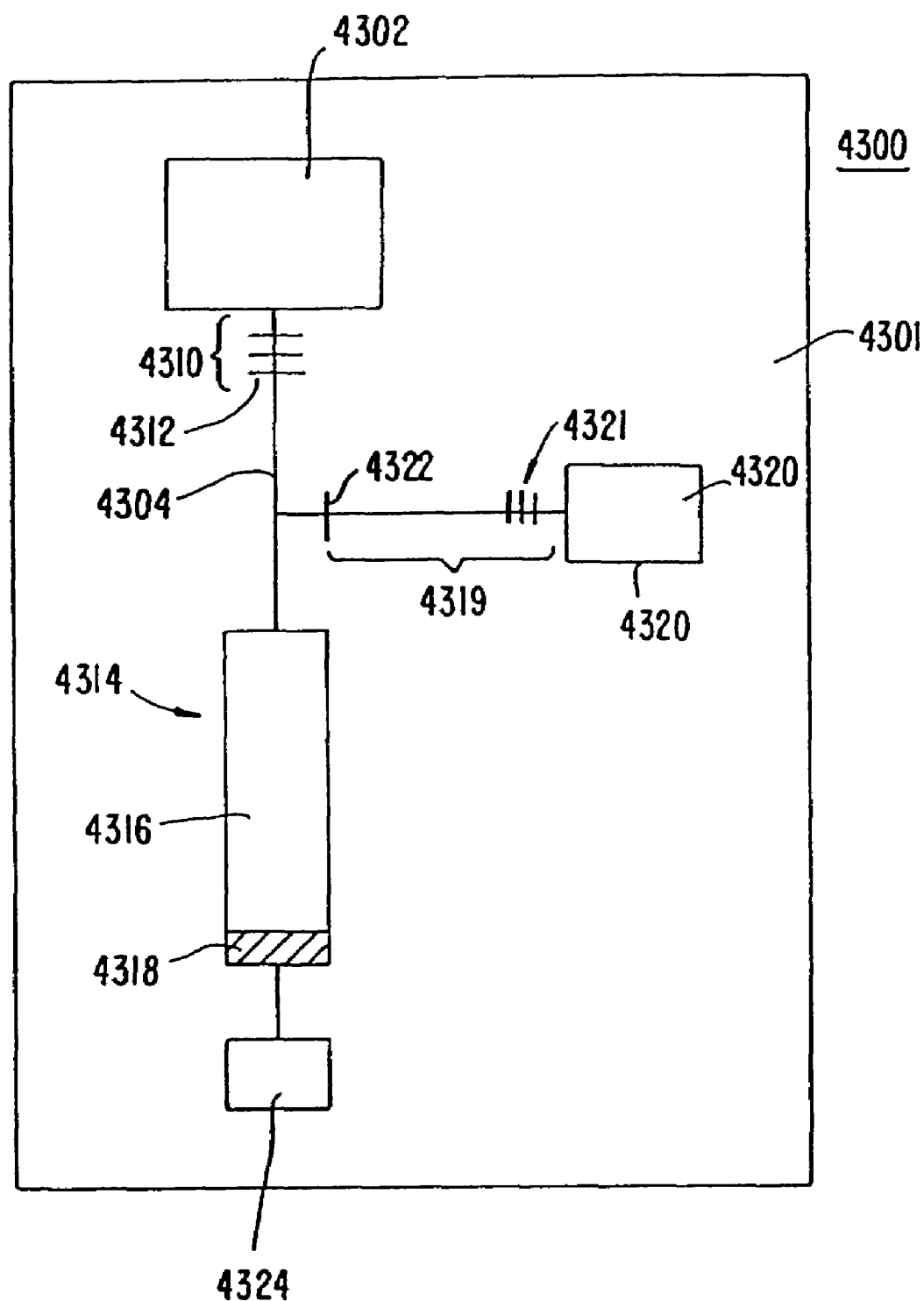

FIG. 43 shows a plan view of one embodiment of a device for performing separations in accordance with the present invention.

FIGS. 44A-44D show plan views illustrating operation of one embodiment of a cell pen structure in accordance with the present invention.

FIGS. 45A-45B show plan and cross-sectional views illustrating operation of one embodiment of a cell cage structure in accordance with the present invention.

FIGS. 46A-46B show cross-sectional views illustrating operation of one embodiment of a cell grinder structure in accordance with the present invention.

Figure 47:
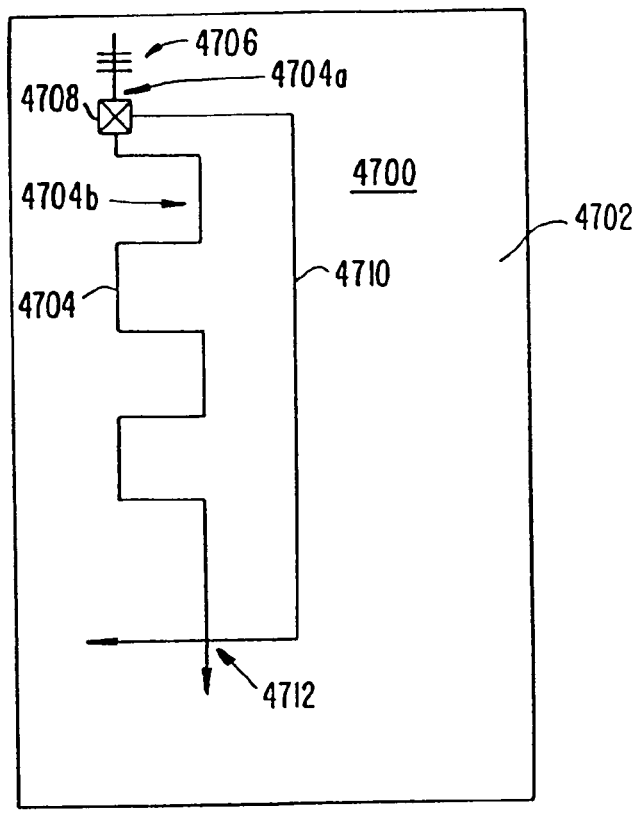

FIG. 47 shows a plan view of one embodiment of a pressure oscillator structure in accordance with the present invention.

Figures 48A, 48B:
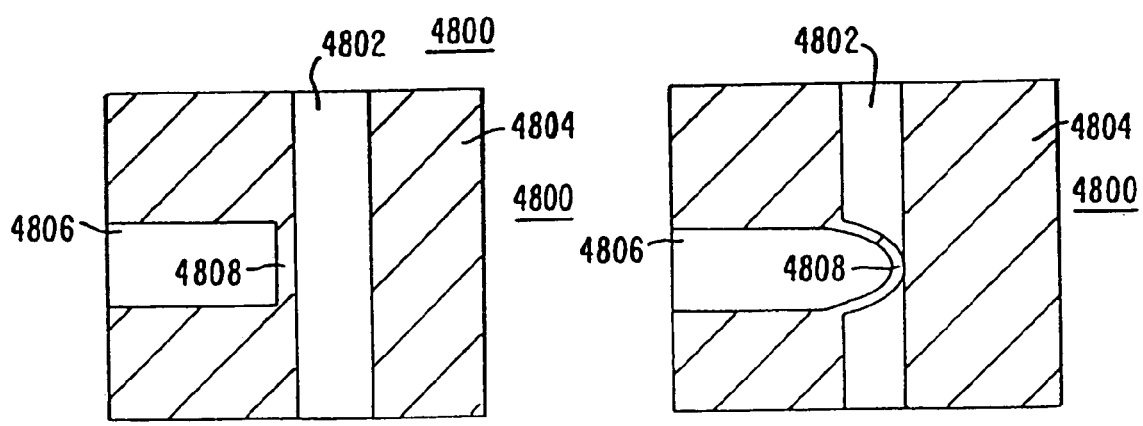

FIGS. 48A and 48B show plan views illustrating operation of one embodiment of a side-actuated valve structure in accordance with the present invention.

Figure 49:
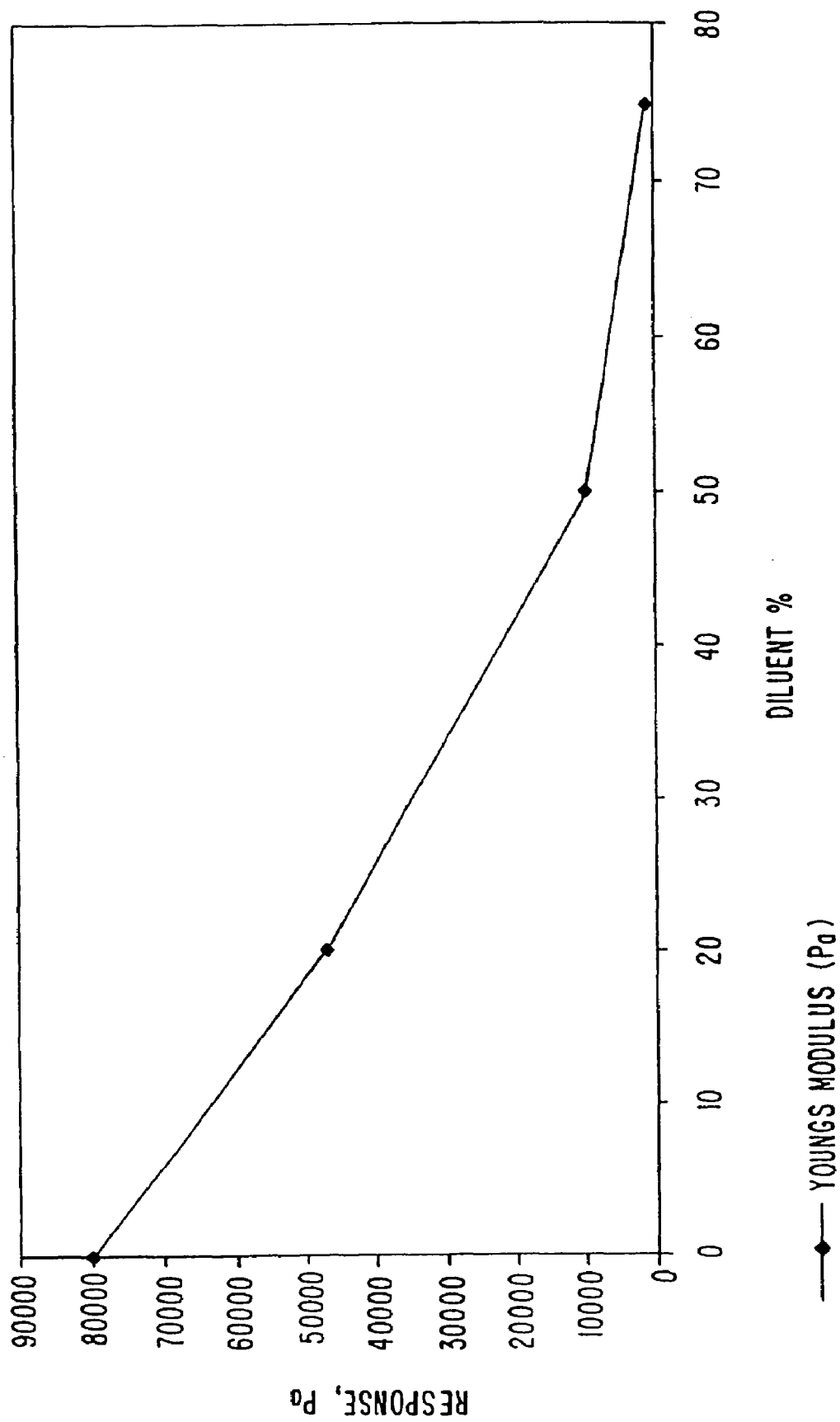

FIG. 49 plots Young's modulus versus percentage dilution of GE RTV 615 elastomer with GE SF96-50 silicone fluid.

FIG. 50 shows a cross-sectional view of a structure in which channel-bearing faces are placed into contact to form a larger-sized channel.

FIG. 51 shows a cross-sectional view of a structure in which non-channel bearing faces are placed into contact and then sandwiched between two substrates.

FIGS. 52A-52C show cross-sectional views of the steps for constructing a bridging structure. FIG. 52D shows a plan view of the bridging structure.

Figure 53:
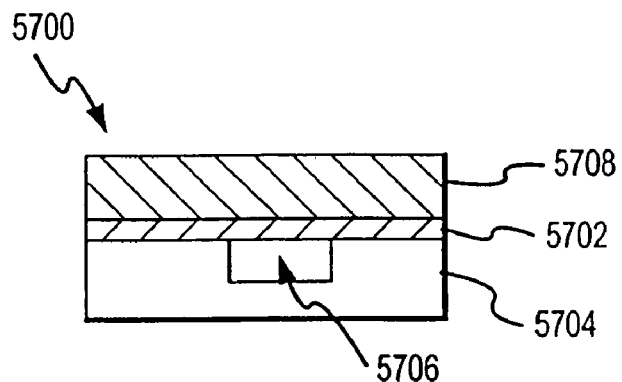

FIGS. 53A-B show a cross-sectional view of embodiments of a composite structure in accordance with the present invention.

Figure 54:
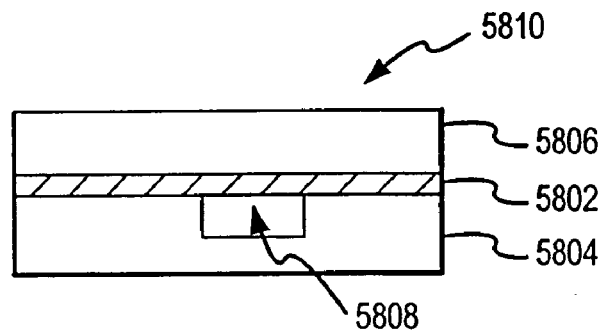

FIG. 54 shows a cross-sectional view of one embodiment of a composite structure in accordance with the present invention.

Figure 55:
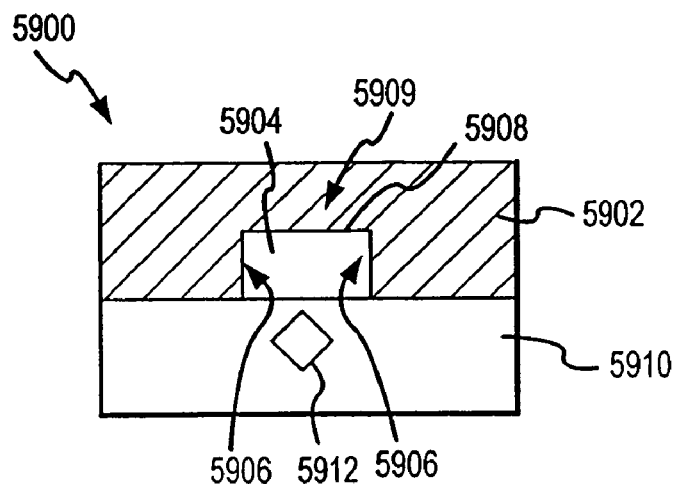

FIGS. 55A-C show cross-sectional views of a process for forming elastomer structures by bonding along a vertical line.

FIG. 56 shows a schematic view of an electrolytically-actuated syringe structure in accordance with one embodiment of the present invention.

FIGS. 57A-57C illustrate cross-sectional views of a process for forming a flow channel having a membrane positioned therein.

FIGS. 58A-58D illustrate cross-sectional views of metering by volume exclusion in accordance with an embodiment of the present invention.

Figure 59C:
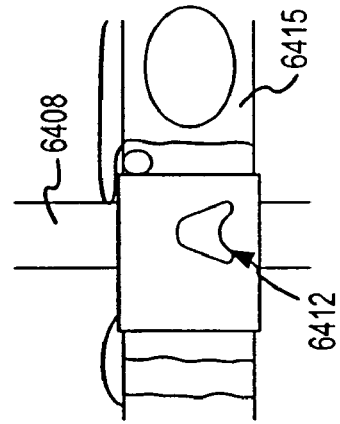
Figure 59D:
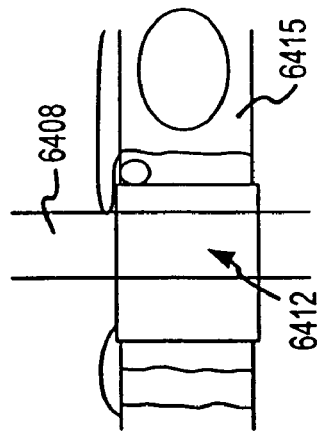
Figure 59A:
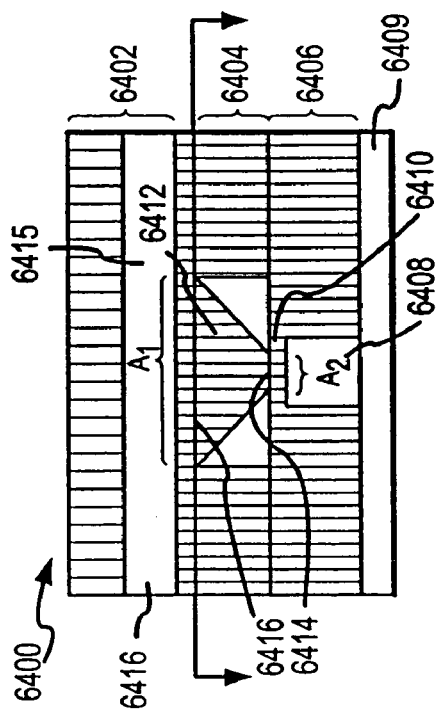
Figure 59B:
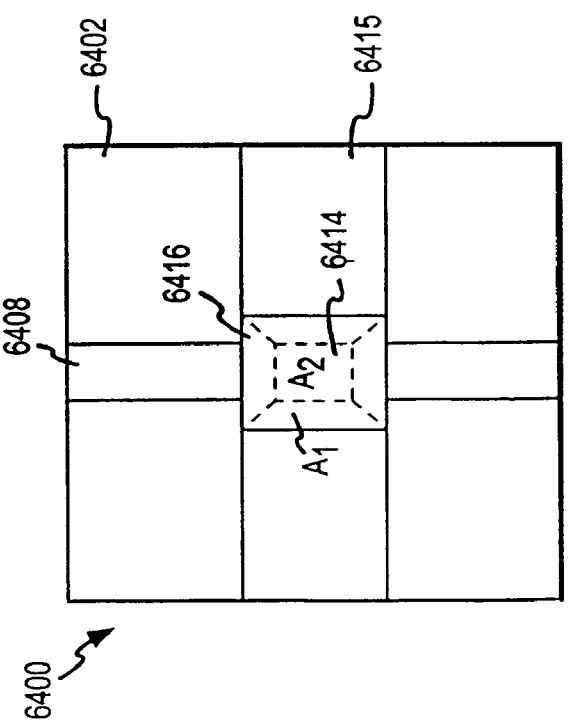

FIGS. 59A-59B show cross-sectional and plan views respectively, of an embodiment of a linear amplifier constructed utilizing microfabrication techniques in accordance with the present invention.

FIGS. 59C-59D show photographs of a linear amplifier in open and closed positions, respectively.

Figure 60:
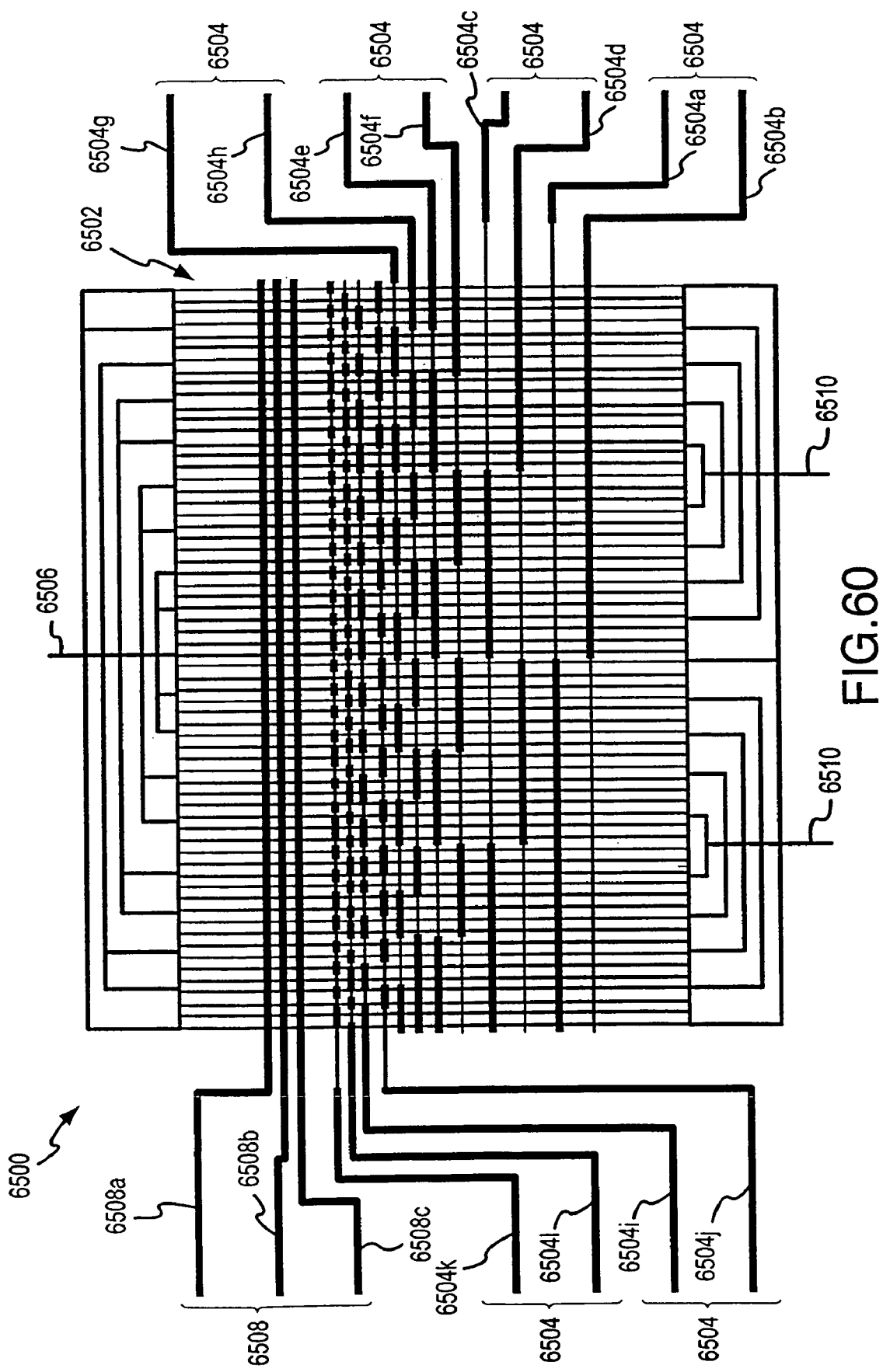

FIG. 60 shows a plan view of an embodiment of a large multiplexer structure in accordance with the present invention.

Figure 61A:
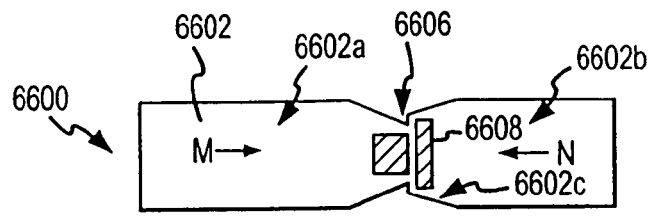
Figure 61B:
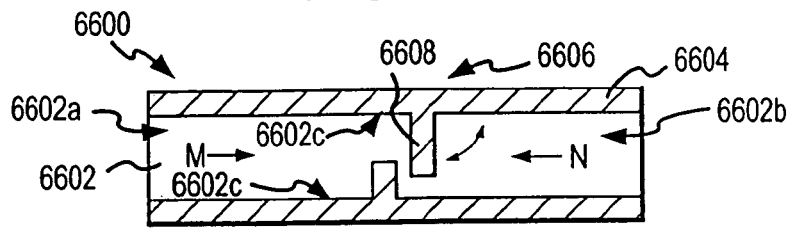

FIGS. 61A-61B show plan and cross-sectional views, respectively, of an embodiment of a one-way valve structure in accordance with the present invention.

FIGS. 62A-62E slow cross-sectional views of steps of an embodiment of a process for forming a one-way valve in accordance with the present invention.

Figure 63:
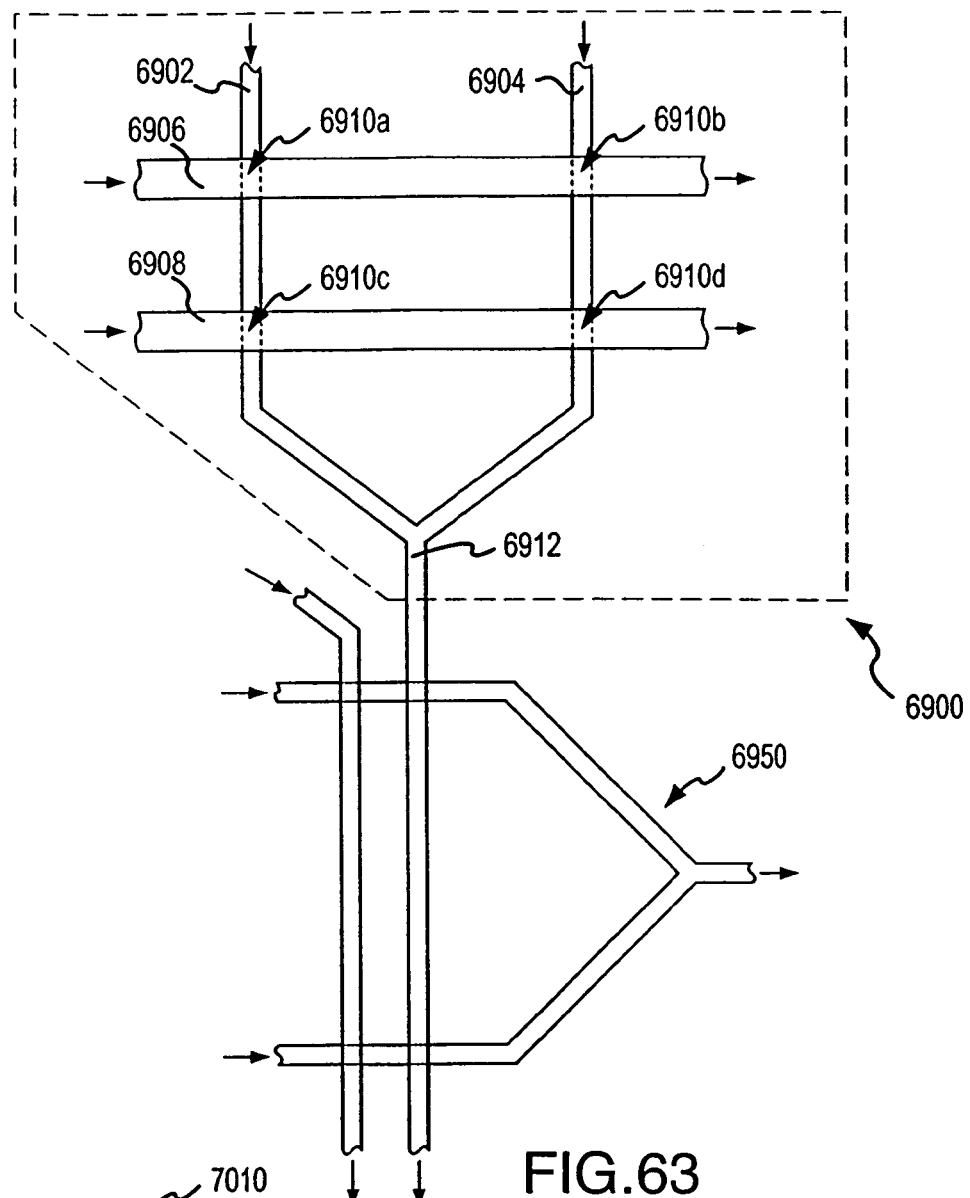

FIG. 63 is an embodiment of a NOR gate logic structure in accordance with the present invention.

Figure 64:
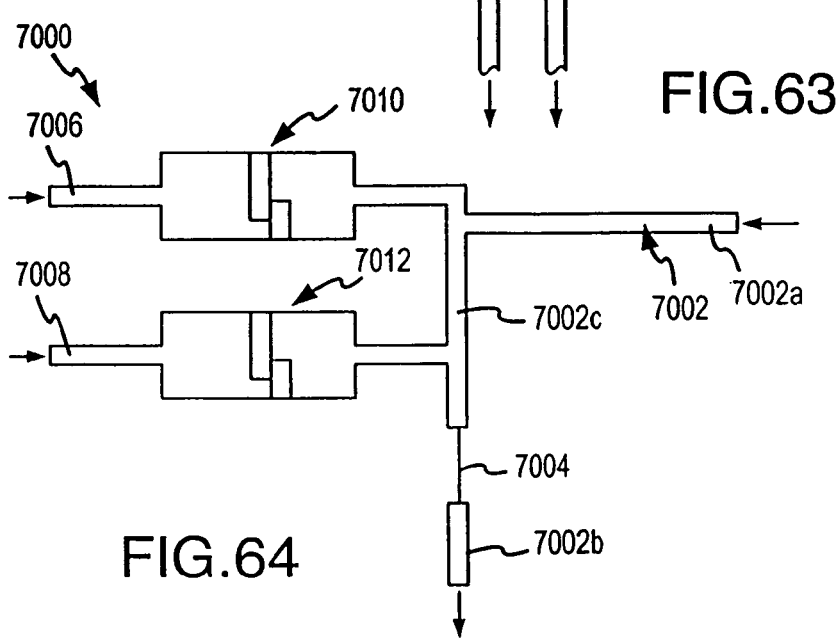

FIG. 64 is an embodiment of an AND gate logic structure in accordance with the present invention which utilizes one way valve structures.

Figure 65:
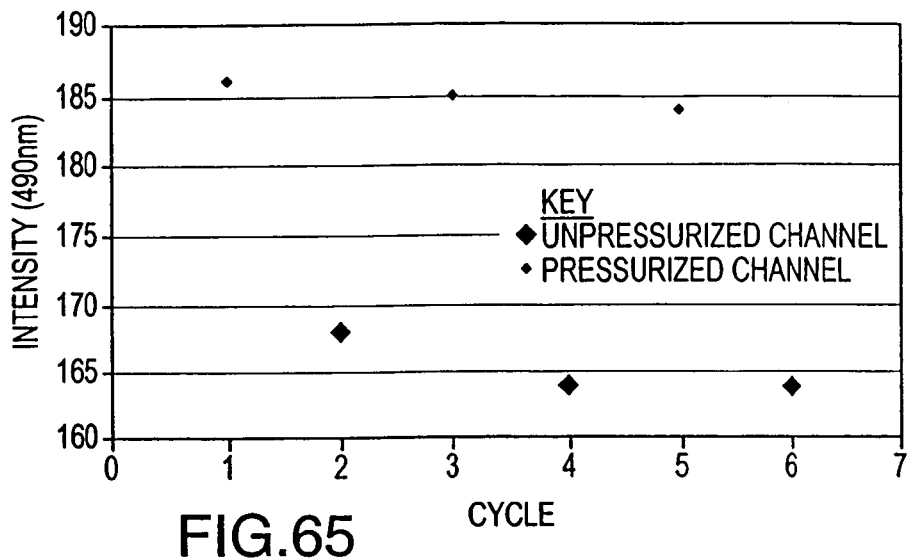

FIG. 65 plots light intensity versus cycle for an embodiment of a Bragg mirror structure in accordance with the present invention.

Figure 66:
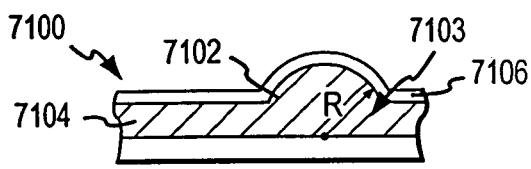

FIG. 66 is a cross-sectional view of an embodiment of a tunable microlens structure in accordance with an embodiment of the present invention.

Figure 67:
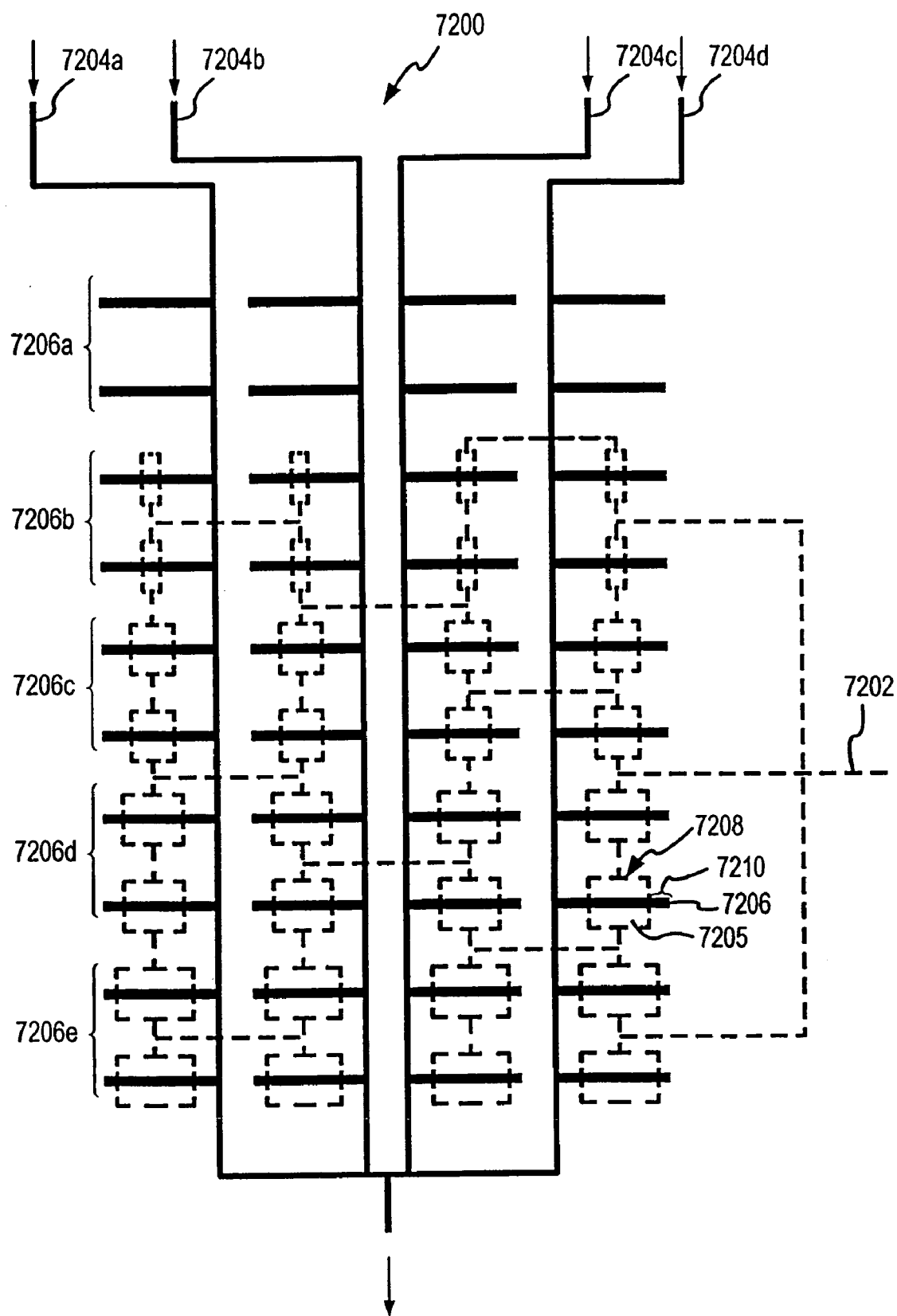

FIG. 67 is a plan view of a protein crystallization system in accordance with one embodiment of the present invention.

Figure 68A:
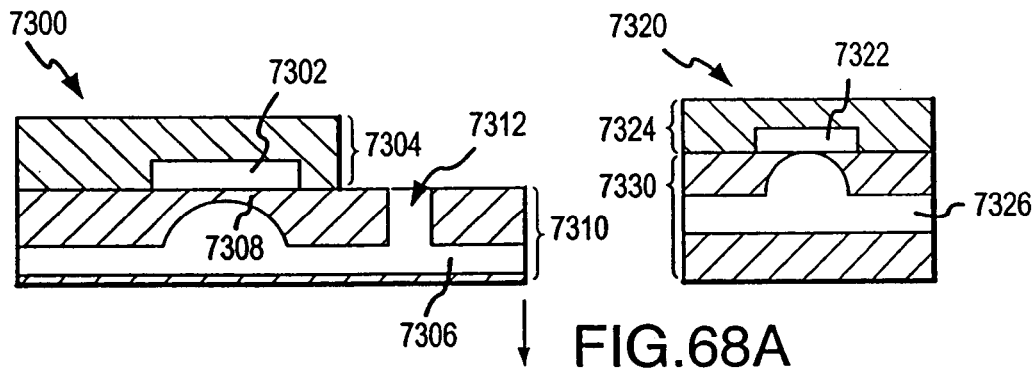
Figure 68B:
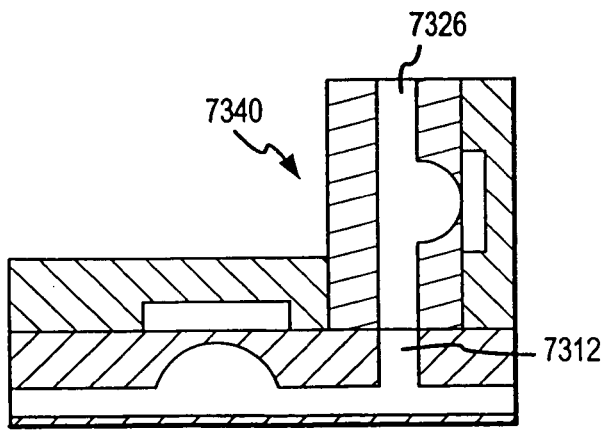

FIG. 68A-68B are cross-sectional views of a method for bonding a vertically-oriented microfabricated elastomer structure to a horizontally-oriented microfabricated elastomer structure.

Figure 69A:
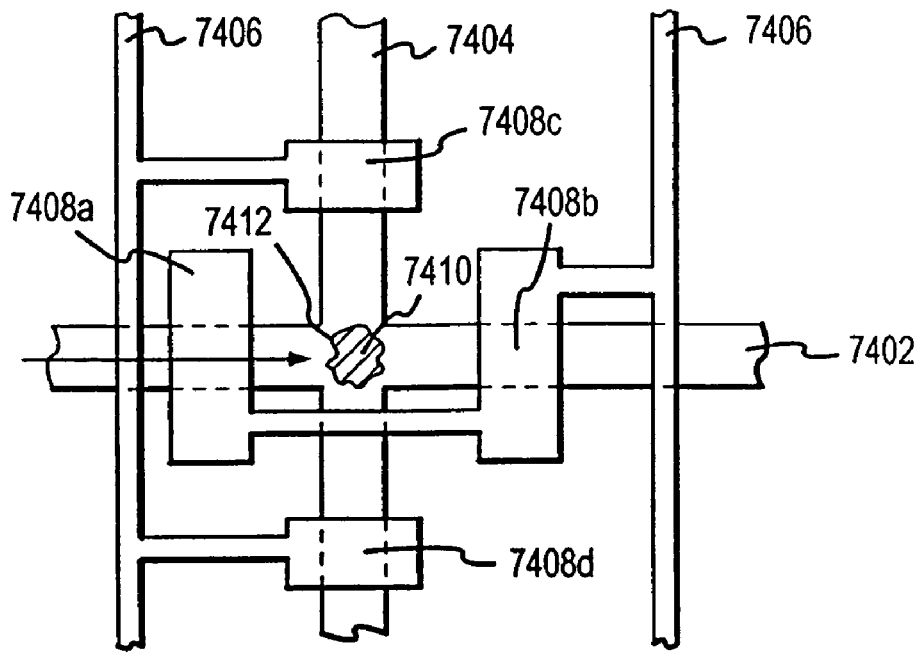
Figure 69B:
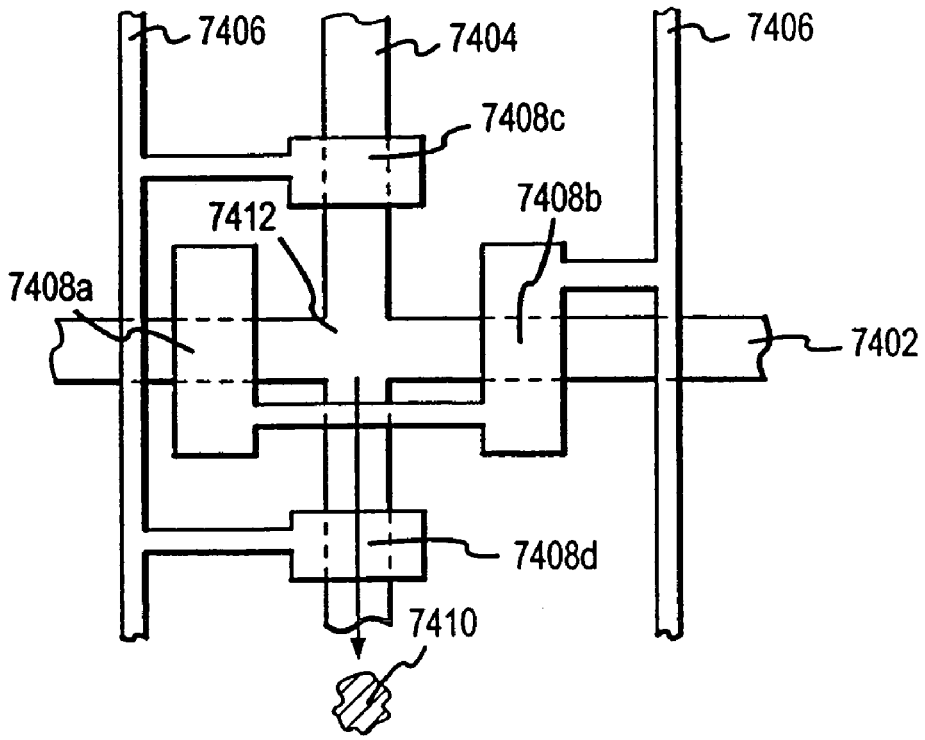

FIGS. 69A-B, illustrate a plan view of mixing steps performed by a microfabricated structure in accordance another embodiment of the present invention.

Figure 70:
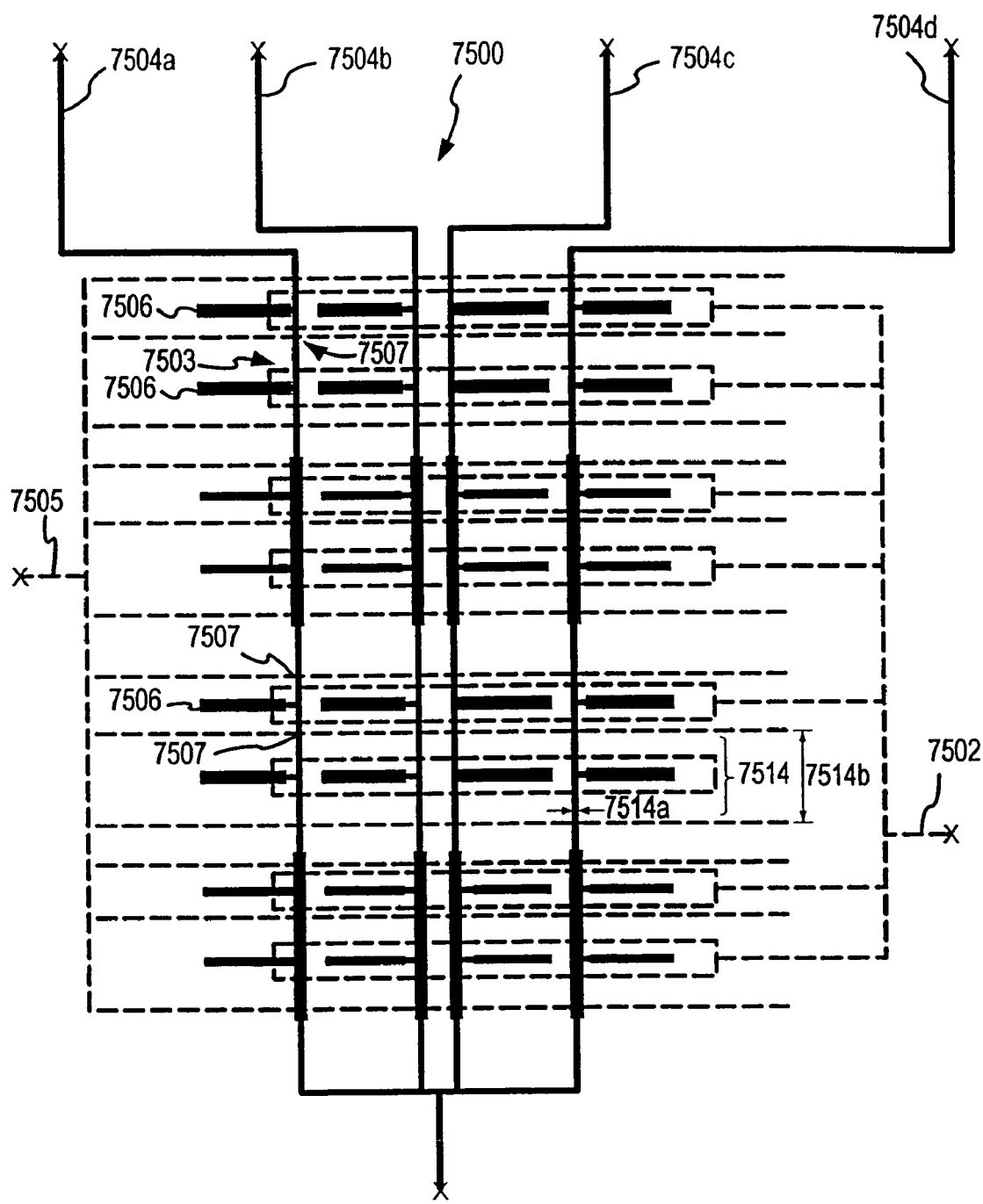

FIG. 70 is a plan view of a protein crystallization system in accordance with an alternative embodiment of the present invention.

Figure 71A:
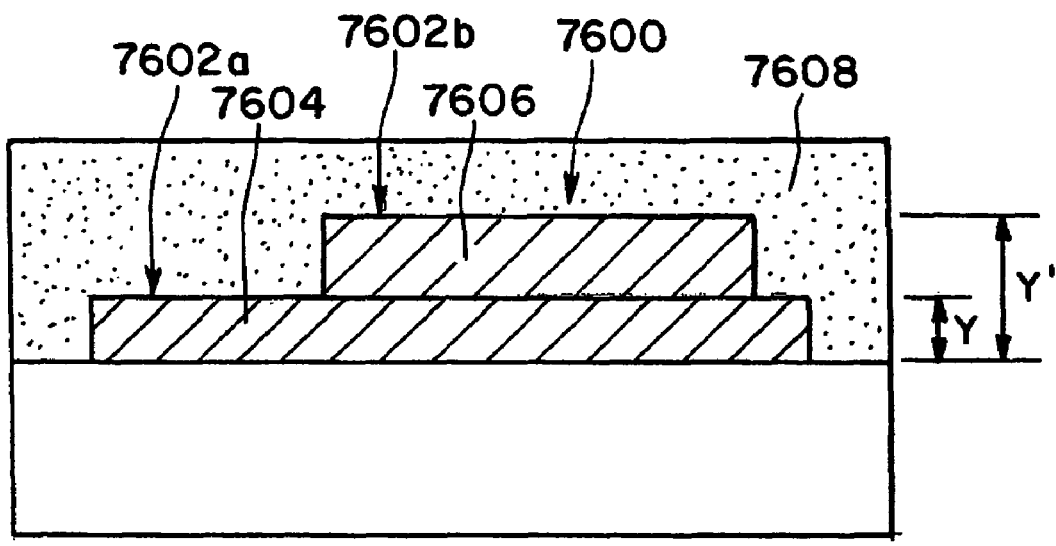

FIG. 71A shows a cross-sectional view of a mold featuring topographic features of differing heights.

Figure 71B:
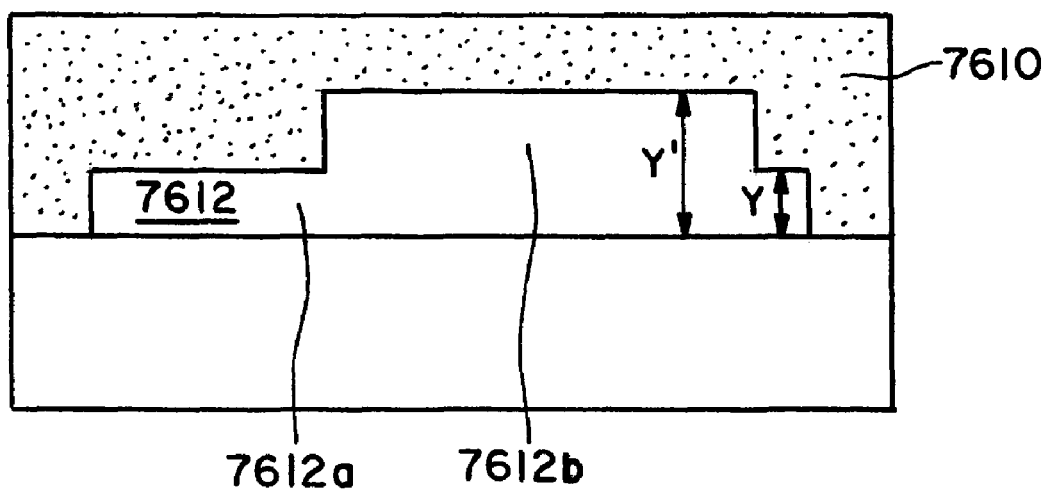

FIG. 71B shows a cross-sectional view of an elastomer layer patterned utilizing the mold of FIG. 71A.

FIG. 72 shows a cross-sectional view of an alternative embodiment of a valve structure.

Figure 73A:
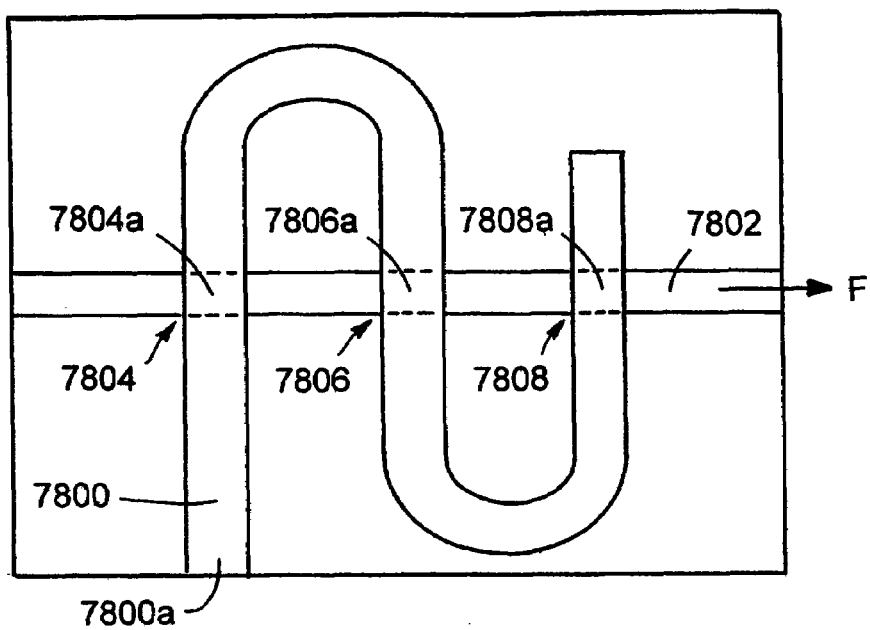

FIG. 73A presents a plan view of an alternative embodiment of a pump structure in accordance with the present invention.

Figure 73B:
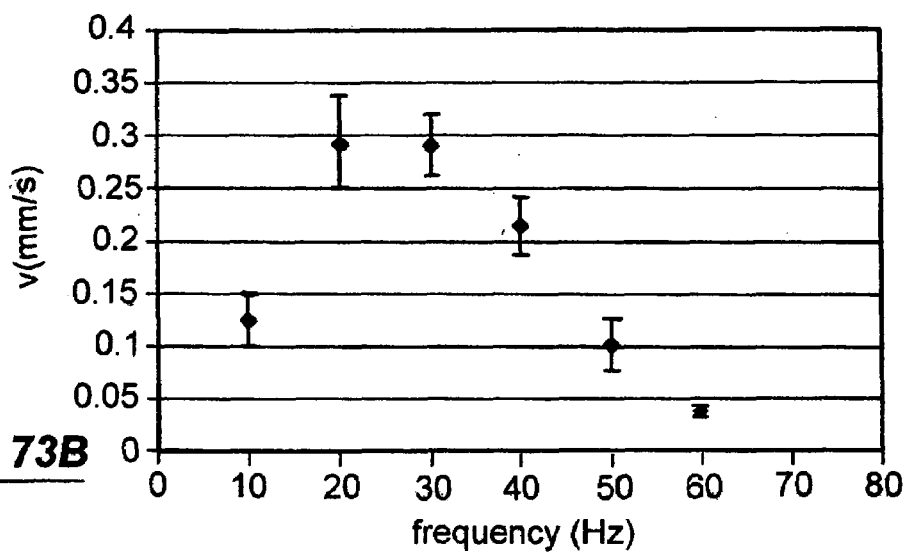
Figure 73C:
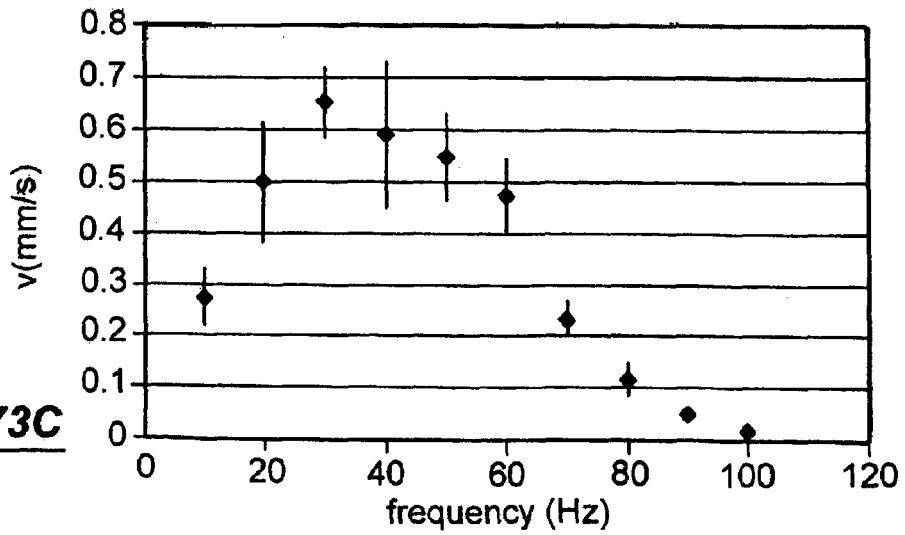

FIGS. 73B and 73C plot flow velocity versus frequency of application of high pressure signal to the control line of a pump structure of FIG. 73A FIG. 74 shows a plan view of multiplexer structure.

FIG. 75 presents a cross-sectional view of a microfluidic structure in accordance with one embodiment of the present invention, which is formed from three elastomer layers on top of a substrate.

FIG. 76 shows a cross-sectional view of a pinch-off valve in accordance with an embodiment of the present invention.

Figure 77:
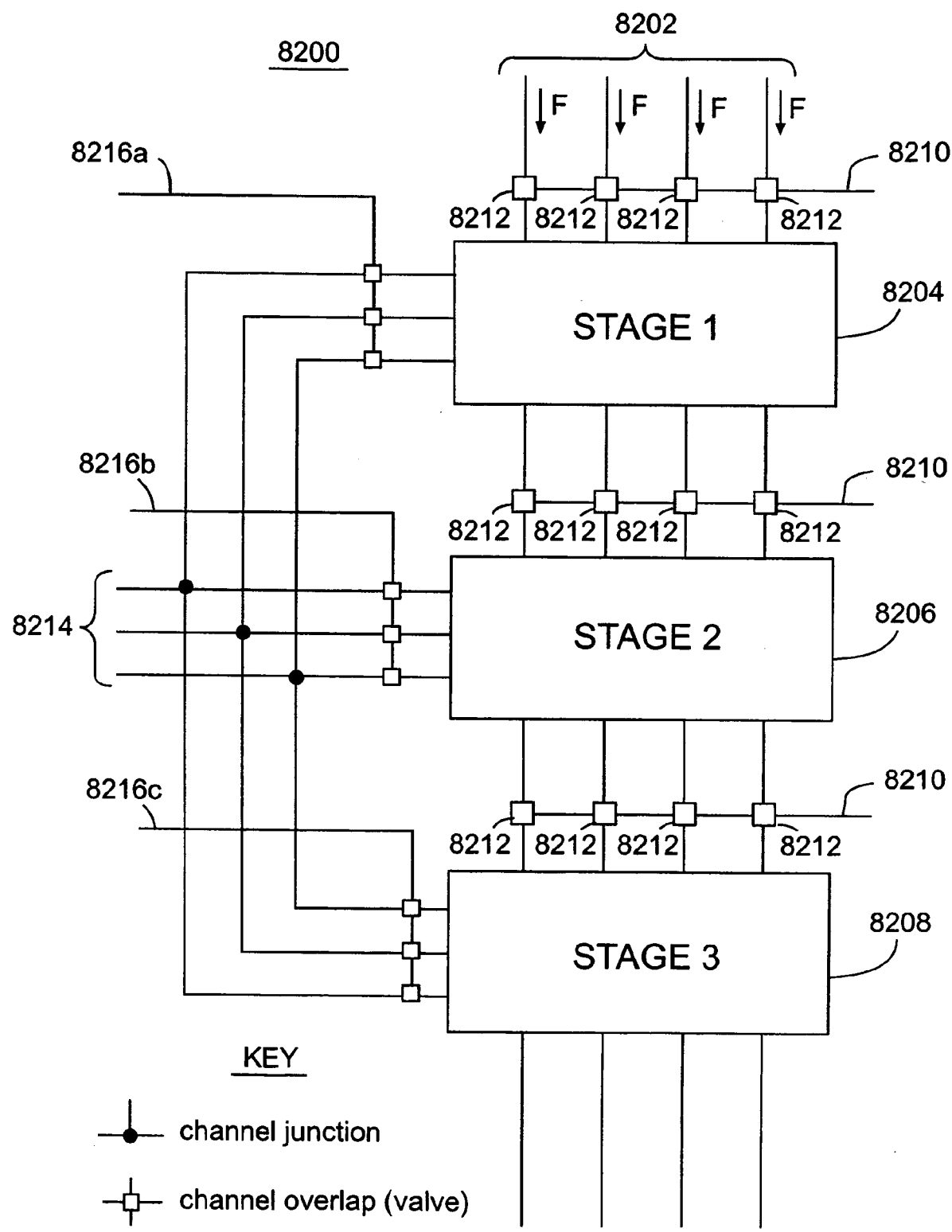

FIG. 77 illustrates an embodiment of a multi-layer microfabricated elastomeric structure having two layers of control channels positioned on the same side of the flow channel.

Figure 78:
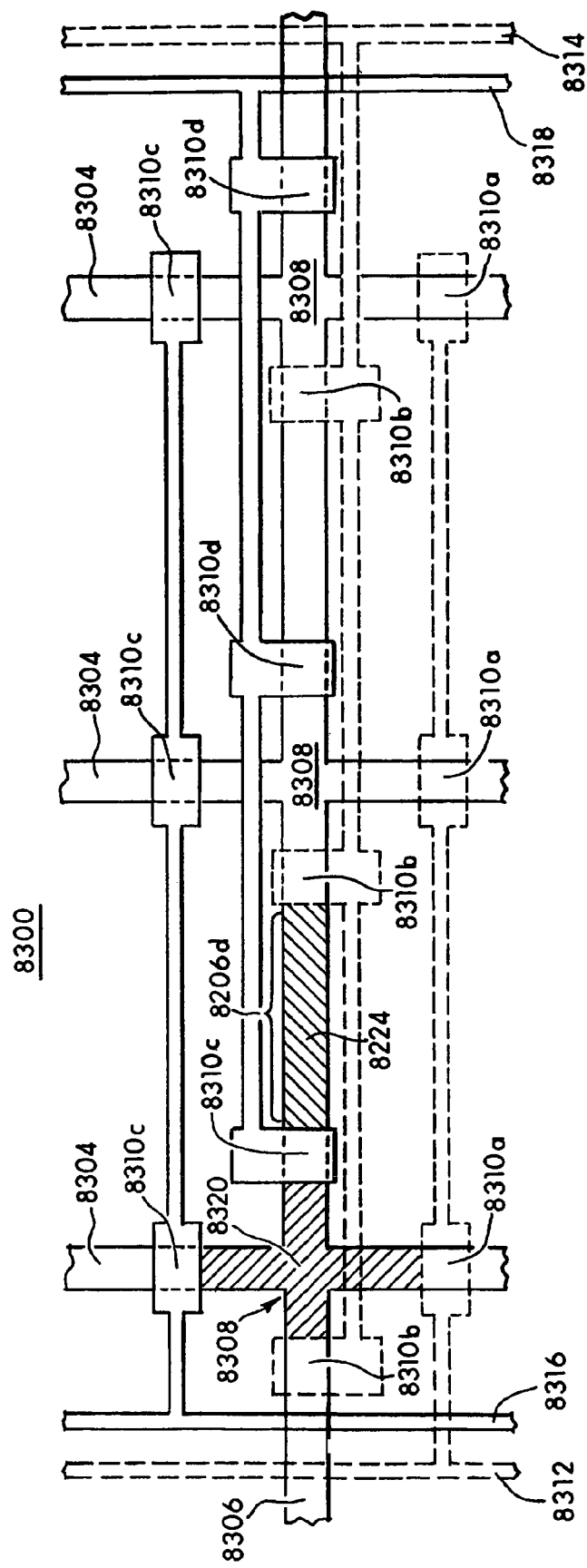

FIG. 78 shows a plan view of a row of a flow channel array featuring independently-controllable valves.

Figure 79:
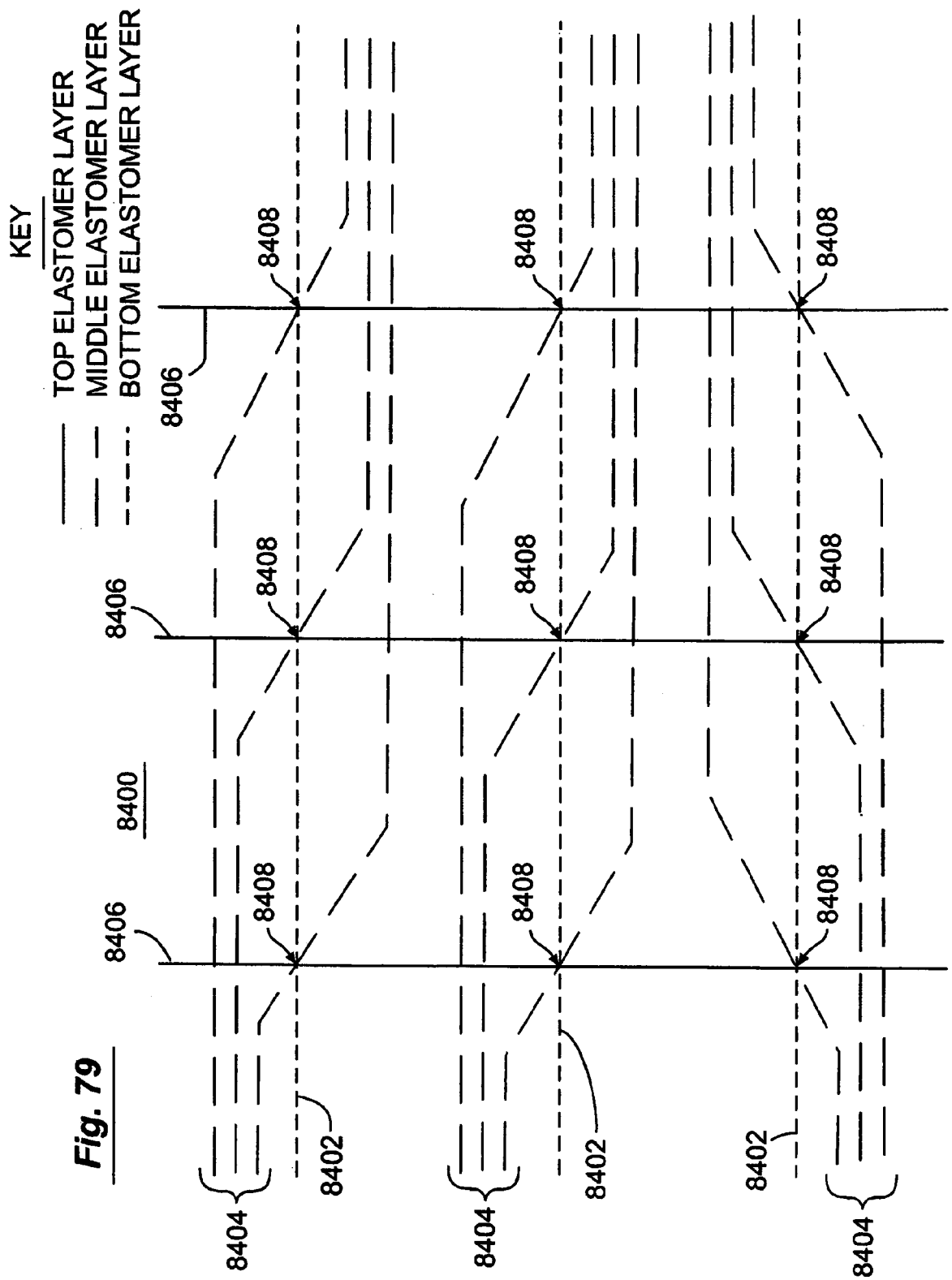

FIG. 79 illustrates a plan view of an alternative embodiment of a multiplexer structure in accordance with the present invention.

Figure 80A:
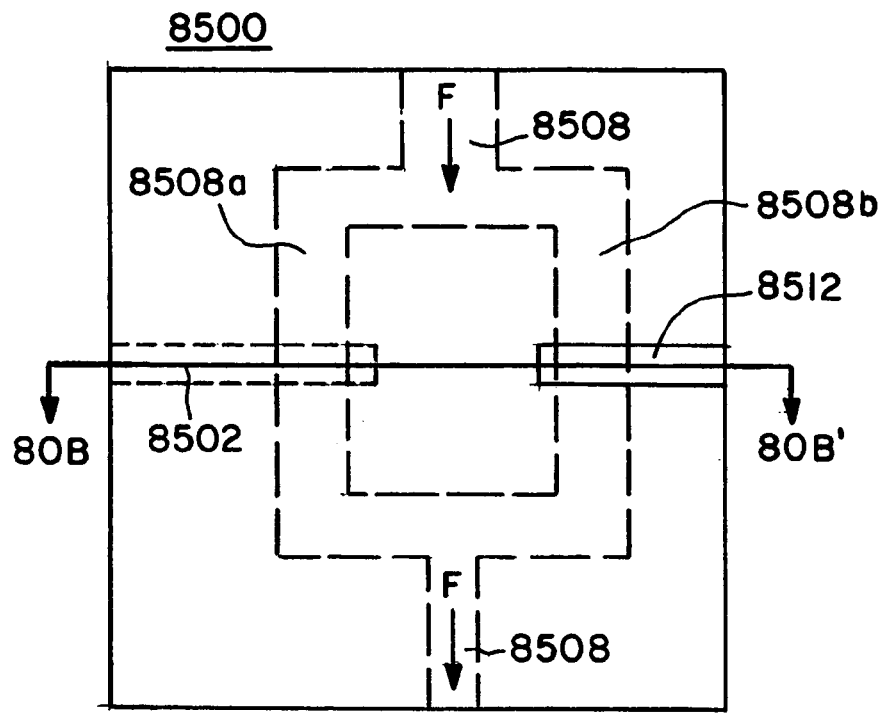
Figure 80B:
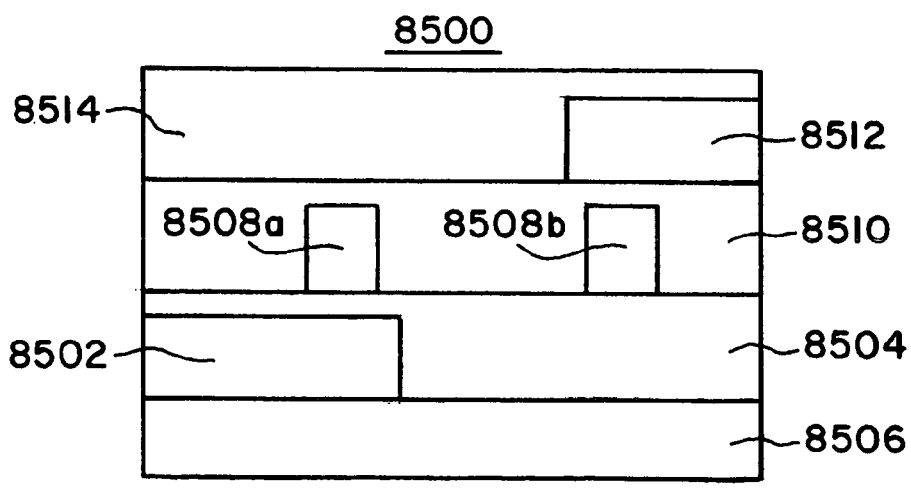

FIGS. 80A-B show plan and cross-sectional views respectively, of an alternative embodiment of a valve structure in accordance with the present invention, utilizing control layers positioned on opposite sides of the layer containing the flow channel.

Figure 81:
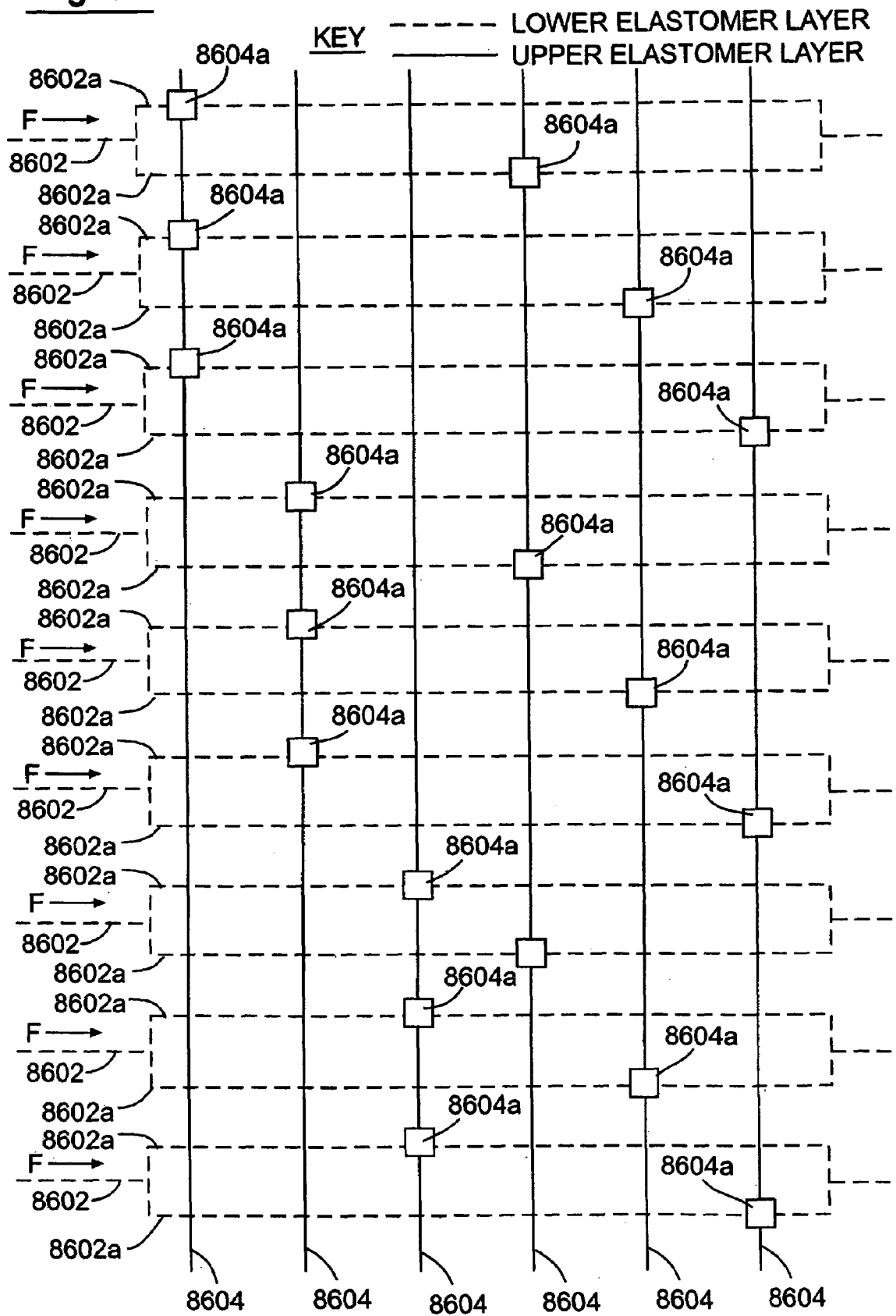

FIG. 81 shows a simplified schematic view of an alternative embodiment of a multiplexer structure.

FIG. 82A is a cross-sectional view of a microfabricated structure including vertical vias.

FIGS. 82B-C are perspective view of steps for fabricating the structure shown in FIG. 82A.

DETAILED DESCRIPTION OF THE PRESENT INVENTION

The present invention comprises a variety of microfabricated elastomeric structures which may be used as pumps or valves. Methods of fabricating the preferred elastomeric structures are also set forth.

Methods of Fabricating the Present Invention:

Two exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. Conversely, the preferred method of FIGS. 8 to 18 involves curing each layer of elastomer "in place". In the following description "channel" refers to a recess in the elastomeric structure which can contain a flow of fluid or gas.

Figure 1:
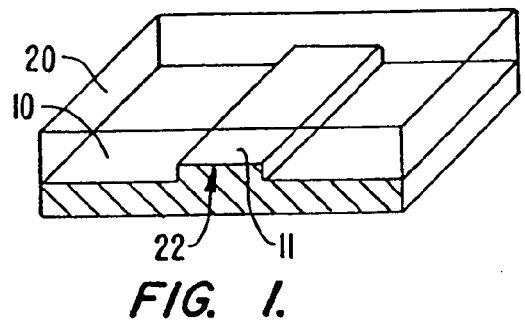
FIG. 1 is an illustration of a first elastomeric layer formed on top of a micromachined mold.

The First Exemplary Method:

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

Figure 2:
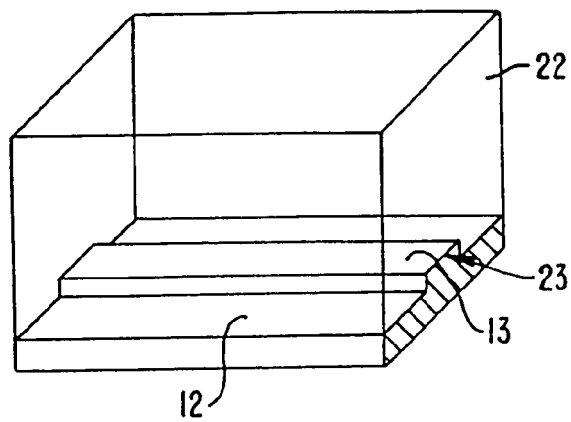
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
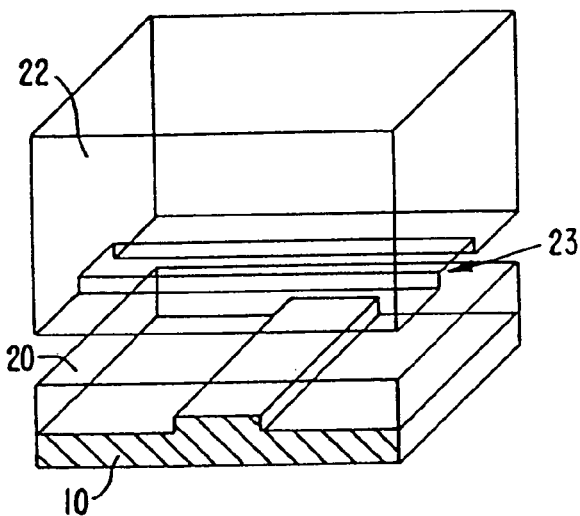
FIG. 3 is an illustration of the elastomeric layer of FIG. 2 removed from the micromachined mold and positioned over the top of the elastomeric layer of FIG. 1
Figure 4:
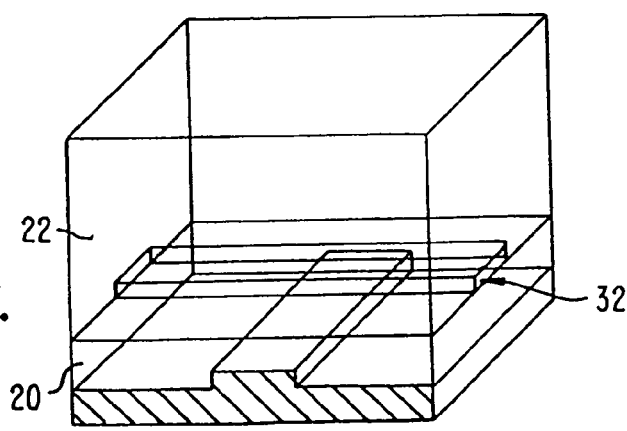
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
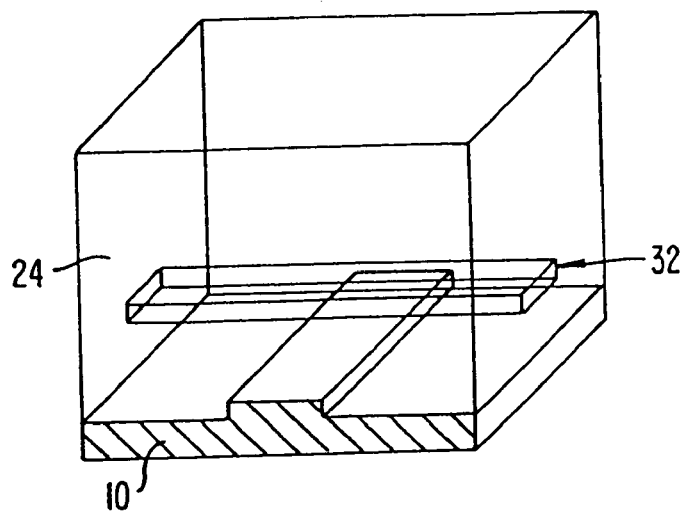
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
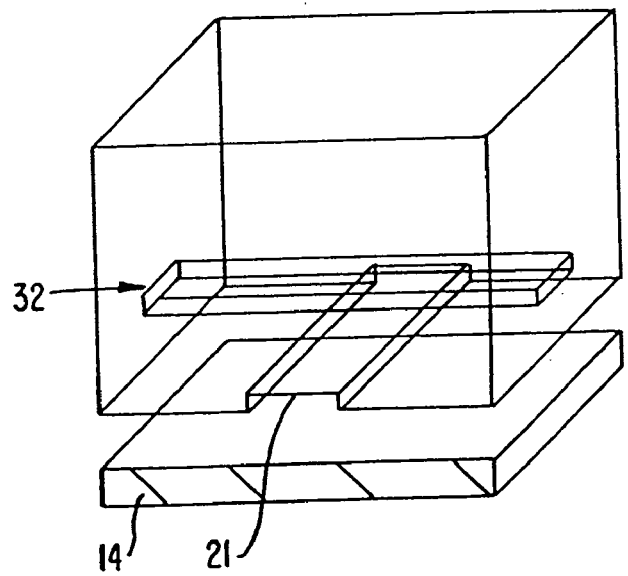
FIG. 6 is an illustration corresponding to FIG. 5, but showing the first micromachined mold removed and a planar substrate positioned in its place.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C-7G.

Figure 7C:
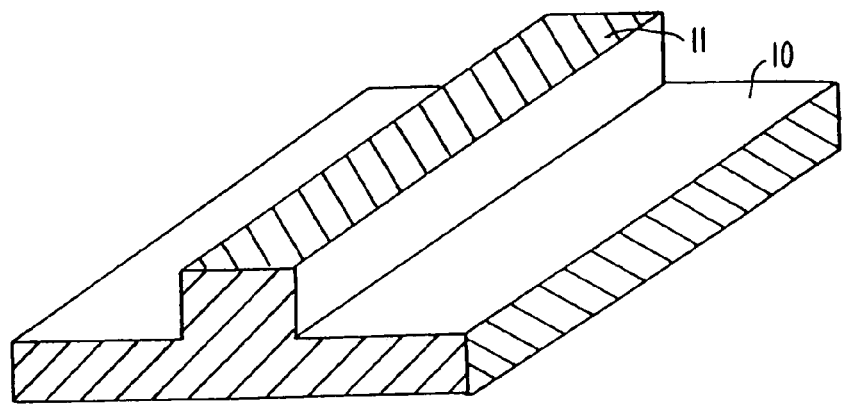
Figure 7D:
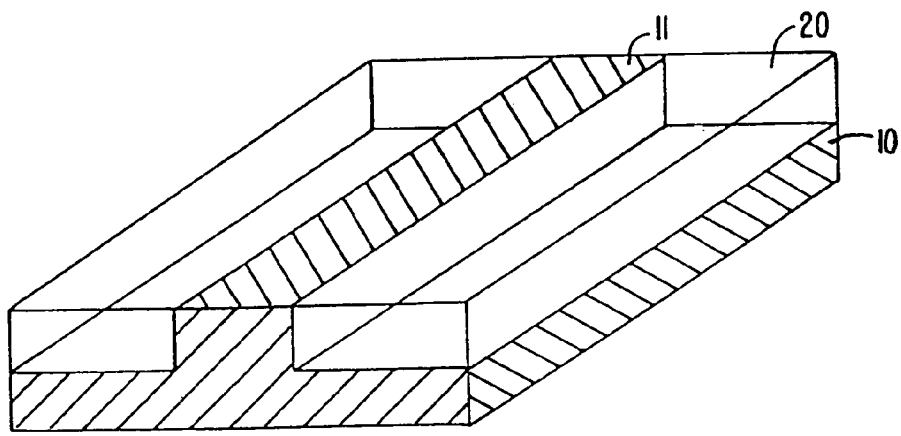

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
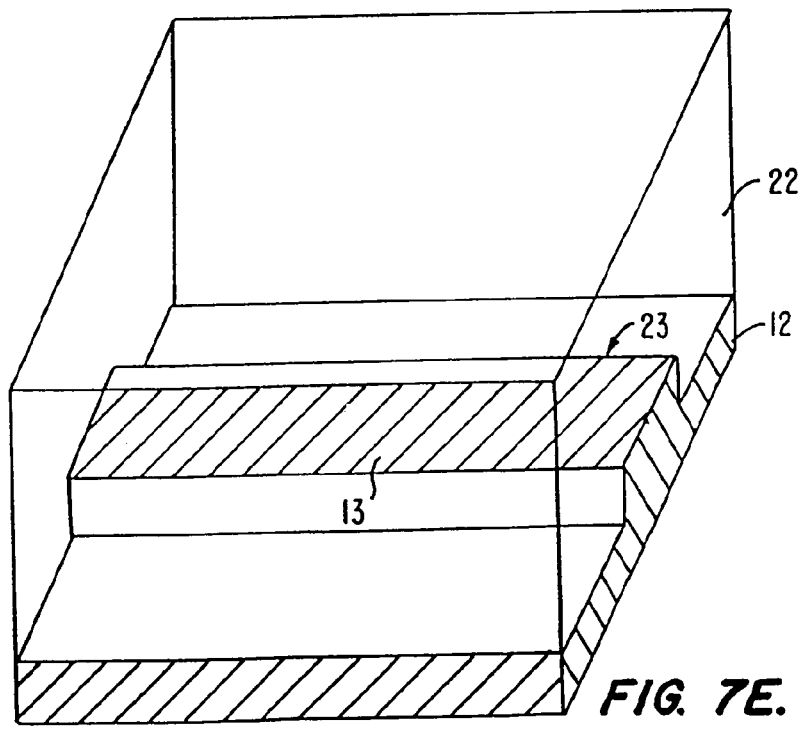

In FIG. 7E, second micro-machined mold 12 having a raised protrusion 13 extending therealong is also provided.

Second elastomeric layer 22 is cast on top of second mold 12 as shown, such that recess 23 is formed in its bottom surface corresponding to the dimensions of protrusion 13.

Figure 7F:
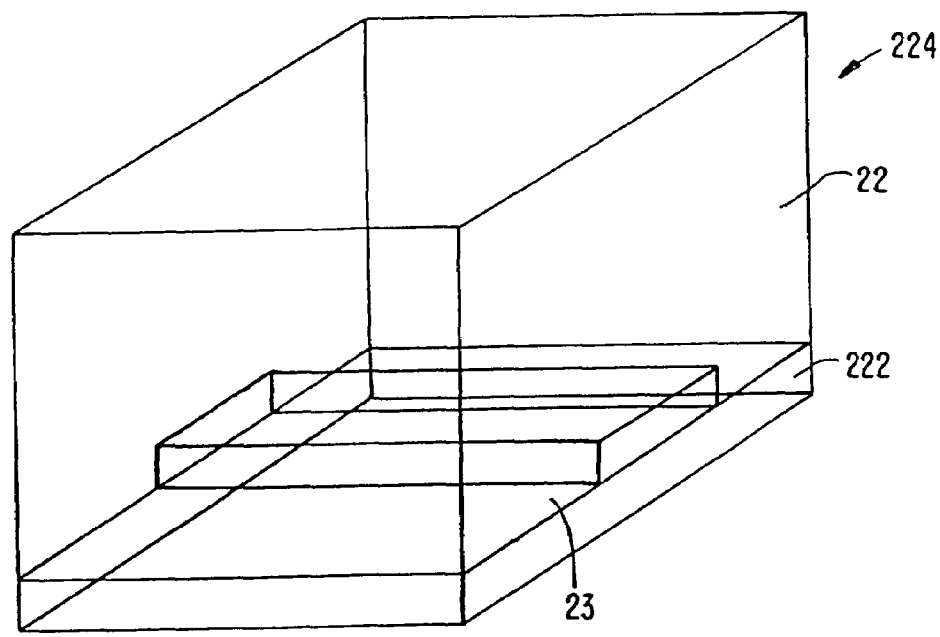

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
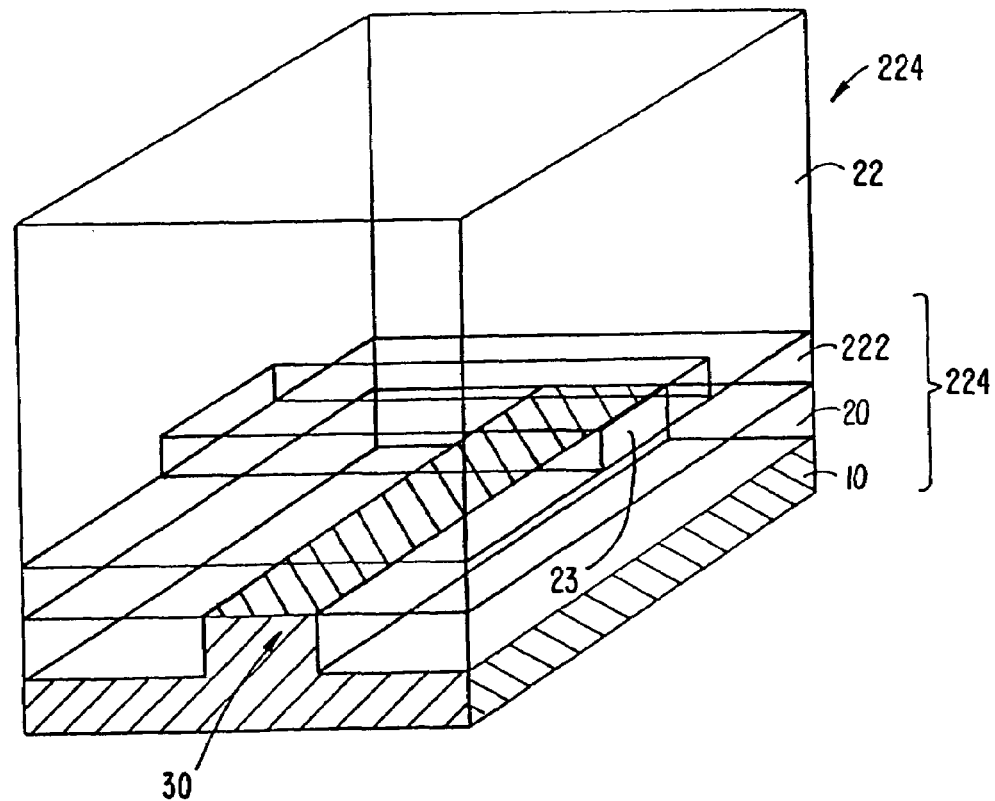

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C-7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

The Second Exemplary Method:

A second exemplary method of fabricating an elastomeric structure which may be used as a pump or valve is set forth in the sequential steps shown in FIGS. 8-18.

In this aspect of the invention, flow and control channels are defined by first patterning photoresist on the surface of an elastomeric layer (or other substrate, which may include glass) leaving a raised line photoresist where a channel is desired. Next, a second layer of elastomer is added thereover and a second photoresist is patterned on the second layer of elastomer leaving a raised line photoresist where a channel is desired. A third layer of elastomer is deposited thereover. Finally, the photoresist is removed by dissolving it out of the elastomer with an appropriate solvent, with the voids formed by removal of the photoresist becoming the flow channels passing through the substrate.

Referring first to FIG. 8, a planar substrate 40 is provided. A first elastomeric layer 42 is then deposited and cured on top of planar substrate 40. Referring to FIG. 9, a first photoresist layer 44A is then deposited over the top of elastomeric layer 42. Referring to FIG. 10, a portion of photoresist layer 44A is removed such that only a first line of photoresist 44B remains as shown. Referring to FIG. 11, a second elastomeric layer 46 is then deposited over the top of first elastomeric layer 42 and over the first line of photoresist 44B as shown, thereby encasing first line of photoresist 44B between first elastomeric layer 42 and second elastomeric layer 46. Referring to FIG. 12, elastomeric layers 46 is then cured on layer 42 to bond the layers together to form a monolithic elastomeric substrate 45.

Referring to FIG. 13, a second photoresist layer 48A is then deposited over elastomeric structure 45. Referring to FIG. 14, a portion of second photoresist layer 48A is removed, leaving only a second photoresist line 48B on top of elastomeric structure 45 as shown. Referring to FIG. 15, a third elastomeric layer 50 is then deposited over the top of elastomeric structure 45 (comprised of second elastomeric layer 42 and first line of photoresist 44B) and second photoresist line 48B as shown, thereby encasing the second line of photoresist 48B between elastomeric structure 45 and third elastomeric layer 50.

Referring to FIG. 16, third elastomeric layer 50 and elastomeric structure 45 (comprising first elastomeric layer 42 and second elastomeric layer 46 bonded together) is then bonded together forming a monolithic elastomeric structure 47 having photoresist lines 44B and 48B passing therethrough as shown. Referring to FIG. 17, photoresist lines 44B, 48B are then removed (for example, by an solvent) such that a first flow channel 60 and a second flow channel 62 are provided in their place, passing through elastomeric structure 47 as shown. Lastly, referring to FIG. 18, planar substrate 40 can be removed from the bottom of the integrated monolithic structure.

The method described in FIGS. 8-18 fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, as described in detail below in connection with FIGS. 35A-35D, gold metal may be etched selective to RTV 615 elastomer utilizing the appropriate chemical mixture.

Preferred Layer and Channel Dimensions:

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30, 32, 60 and 62 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30, 32, 60 and 62 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 µm, 1 µm, 2 µm, 5 µm, 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, and 250 µm.

Flow channels 30, 32, 60, and 62 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 µm, 0.02 µm, 0.05 µm, 0.1 µm, 0.2 µm, 0.5 µm, 1 µm, 2 µm, 3 µm, 4 nm, 5 µm, 7.5 µm, 10 µm, 12.5 µm, 15 µm, 17.5 µm, 20 µm, 22.5 µm, 25 µm, 30 µm, 40 µm, 50 µm, 75 µm, 100 µm, 150 µm, 200 µm, and 250 µm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 µm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

Elastomeric layer 22 may be cast thick for mechanical stability. In an exemplary embodiment, layer 22 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 µm, 0.02 µm, 0.03 µm, 0.05 µm, 0.1 µm, 0.2 µm, 0.3 µm, 0.5 µm, 1 µm, 2 µm, 3 µm, 5 µm, 7.5 µm, 10 µm, 12.5 µm, 15 µm, 17.5 µm, 20 µm, 22.5 µm, 25 µm, 30 µm, 40 µm, 50 µm, 75 µm, 100 µm, 150 µm, 200 µm, 250 µm, 300 µm, 400 µm, 500 µm, 750 µm, and 1000 µm Similarly, first elastomeric layer 42 may have a preferred thickness about equal to that of elastomeric layer 20 or 22; second elastomeric layer 46 may have a preferred thickness about equal to that of elastomeric layer 20; and third elastomeric layer 50 may have a preferred thickness about equal to that of elastomeric layer 22.

As just described, the lateral dimensions of features of microfabricated devices in accordance with embodiments of the present invention can be precisely controlled utilizing lithographic techniques, either in defining features of the nonelastomer mold, or in defining sacrificial features directly on the elastomer material. Similarly, the dimension of features in the vertical direction may be varied and controlled through the formation of may be defined utilizing flow channel can be precisely controlled achieved through the development of resists and other sacrificial materials.

For example, FIG. 71A shows a cross-sectional view of a mold 7600 featuring topographic features 7602a and 7602b of differing heights Y and Y', respectively. Features 7602a and 7602b may be created directly through the patterning of multiple resist layers 7604 and 7606 as shown in FIG. 71A. Upon removal of elastomer material 7608 from mold 7600 of FIG. 71A, elastomer layer 7610 shown in FIG. 71B featuring flow channel 7612 having portions 7612a and 7612b of different heights Y and Y' may be formed.

Embodiments of the present invention may utilize positive or negative resist materials to form features of different heights. Embodiments of the present invention may utilize photoresist or electron beam resist materials.

While FIGS. 71A-B show creation of features of varying height through patterning of multiple resist layers, use of resist material directly in the mold is not required by the present invention. In alternative embodiments, multiple patterned layers of resist may serve as masks for the removal of an underlying substrate material to different depths. Upon removal of the patterned resist, features of varying depth in the substrate may define the molded piece.

Moreover, while FIGS. 71A-71B show the creation of molded features of varying height utilizing multiple resist layers, this is also not required by embodiments in accordance with the present invention. In alternative embodiments, gray scale resists may be used. Upon development, thickness of the gray scale resist reflects intensity of the incident radiation during exposure. Varying the intensity of such incident radiation can result in formation of features of different heights from a single layer of resist material.

Multilayer Soft Lithography Construction Techniques and Materials:

Soft Lithographic Bonding:

Preferably, elastomeric layers 20 and 22 (or elastomeric layers 42, 46 and 50) are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogenous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogenous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure as described above in FIGS. 8-18, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 12 at 2000 rpm's for 30 seconds yielding a thickness of approximately 40 microns. Second elastomeric layer 22 may be created by spin-coating an RTV mixture on microfabricated mold 11. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicon rubber.

Using the various multilayer soft lithography construction techniques and materials set forth herein, the present inventors have experimentally succeeded in creating channel networks comprises of up to seven separate elastomeric layers thick, with each layer being about 40 μm thick. It is foreseeable that devices comprising more than seven separate elastomeric layers bonded together could be developed.

While the above discussion focuses upon methods for bonding together successive horizontal layers of elastomer, in alternative embodiments in accordance with the present invention bonding could also occur between vertical interfaces of different portions of an elastomer structure. One embodiment of such an alternative approach is shown in FIGS. 55A-55C, which illustrate cross-sectional views of a process for forming such a device utilizing separation of an elastomer structure along a flow channel section.

FIG. 55A shows a cross-section of two devices 6000 and 6010 comprising respective first elastomer layers 6002 and 6012 overlying second elastomer layers 6004 and 6014, thereby defining respective flow channels 6006 and 6016. First elastomer layer 6002 comprises a first elastomer material, and second elastomer layer 6004 comprises a second elastomer material configured to bond with the first elastomer material. Conversely, first elastomer layer 6012 comprises the second elastomer material and second elastomer layer 6014 comprises the first elastomer material.

FIG. 55B shows the results of cutting devices 6000 and 6010 along vertical lines 6001 and 6011 extending along the length of flow channels 6006 and 6016, respectively, to form half structures 6000*a-b* and 6010*a-b*.

FIG. 55C shows the results of cross-combining the half structures, such that first half 6000*a* is bonded to second half 6010*b* to form device 6008, and first half 6010*a* is bonded to second half 6000*b* to form device 6018. This reassembly is enabled by the bonding between the first elastomer material and the second elastomer material.

The bonding method just described can be useful for the assembly of multiple chips together, edge to edge, to form a multi-chip module. This is particularly advantageous for the creation of microfluidic modules, each having a particular function, which can be assembled from component chips as desired.

While the above description focuses upon bonding of successive layers featuring horizontally-oriented channels, it is also possible to fabricate a layer having a horizontally-oriented channel, and then to orient the layer in a vertical position and bond the vertically-oriented layer to a horizontally oriented layer. This is shown in FIG. 68A-B, which illustrates cross-sectional views of a method for bonding a vertically-oriented microfabricated elastomer structure to a horizontally-oriented microfabricated elastomer structure.

FIG. 68A shows first horizontally-oriented microfabricated elastomer structure 7300 comprising control channel 7302 formed in first elastomer layer 7304 and overlying and separated from flow channel 7306 by membrane 7308 formed from second elastomer layer 7310. Second elastomer layer 7310 also defines a vertical via 7312 in communication with flow channel 7306, and first elastomer layer 7304 does not extend completely over the top of second elastomer layer 7310. Second horizontally-oriented microfabricated elastomer structure 7320 similarly comprises control channel 7322 formed in third elastomer layer 7324 and overlying and separated from flow channel 7326 by membrane 7328 formed from fourth elastomer layer 7330.

FIG. 68B shows assembly of a compound microfabricated elastomeric structure 7340 by orienting second microfabricated structure 7320 vertically on end, and placing second structure 7320 into contact with first microfabricated structure 7300 such that flow channel 7326 in contact with via 7312. By employing compound structure 7340, fluids can be withdrawn from or introduced into flow channel 7306 through via 7312.

Suitable Elastomeric Materials:

Allcock et al, *Contemporary Polymer Chemistry*, 2$^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, elastomeric layers 20, 22, 42, 46 and 50 may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure polyisobutylene has no double bonds, but is crosslinked to use as an elastomer by including a small amount (~1%) of isoprene in the polymerization. The isoprene monomers give pendant double bonds on the polyisobutylene backbone, which may then be vulcanized as above.

Poly(styrene-butadiene-styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

Cross Linking Agents:

In addition to the use of the simple "pure" polymers discussed above, crosslinking agents may be added. Some agents (like the monomers bearing pendant double bonds for vulcanization) are suitable for allowing homogeneous (A to A) multilayer soft lithography or photoresist encapsulation; in such an approach the same agent is incorporated into both elastomer layers. Complementary agents (i.e. one monomer bearing a pendant double bond, and another bearing a pendant Si—H group) are suitable for heterogeneous (A to B) multilayer soft lithography. In this approach complementary agents are added to adjacent layers.

Other Materials:

In addition, polymers incorporating materials such as chlorosilanes or methyl-, ethyl-, and phenylsilanes, and polydimethylsiloxane (PDMS) such as Dow Chemical Corp. Sylgard 182, 184 or 186, or aliphatic urethane diacrylates such as (but not limited to) Ebecryl 270 or Irr 245 from UCB Chemical may also be used.

The following is a non-exclusive list of elastomeric materials which may be utilized in connection with the present invention: polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

Doping and Dilution:

Elastomers may also be "doped" with uncrosslinkable polymer chains of the same class. For instance RTV 615 may be diluted with GE SF96-50 Silicone Fluid. This serves to reduce the viscosity of the uncured elastomer and reduces the Young's modulus of the cured elastomer. Essentially, the crosslink-capable polymer chains are spread further apart by the addition of "inert" polymer chains, so this is called "dilution". RTV 615 cures at up to 90% dilution, with a dramatic reduction in Young's modulus.

FIG. 49 plots Young's modulus versus percentage dilution with GE SF96-50 diluent of GE RTV 615 elastomer having a ratio of 30:1 A:B. FIG. 49 shows that the flexibility of the elastomer material, and hence the responsiveness of the valve membrane to an applied actuation force, can be controlled during fabrication of the device.

Other examples of doping of elastomer material may include the introduction of electrically conducting or magnetic species, as described in detail below in conjunction with alternative methods of actuating the membrane of the device. Should it be desired, doping with fine particles of material having an index of refraction different than the elastomeric material (i.e. silica, diamond, sapphire) is also contemplated as a system for altering the refractive index of the material. Strongly absorbing or opaque particles may be added to render the elastomer colored or opaque to incident radiation. This may conceivably be beneficial in an optically addressable system.

Finally, by doping the elastomer with specific chemical species, these doped chemical species may be presented at the elastomer surface, thus serving as anchors or starting points for further chemical derivitization.

Pre-Treatment and Surface Coating

Once the elastomeric material has been molded or etched into the appropriate shape, it may be necessary to pre-treat the material in order to facilitate operation in connection with a particular application.

For example, one possible application for an elastomeric device in accordance with the present invention is to sort biological entities such as cells or DNA. In such an application, the hydrophobic nature of the biological entity may cause it to adhere to the hydrophobic elastomer of the walls of the channel. Therefore, it may be useful to pre-treat the elastomeric structure order to impart a hydrophilic character to the channel walls. In an embodiment of the present invention utilizing the General Electric RTV 615 elastomer, this can be accomplished by boiling the shaped elastomer in acid (e.g. 0.01% HCl in water, pH 2.7, at 60° C. for 40 min).

Other types of pre-treatment of elastomer material are also contemplated by the present application. For example, certain portions of elastomer may be pre-treated to create anchors for surface chemistry reactions (for example in the formation of peptide chains), or binding sites for antibodies, as would be advantageous in a given application. Other examples of pre-treatment of elastomer material may include the introduction of reflective material on the elastomer surface, as described in detail below in conjunction with the micro-mirror array application.

Methods of Operating the Present Invention:

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

It is to be understood that exactly the same valve opening and closing methods can be achieved with flow channels 60 and 62.

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 µm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 μL to 10 nL, 100 ff, to 1 nL, and 1 pL to 100 pL The extremely small volumes capable of being delivered by pumps and valves in accordance with the present invention represent a substantial advantage. Specifically, the smallest known volumes of fluid capable of being manually metered is around 0.1 μl. The smallest known volumes capable of being metered by automated systems is about ten-times larger (1 μl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3), \text{ where:} \quad (1)$$

w=deflection of plate;
B=shape coefficient (dependent upon length vs. width and support of edges of plate);
P=applied pressure;
b=plate width
E=Young's modulus; and
h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticities, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

FIGS. 21a and 21b illustrate valve opening vs. applied pressure for a 100 μm wide first flow channel 30 and a 50 μm wide second flow channel 32. The membrane of this device was formed by a layer of General Electric Silicones RTV 615 having a thickness of approximately 30 μm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

Connection of conventional microfluidic devices to an external fluid flow poses a number of problems avoided by the external configuration just described. One such problem is the fragility of their connections with the external environment. Specifically, conventional microfluidic devices are composed of hard, inflexible materials (such as silicon), to which pipes or tubing allowing connection to external elements must be joined. The rigidity of the conventional material creates significant physical stress at points of contact with small and delicate external tubing, rendering conventional microfluidic devices prone to fracture and leakage at these contact points.

By contrast, the elastomer of the present invention is flexible and can be easily penetrated for external connection by a tube composed a hard material. For example, in an elastomer structure fabricated utilizing the method shown in FIGS. 1-7B, a hole extending from the exterior surface of the structure into the control channel can be made by penetrating the elastomer with metal hypodermic tubing after the upper elastomer piece has been removed from the mold (as shown in FIG. 3) and before this piece has been bonded to the lower elastomer piece (as shown in FIG. 4). Between these steps, the roof of the control channel is exposed to the user's view and is accessible to insertion and proper positioning of the hole. Following completion of fabrication of the device, the metal hypodermic tubing is inserted into the hole to complete the fluid connection.

Moreover, the elastomer of the present invention will flex in response to physical strain at the point of contact with an external connection, rendering the external physical connection more robust. This flexibility substantially reduces the chance of leakage or fracture of the present device.

Another disadvantage of conventional microfluidic devices is the difficulty in establishing an effective seal between the device and its external links. Because of the extremely narrow diameter of the channels of these devices, even moderate rates of fluid flow can require extremely high pressures. Unwanted leakage at the junction between the device and external connections may result. However, the flexibility of the elastomer of the present device also aids in overcoming leakage relating to pressure. In particular, the flexible elastomeric material flexes to conform around inserted tubing in order to form a pressure resistant seal.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebro-spinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuatable valves are contemplated in the present invention, and the pressure ranges over which a valve is linearly actuatable will vary with the specific embodiment.

FIG. 22 illustrates time response (i.e.: closure of valve as a function of time in response to a change in applied pressure) of a 100 μm×100 μm×10 μm RTV microvalve with 10-cm-long air tubing connected from the chip to a pneumatic valve as described above.

Two periods of digital control signal, actual air pressure at the end of the tubing and valve opening are shown in FIG. 22. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force ($\leqq$40 kPa). Thus, $\tau_{close}$ is expected to be smaller than $\tau_{open}$. There is also a lag between the control signal and control pressure response, due to the limitations of the miniature valve used to control the pressure. Calling such lags t and the 1/e time constants $\tau$, the values are: $\tau_{open}$=3.63 ms, $t_{open}$=1.88 ms, $t_{close}$=2.15 ms, $\tau_{close}$=0.51 ms. If $3\tau$ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C-7H.)

When experimentally measuring the valve properties as illustrated in FIGS. 21 and 22, the valve opening was measured by fluorescence. In these experiments, the flow channel was filled with a solution of fluorescein isothiocyanate (FITC) in buffer (pH$\geqq$8) and the fluorescence of a square area occupying the center ~⅓rd of the channel is monitored on an epi-fluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

Flow Channel Cross Sections:

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Referring to FIG. 19, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 20, the cross-section of a flow channel 30 instead has an upper curved surface.

Referring first to FIG. 19, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

In the alternate preferred embodiment of FIG. 20, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 19.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel In an alternate aspect, (not illustrated), the bottom of flow channel 30 is rounded such that its curved surface mates with the curved upper wall 25A as seen in FIG. 20 described above.

In a further alternative aspect, the control channel may be positioned underneath a flow channel having an arched ceiling, such that deflection of the membrane causes the membrane to bow upwards and conform to the arched ceiling of the flow channel, thereby ensuring a good seal. FIG. 72 shows a cross-sectional view of such an alternative valve structure 7700, wherein control channel 7702 is formed in first elastomer layer 7704 in contact with underlying substrate 7706. Second elastomer layer 7708 containing flow channel 7710 is positioned over first elastomer layer 7704, such that flow channel 7710 is orthogonal to underlying control channel.

FIG. 72 shows that membrane portion 7712 defined between control channel 7702 and flow channel 7710 can be deflected into flow channel 7710 to conform to the arched shape of ceiling 7710a of flow channel 7710. Conformity of the actuated membrane 7712 with the shape of the flow channel ceiling prevents leakage of materials through the closed valve and helps ensure linear response of the valve.

The valve architecture illustrated in FIG. 72 is particularly useful where the flow channel is deep (i.e. >50 μm), and the large volume of elastomer present at the edges of the flow channel would interfere with deflection of edges of an overlying membrane into the flow channel. Valve architectures of the type illustrated in FIG. 72 have been operated to achieve closure of a 300 μm wide, 50 μm deep flow channel with an actuation pressure in the control channel of less than 1 psi. Closure of a valve of the type shown in FIG. 72 having a flow channel 50 μm deep and 100 μm wide has been achieved with an actuation pressure in the control channel of 8 psi.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel.

Moreover, isotropic etching of a nonelastomer substrate such as single crystal silicon typically produces a recess having a concave profile. Where the walls and floor of a flow channel in a nonelastomer substrate are created by isotropic etching, an overlying elastomer membrane can readily conform to and seal against the concave shape of the flow channel floor.

In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

Alternate Valve Actuation Techniques:

In addition to pressure based actuation systems described above, optional electrostatic and magnetic actuation systems are also contemplated, as follows.

Electrostatic actuation can be accomplished by forming oppositely charged electrodes (which will tend to attract one another when a voltage differential is applied to them) directly into the monolithic elastomeric structure. For example, referring to FIG. 7B, an optional first electrode 70 (shown in phantom) can be positioned on (or in) membrane 25 and an optional second electrode 72 (also shown in phantom) can be positioned on (or in) planar substrate 14. When electrodes 70 and 72 are charged with opposite polarities, an attractive force between the two electrodes will cause membrane 25 to deflect downwardly, thereby closing the "valve" (i.e.: closing flow channel 30).

For the membrane electrode to be sufficiently conductive to support electrostatic actuation, but not so mechanically stiff so as to impede the valve's motion, a sufficiently flexible electrode must be provided in or over membrane 25. Such an electrode may be provided by a thin metallization layer, doping the polymer with conductive material, or making the surface layer out of a conductive material.

In an exemplary aspect, the electrode present at the deflecting membrane can be provided by a thin metallization layer which can be provided, for example, by sputtering a thin layer of metal such as 20 nm of gold. In addition to the formation of a metallized membrane by sputtering, other metallization approaches such as chemical epitaxy, evaporation, electroplating, and electroless plating are also available. Physical transfer of a metal layer to the surface of the elastomer is also available, for example by evaporating a metal onto a flat substrate to which it adheres poorly, and then placing the elastomer onto the metal and peeling the metal off of the substrate.

A conductive electrode 70 may also be formed by depositing carbon black (i.e. Cabot Vulcan XC72R) on the elastomer surface, either by wiping on the dry powder or by exposing the elastomer to a suspension of carbon black in a solvent which causes swelling of the elastomer, (such as a chlorinated solvent in the case of PDMS). Alternatively, the electrode 70 may be formed by constructing the entire layer 20 out of elastomer doped with conductive material (i.e. carbon black or finely divided metal particles). Yet further alternatively, the electrode may be formed by electrostatic deposition, or by a chemical reaction that produces carbon. In experiments conducted by the present inventors, conductivity was shown to increase with carbon black concentration from $5.6\times10^{-16}$ to about $5\times10^{-3}$ $(\Omega\text{-cm})^{-1}$. The lower electrode 72, which is not required to move, may be either a compliant electrode as described above, or a conventional electrode such as evaporated gold, a metal plate, or a doped semiconductor electrode.

A pump or valve structure in accordance with embodiments of the present invention could also be actuated by applying electrical potential to materials whose physical properties change in an electromagnetic field. One example of such a material is liquid mercury, whose surface tension changes in an applied electromagnetic field. In this method of actuation, a pocket of liquid mercury is present in the control channel overlying the flow channel. The mercury filled pocket is connected to electrodes. In response to the voltage applied across the electrode, liquid mercury within the control experiences a change in surface tension, changing the adjacent membrane from a relaxed state to a non-relaxed state. Depending upon the particular structure of the valve, this changed state may correspond to either opening or closing the valve. Upon cessation of the applied voltage, mercury within the control channel will resume its original surface tension, and the membrane will assume is relaxed position.

In a similar approach, surfaces of a control channel may be coated with a material that changes shape in response to an applied potential. For example, polypyrrole is a conjugated polymer which changes shape within an electrolyte bearing an applied voltage. A control channel may be coated with polypyrrole or another organic conductor which changes macroscopic structure in response to an applied electric field. The coated control channel is then filled with electrolyte, and the electrolyte placed into contact with electrodes. When a potential difference is applied across the electrolyte, the coated channel is attracted to the electrode. Thus by designing the proper placement of the polypyrrole coated channel in relation to the electrode, the flow channel can be selectively opened or closed by applying a current.

Magnetic actuation of the flow channels can be achieved by fabricating the membrane separating the flow channels with a magnetically polarizable material such as iron, or a permanently magnetized material such as polarized NdFeB. In experiments conducted by the present inventors, magnetic silicone was created by the addition of iron powder (about 1 um particle size), up to 20% iron by weight.

Where the membrane is fabricated with a magnetically polarizable material, the membrane can be actuated by attraction in response to an applied magnetic field Where the membrane is fabricated with a material capable of maintaining permanent magnetization, the material can first be magnetized by exposure to a sufficiently high magnetic field, and then actuated either by attraction or repulsion in response to the polarity of an applied inhomogenous magnetic field.

The magnetic field causing actuation of the membrane can be generated in a variety of ways. In one embodiment, the magnetic field is generated by an extremely small inductive coil formed in or proximate to the elastomer membrane. The actuation effect of such a magnetic coil would be localized, allowing actuation of individual pump and/or valve structures. Alternatively, the magnetic field could be generated by a larger, more powerful source, in which case actuation would be global and would actuate multiple pump and/or valve structures at one time.

It is further possible to combine pressure actuation with electrostatic or magnetic actuation. Specifically, a bellows structure in fluid communication with a recess could be electrostatically or magnetically actuated to change the pressure in the recess and thereby actuate a membrane structure adjacent to the recess.

In addition to electrical or magnetic actuation as described above, optional electrolytic and electrokinetic actuation systems are also contemplated by the present invention.

For example, actuation pressure on the membrane could arise from an electrolytic reaction in a recess (control channel) overlying the membrane. In such an embodiment, electrodes present in the recess would apply a voltage across an electrolyte in the recess. This potential difference would cause electrochemical reaction at the electrodes and result in the generation of gas, in turn giving rise to a pressure differential in the recess. Depending upon the elastomer type and the exact device structure, gas generated by such an electrolytic reaction could be mechanically vented or allowed to slowly diffuse out of the polymer matrix of the elastomer, releasing the pressure generated within the pocket and returning the membrane to its relaxed state.

Alternatively, rather than relying on outdiffusion for reversibility of actuation, the gases could be recombined to form water, releasing pressure and returning the membrane to its relaxed state. Formation of water from hydrogen and water vapor can be accomplished through the use of a catalyst, or by providing sufficient energy to cause controlled combustion.

One potential application of an electrolytic method of actuation is the microsyringe structure shown in FIG. 56. FIG. 56 is a schematic view of an elastomer block bearing a flow channel 6100 in fluid communication with first, second, and third chambers 6102, 6104, and 6106 respectively. First chamber 6102 contains a salt solution 6103 in contact with electrodes 6108 and 6110. Third chamber 6106 contains drug 6107 or other liquid material that is to be output from the fluidic device through output channel 6112. Second chamber 6104 contains an inert oil 6105 intended to physically isolate drug 6107 from salt solution 6103. Upon application of a potential difference across electrodes 6108 and 6110, salt solution 6103 undergoes electrolysis, generating gases such that first chamber 6102 rapidly experiences an elevation in pressure. This elevation in pressure causes oil 6105 to flow from second chamber 6104 into third chamber 6106, displacing drug 6107 and causing the flow of drug 6107 from third chamber 6106 to output channel 6112 and ultimately into a patient.

An embodiment of a method for actuating a microfabricated elastomer structure comprises providing an aqueous salt solution in a control recess formed in an elastomeric block and overlying and separated from a flow channel by an elastomer membrane, applying a potential difference to the salt solution to generate a gas, such that a pressure in the control recess causes the membrane to deflect into the flow channel.

An embodiment of a microfabricated syringe structure in accordance with the present invention comprises a first chamber formed in an elastomeric block and including an aqueous salt solution, a first electrode, and a second electrode. A second chamber is formed in the elastomeric block and contains an inert liquid, the second chamber in fluid communication with the first chamber through a first flow channel. A third chamber is formed in the elastomeric block and containing an ejectable material, the third chamber in fluid communication with the second chamber through a second flow channel and in fluid communication with an environment through an outlet, such that application of a potential difference across the electrodes generates gas in the first chamber, the gas displacing the inert material into the third chamber, the inert material displacing the injectable material into the environment.

Actuation pressure on the membrane of a device in accordance with embodiments of the present invention could also arise from an electrokinetic fluid flow in the control channel. In such an embodiment, electrodes present at opposite ends of the control channel would apply a potential difference across an electrolyte present in the control channel. Electrokinetic flow induced by the potential difference could give rise to a pressure differential.

Finally, it is also possible to actuate the device by causing a fluid flow in the control channel based upon the application of thermal energy, either by thermal expansion or by production of gas from liquid. For example, in one alternative embodiment in accordance with the present invention, a pocket of fluid (e.g. in a fluid-filled control channel) is positioned over the flow channel. Fluid in the pocket can be in communication with a temperature variation system, for example a heater. Thermal expansion of the fluid, or conversion of material from the liquid to the gas phase, could result in an increase in pressure, closing the adjacent flow channel. Subsequent cooling of the fluid would relieve pressure and permit the flow channel to open. Alternatively, or in conjunction with simple cooling, heated vapor from the fluid pocket could diffuse out of the elastomer material, thereby relieving pressure and permitting the flow channel to open. Fluid lost from the control channel by such a process could be replenished from an internal or external reservoir.

Similar to the temperature actuation discussed above, chemical reactions generating gaseous products may produce an increase in pressure sufficient for membrane actuation.

Networked Systems:

FIGS. 23A and 23B show a views of a single on/off valve, identical to the systems set forth above, (for example in FIG. 7A). FIGS. 24A and 24B shows a peristaltic pumping system comprised of a plurality of the single addressable on/off valves as seen in FIG. 23, but networked together. FIG. 25 is a graph showing experimentally achieved pumping rates vs. frequency for the peristaltic pumping system of FIG. 24. FIGS. 26A and 26B show a schematic view of a plurality of flow channels which are controllable by a single control line. This system is also comprised of a plurality of the single addressable on/off valves of FIG. 23, multiplexed together, but in a different arrangement than that of FIG. 23. FIG. 27 is a schematic illustration of a multiplexing system adapted to permit fluid flow through selected channels, comprised of a plurality of the single on/off valves of FIG. 23, joined or networked together.

Referring first to FIGS. 23A and 23B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 23 to 26, a plurality of such addressable valves are joined or networked together in various arrangements to produce pumps, capable of peristaltic pumping, and other fluidic logic applications.

Referring to FIGS. 24A and 24B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 μm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of *E. Coli* pumped through a channel and tested for viability showed a 94% survival rate.

FIG. 25 is a graph showing experimentally achieved pumping rates vs. frequency for the peristaltic pumping system of FIG. 24.

While the embodiment of a pumping structure shown in FIGS. 24A-24B utilizes a plurality of parallel flow channels, this is not required by the present invention. FIG. 73A presents a plan view of an alternative embodiment of a pump structure in accordance with the present invention, wherein serpentine control channel 7800 crosses over underlying flow channel 7802 at three different points, thereby creating three valve structures 7804, 7806, and 7808 having membranes 7804a, 7806a, and 7808a respectively.

Application of a high pressure signal to first end 7800a of control channel 7800 causes a high pressure signal to propagate to first valve 7804, then to second valve 7806, and finally to third valve 7808, as shown in TABLE 1.

TABLE 1

| | 0 = valve open; 1 = valve closed | | |
| --- | --- | --- | --- |
| TIME | VALVE 7804 | VALVE 7806 | VALVE 7808 |
| $T_0$ | 1 | 0 | 0 |
| $T_1$ | 1 | 1 | 0 |
| $T_2$ | 1 | 1 | 1 |
| $T_3$ | 0 | 1 | 1 |
| $T_4$ | 0 | 0 | 1 |
| $T_5$ | 0 | 0 | 0 |

The resulting sequence of deflection of membranes 7804a, 7806a, and 7808a would create a pumping action in flow channel 7802 in direction F. Moreover, relaxation of pressure at first end 7800d of control channel 7800 at time $T_3$ would cause a low pressure signal to propagate to first valve 7804, then to second valve 7806, and finally to third valve 7808, setting the stage for another pumping sequence without causing reversal in direction of material previously flowed through channel 7802.

FIGS. 73B and 73C plot flow velocity versus frequency of application of high pressure signal to the control line of a pump structure of FIG. 73A, the pump structure having a control line of with 100 μm and flow channel cross-over points at spacings of 200 μm. FIG. 73B shows flow velocity resulting from an actuation pressure that oscillates between an elevated pressure and ambient pressure. FIG. 73C shows flow velocity resulting from an actuation pressure that oscillates between an elevated pressure and a vacuum. Both FIGS. 73B and 73C show an effective pumping action, with the larger actuation pressure range of FIG. 73C giving rise to more rapid flow velocities.

FIGS. 26A and 26B illustrates another way of assembling a plurality of the addressable valves of FIG. 21. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 27 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 26A and 26B) depends strongly upon the membrane dimensions. Accordingly, by varying the widths of flow channel control line 32 in FIGS. 26A and 26B, it is possible to have a control line pass over multiple flow channels, yet only actuate (i.e.: seal) desired flow channels. FIG. 27 illustrates a schematic of such a system, as follows.

A plurality of parallel flow channels 30A, 30B, 30C, 30D, 30E and 30F are positioned under a plurality of parallel control lines 32A, 32B, 32C, 32D, 32E and 32F. Control channels 32A, 32B, 32C, 32D, 32E and 32F are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, 32D, 32E and 32F have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only $2(\log_2 n)$ control lines.

The inventors have succeeded in fabricating microfluidic structures with densities of 30 devices/mm$^2$, but greater densities are achievable. For example, FIG. 60 shows a plan view of multiplexer device 6500 comprising sixty-four parallel flow channels 6502 controlled by twelve overlying control channels 6504. Fluid is introduced into multiplexer structure 6500 through input 6506, and the distributed to flow channels 6502 through the peristaltic pumping action of pumping control lines 6508a-c.

Control channels 6504a-l may be understood as six pairs of control lines 6504a-b, 6504c-d, 6504e-f, 6504g-h, 6504i-j, and 6504k-l featuring complementary wide and narrow channel regions. For example, application of a control pressure to line 6504a will close the first thirty-two flow channels 6502, while application of a control pressure to line 6504b will close the other thirty-two flow channels 6502. Similarly, application of a control pressure to line 6504k will close one set of alternating flow channels 6502, while application of a control pressure to line 6504l will close the other set of alternating flow channels 6502. Thus by selectively applying a control pressure to one line of each control line pairs 6504a-b, 6504c-d, 6504e-f, 6504g-h, 6504i-j, and 6504k-l, the flow of fluid from output 6510 of multiplexer structure 6500 can be limited to a single control channel.

While the above description illustrates a multiplexer having sixty-four flow channels, this is merely one particular embodiment. A multiplexer structure in accordance with the present invention is not limited to any particular number of flow channels. A non-exclusive list of the number of flow channels for a multiplexer structure in accordance with the present invention follows: four, eight, sixteen, thirty-two, sixty-four, ninety-six, one hundred and twenty-eight, two hundred and fifty-six, three hundred and eighty-four, five hundred and twelve, one thousand twenty-four, and one thousand five hundred and thirty-six.

Multiplexer structures comprising number of flow channels other than those listed are also contemplated, so long as the 2($\log_2$ n) relation governing the minimum number of control lines for a given number of flow channels is satisfied. Multiplexer structures having less than 2($\log_2$ n) control lines for n flow lines are also contemplated by the present invention. Such multiplexer structures could generate useful actuation patterns (i.e. 1111000011110000 . . . ) in the flow lines.

While the embodiment of a multiplexer of FIG. 60 shows the use of valve structures in combination with separate pumping structures, this is not required by the present invention. Specifically, regions of control channel/flow channel overlap not otherwise utilized to control flow through a given flow channel can be actuated to pump fluid through the flow channel. This aspect of the present invention is illustrated below in conjunction with FIG. 74.

FIG. 74 shows a plan view of multiplexer structure 7900 comprising at least three parallel flow channels 7902*a-c* overlapped by at least three parallel control channels 7904*a-c*. Overlap of the broad portion of first control channel 7904*a* with first flow channel 7902*a* creates multiplexer valve 7906 controlling flow F1 of material through first flow channel 7902*a*.

Second and third control channels 7904*b*, and 7904*c* merely cross-over first flow channel 7902*a* before widening to control flow F2 and F3 through second and third flow channels 7902*b* and 7902*c* respectively. However, application of a sequence of high pressure signals to control channels 7904*b* and 7904*c*, coordinated with the actuation of multiplexer valve 7906, may cause pumping of fluid down first flow channel 7902*a*.

While, high pressures present within control channels 7904*b* and 7904*c* during pumping of the first flow channel 7902*a* may also actuate multiplexer valves 7908 and 7810 of the second and third flow channels 7902*b* and 7902*c*, closure of other multiplexer valves (not shown) up- or downstream of multiplexer valves 7908 and 7910 would block undesired movement of fluid through flow channels 7902*b* and 7902*c*. As shown in FIG. 60, such additional up- or downstream multiplexer valves would be present in multiplexers controlling even a modest number of flow channels.

The networked structures just described utilize two layers of elastomeric material for controlling the movement of fluid in a single plane. An even greater degree of flexibility in controlling the flow of fluid through channels and chambers can be achieved through the use of more than two elastomer layers. This is illustrated in connection with FIG. 75.

FIG. 75 presents a cross-sectional view of a microfluidic structure in accordance with one embodiment of the present invention, which is formed from three elastomer layers on top of a substrate. Specifically, elastomer device 8000 comprises first elastomer layer 8002 overlying planar substrate 8004 and bearing first recessed control channel 8006. Second elastomer layer 8008 overlies first elastomer layer 8002, and recessed flow channel 8010 of second elastomer layer 8008 is separated from first control channel 8006 by first membrane 8010.

Third elastomer layer 8012 overlies second elastomer layer 8008 and bears second recessed control channel 8014 separated from underlying flow channel 8010 by second membrane 8016. The arrangement of elastomer layers just shown allows control channels 8006 and 8014 to operate independently to control the flow of material through flow channel 8010. The use of control channels both above and below the flow channel confers greater flexiblity to the designer in routing of control signals.

The usefulness of the three-layer structure of FIG. 75 is further illustrated in connection with FIG. 76. FIG. 76 shows a cross-sectional view of a pinch-off valve in accordance with an embodiment of the present invention. First control channel 8100 is defined between a recess in a bottom surface of first elastomer layer 8102 and underlying substrate 8104. Flow channel 8106 is defined between a recess in the bottom surface of second elastomer layer 8108, and the underlying first elastomer layer 8102. Second control channel 8110, aligned over first control channel 8100, is defined between a recess in the bottom surface of third elastomer layer 8112, and the underlying second elastomer layer 8108.

During operation, pressure is simultaneously applied to first and second control channels 8100 and 8110, such that first membrane 8114 and second membrane 8116 are deflected from opposite sides to meet in flow channel 8106. By reducing the degree of deflection necessary to close off the flow channel, the pinch-off valve structure of FIG. 76 permits reduced actuation forces to be employed, or permits less flexible membranes to be employed to close the flow channel.

The valve embodiment of FIG. 76 can be employed to create a multiplexer structure having a reduced number of control lines. FIG. 79 illustrates a simplified plan view of an alternative embodiment of a multiplexer structure in accordance with the present invention.

Multiplexer 8400 comprises a first set of parallel control channels 8402 formed in a first elastomer layer overlying a substrate. Flow channels 8404 are formed in a second elastomer layer overlying the first elastomer layer. A second set of parallel control channels 8406 are formed in a third elastomer layer overlying the second elastomer layer, the second set of control channels 8406 oriented orthogonal to the underlying first set of control channels 8402.

Points of overlap of first control channels 8402, flow channels 8404, and second control channels 8406 create a pinch-off valve 8408 in flow channels 8404. Only upon actuation of both of the control channels 8402 and 8406 will a pinch-off valve 8408 close the flow channel 8404.

FIG. 80A shows a plan view of an alternative embodiment of a valve structure in accordance with the present invention, utilizing control layers positioned on opposite sides of the layer containing the flow channel. FIG. 80B shows a cross-sectional view of the valve structure of FIG. 80A along the line 80B-80B'.

Valve 8500 comprises lower control channel 8502 defined between a recess in first elastomer layer 8504, and underlying planar substrate 8506. Flow channel 8508 is defined between a recess in second elastomer layer 8510 and the top surface of underlying first elastomer layer 8504. Upper control channel 8512 is defined between a recess in third elastomer layer 8514 and the top surface of underlying second elastomer layer 8510.

At first T-junction 8516, flow channel 8508 splits into branches 8508*a* and 8508*b*, each having the same volume as the main flow channel portion 8508. Branches 8508*a* and 8508*b* reunite at second T-junction 8518 to reform main flow channel portion 8508. First flow channel branch 8518*a* only overlies lower control channel 8502. Upper control channel 8512 overlies only second flow channel branch 8508*b*. As a result of the architecture just described, valve 8500 will be closed only when both the lower and upper control channels 8502 and 8512 are actuated. Under any other condition, material will continue to flow through at least one of branches 8508*a* and 8508*b* of flow channel 8508.

The branched valve structure of FIGS. 80A-B can be utilized to create an embodiment of a multiplexer structure requiring only two elastomer layers. FIG. 81 presents a simplified schematic view of such an alternative embodiment of a multiplexer structure. Multiplexer 8600 comprises a lower elastomer layer defining a plurality of flow channels 8602, each flow channel 8602 split into M number of parallel branches 8602a. In the particular multiplexer embodiment shown in FIG. 81, M=2.

An upper elastomer layer overlying the lower elastomer layer defines N number of control channels 8604 orthogonal to flow channel branches 8602a. In the particular multiplexer embodiment shown in FIG. 81, N=6. Control channels 8604 include widened portions creating membranes 8604a that are deflectable into the underlying flow channel branch 8602a. Selective actuation of control channels 8604 allows control over $(N/M)^M$ flow channels.

While FIGS. 75 and 79-80B illustrate embodiments of multilayer elastomeric structures utilizing control channels positioned on opposite sides of the flow channel, the present invention is not limited to this particular configuration. FIG. 77 illustrates an embodiment of a multi-layer microfabricated elastomeric structure in accordance with the present invention, wherein two control channel layers are positioned on the same side of the flow channel.

Specifically, microfabricated elastomer structure 8200 comprises a plurality of parallel flow channels 8202 defined by recesses in a bottom surface of a lowest elastomer layer and an underlying substrate. Flow channels 8202 encounter a series of functional blocks 8204, 8206, and 8208 comprising complex flow networks. An example of the functions performed by blocks 8204, 8206, and 8208 could be the grinding, separation, and analysis of cells flowed down flow lines 8202.

Movement of fluids between functional blocks 8204, 8206, and 8208 is controlled by first set 8210 of control lines defined between a top surface of the underlying elastomer layer and recesses in a bottom surface of an intermediate elastomer layer. The overlap of control lines 8210 and flow channels 8202 defines a plurality of control valves 8212.

Second set 8214 of control lines interacts with each functional block 8204, 8206, and 8208 to control the flow of materials and performance of a specific function. The second set 8214 of control lines are also defined between a top surface of the underlying elastomer layer and recesses in a bottom surface of an intermediate elastomer layer.

In order to simplify the number of control lines and hence reduce the complexity of the microfabricated elastomeric device, functional blocks 8204, 8206, and 8208 are in common communication with second set 8214 of control lines. In order to ensure independent operation of blocks 8204, 8206, and 8208 and maximum flexibility of functionality for device 8200, the second set 8214 of control lines is in turn controlled by third set 8216 of control lines. The third set 8216 of control lines are defined between a top surface of the intermediate elastomer layer and recesses in a bottom surface of a top elastomer layer.

Where actuation of the second set 8214 of control lines is intended to govern functionality of first functional block 8204, lines 8216b and 8216c of third control line set 8216 are actuated, blocking communication of signals by second control line set 8214 to second functional block 8206 and to third functional block 8208. Conversely, where actuation of the second set 8214 of control lines is intended to govern functionality of second functional block 8206, control lines 8216a and 8216c of third control line set 8216 are actuated, blocking communication of signals by second control line set 8214 to first functional block 8206 and to third functional block 8208. Similarly, where actuation of the second set 8214 of control lines is intended to govern functionality of third functional block 8208, control lines 8216a and 8216b of third control line set 8216 are actuated, blocking communication of signals by second control line set 8214 to first functional block 8204 and to second functional block 8206.

The use of one set of control lines to control another set of control lines common to multiple functional blocks, reduces the total number of control lines and control inputs. The overall architecture of the device is thereby simplified, reducing expense.

Selectively Addressable Reaction Chambers Along Flow Lines:

In a further embodiment of the invention, illustrated in FIGS. 28A, 28B, 28C and 28D, a system for selectively directing fluid flow into one more of a plurality of reaction chambers disposed along a flow line is provided.

FIG. 28A shows a top view of a flow channel 30 having a plurality of reaction chambers 80A and 80B disposed therealong. Preferably flow channel 30 and reaction chambers 80A and 80B are formed together as recesses into the bottom surface of a first layer 100 of elastomer.

FIG. 28B shows a bottom plan view of another elastomeric layer 110 with two control lines 32A and 32B each being generally narrow, but having wide extending portions 33A and 33B formed as recesses therein.

As seen in the exploded view of FIG. 28C, and assembled view of FIG. 28D, elastomeric layer 110 is placed over elastomeric layer 100. Layers 100 and 110 are then bonded together, and the integrated system operates to selectively direct fluid flow F (through flow channel 30) into either or both of reaction chambers 80A and 80B, as follows. Pressurization of control line 32A will cause the membrane 25 (i.e.: the thin portion of elastomer layer 100 located below extending portion 33A and over regions 82A of reaction chamber 80A) to become depressed, thereby shutting off fluid flow passage in regions 82A, effectively sealing reaction chamber 80 from flow channel 30. As can also be seen, extending portion 33A is wider than the remainder of control line 32A. As such, pressurization of control line 32A will not result in control line 32A sealing flow channel 30.

As can be appreciated, either or both of control lines 32A and 32B can be actuated at once. When both control lines 32A and 32B are pressurized together, sample flow in flow channel 30 will enter neither of reaction chambers 80A or 80B.

The concept of selectably controlling fluid introduction into various addressable reaction chambers disposed along a flow line (FIG. 28) can be combined with concept of selectably controlling fluid flow through one or more of a plurality of parallel flow lines (FIG. 27) to yield a system in which a fluid sample or samples can be can be sent to any particular reaction chamber in an array of reaction chambers. An example of such a system is provided in FIG. 29, in which parallel control channels 32A, 32B and 32C with extending portions 34 (all shown in phantom) selectively direct fluid flows F1 and F2 into any of the array of reaction wells 80A, 80B, 80C or 80D as explained above; while pressurization of control lines 32C and 32D selectively shuts off flows F2 and F1, respectively.

In yet another novel embodiment, fluid passage between parallel flow channels is possible. Referring to FIG. 30, either or both of control lines 32A or 32D can be depressurized such that fluid flow through lateral passageways 35 (between parallel flow channels 30A and 30B) is permitted. In this aspect of the invention, pressurization of control lines 32C and 32D would shut flow channel 30A between 35A and 35B, and would also shut lateral passageways 35B. As such, flow entering as flow F1 would sequentially travel through 30A, 35A and leave 30B as flow F4.

Switchable Flow Arrays

In yet another novel embodiment, fluid passage can be selectively directed to flow in either of two perpendicular directions. An example of such a "switchable flow array" system is provided in FIGS. 31A to 31D. FIG. 31A shows a bottom view of a first layer of elastomer 90, (or any other suitable substrate), having a bottom surface with a pattern of recesses forming a flow channel grid defined by an array of solid posts 92, each having flow channels passing therearound.

In preferred aspects, an additional layer of elastomer is bound to the top surface of layer 90 such that fluid flow can be selectively directed to move either in direction F1, or perpendicular direction F2. FIG. 31 is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Elastomeric layer 95 is positioned over top of elastomeric layer 90 such that "vertical" control lines 96 are positioned over posts 92 as shown in FIG. 31C and "horizontal" control lines 94 are positioned with their wide portions between posts 92, as shown in FIG. 31D.

As can be seen in FIG. 31C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 31D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIG. 31 allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

Biopolymer Synthesis

The present elastomeric valving structures can also be used in biopolymer synthesis, for example, in synthesizing oligonucleotides, proteins, peptides, DNA, etc. In a preferred aspect, such biopolymer synthesis systems may comprise an integrated system comprising an array of reservoirs, fluidic logic (according to the present invention) for selecting flow from a particular reservoir, an array of channels or reservoirs in which synthesis is performed, and fluidic logic (also according to the present invention) for determining into which channels the selected reagent flows. An example of such a system 200 is illustrated in FIG. 32, as follows.

Four reservoirs 150A, 150B, 150C and 150D have bases A, C, T and G respectively disposed therein, as shown. Four flow channels 30A, 30B, 30C and 30D are connected to reservoirs 150A, 150B, 150C and 150D. Four control lines 32A, 32B, 32C and 32D (shown in phantom) are disposed thereacross with control line 32A permitting flow only through flow channel 30A (i.e.: sealing flow channels 30B, 30C and 30D), when control line 32A is pressurized. Similarly, control line 32B permits flow only through flow channel 30B when pressurized. As such, the selective pressurization of control lines 32A, 32B, 32C and 32D sequentially selects a desired base A, C, T and G from a desired reservoir 150A, 150B, 150C or 150D. The fluid then passes through flow channel 120 into a multiplexed channel flow controller 125, (including, for example, any system as shown in FIGS. 26A to 31D) which in turn directs fluid flow into one or more of a plurality of synthesis channels or chambers 122A, 122B, 122C, 122D or 122E in which solid phase synthesis may be carried out.

FIG. 33 shows a further extension of this system on which a plurality of reservoirs R1 to R13 (which may contain bases A, T, C and G, or any other reactants, such as would be used in combinatorial chemistry), are connected to systems 200 as set forth in FIG. 32. Systems 200 are connected to a multiplexed channel flow controller 125, (including, for example, any system as shown in FIGS. 26A to 31D) which is in turn connected to a switchable flow array (for example as shown in FIG. 31). An advantage of this system is that both of multiplexed channel flow controllers 125 and fluid selection systems 200 can be controlled by the same pressure inputs 170 and 172, provided a "close horizontal" and a "close vertical" control lines (160 and 162, in phantom) are also provided.

In further alternate aspects of the invention, a plurality of multiplexed channel flow controllers (such as 125) may be used, with each flow controller initially positioned stacked above one another on a different elastomeric layer, with vertical vias or interconnects between the elastomer layers (which may be created by lithographically patterning an etch resistant layer on top of a elastomer layer, then etching the elastomer and finally removing the etch resist before adding the last layer of elastomer).

For example, a vertical via in an elastomer layer can be created by etching a hole down onto a raised line on a micromachined mold, and bonding the next layer such that a channel passes over that hole. In this aspect of the invention, multiple synthesis with a plurality of multiplexed channel flow controllers 125 is possible.

The bonding of successive layers of molded elastomer to form a multi-layer structure is shown in FIG. 34, which is an optical micrograph of a section of a test structure composed of seven layers of elastomer. The scale bar of FIG. 34 is 200 µm.

Figure 35D:
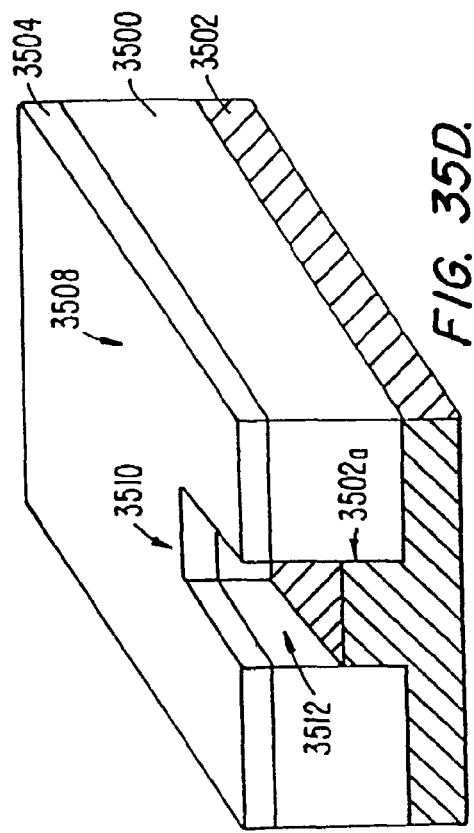
Figure 35C:
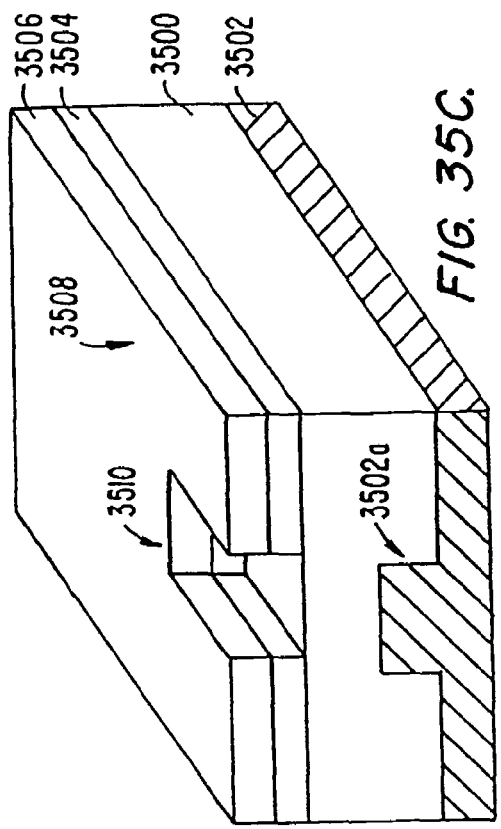
Figure 35B:
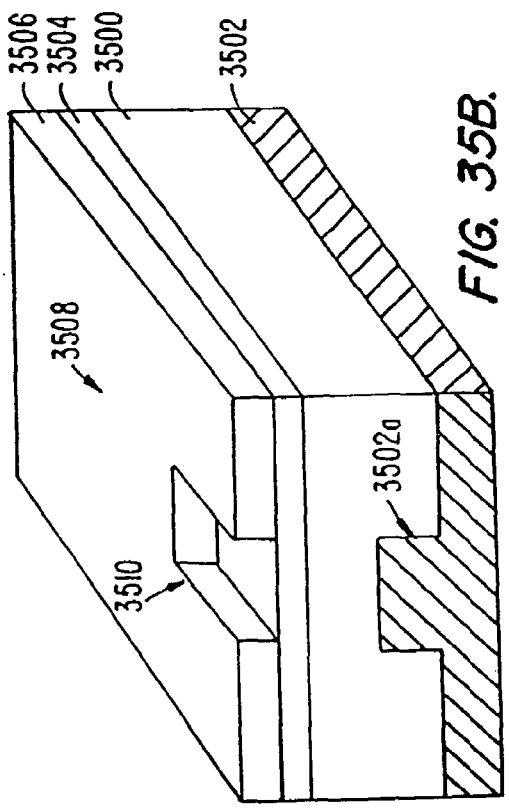
Figure 35A:
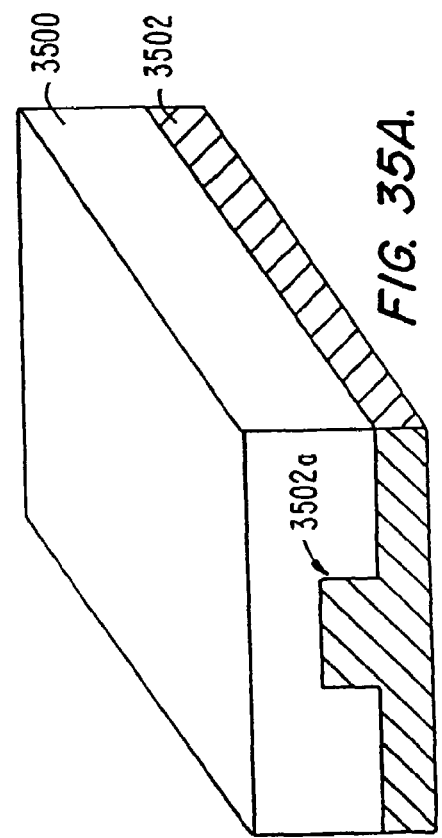

One method for fabricating an elastomer layer having the vertical via feature utilized in a multi-layer structure is shown in FIGS. 35A-35D. FIG. 35A shows formation of elastomer layer 3500 over micromachined mold 3502 including raised line 3502a.

FIG. 35B shows formation of metal etch blocking layer 3504 over elastomer layer 3500, followed by the patterning of photoresist mask 3506 over etch blocking layer 3504 to cover masked regions 3508 and leave exposed unmasked regions 3510. FIG. 35C shows the exposure to solvent which removes etch blocking layer 3504 in unmasked regions 3510.

FIG. 35D shows removal of the patterned photoresist, followed by subsequent etching of underlying elastomer 3500 in unmasked regions 3510 to form vertical via 3512. Subsequent exposure to solvent removes remaining etch blocking layer 3504 in masked regions 3508 selective to the surrounding elastomer 3500 and mold 3502. This elastomer layer may then be incorporated into an elastomer structure by multilayer soft lithography.

This series of steps can be repeated as necessary to form a multi-layered structure having the desired number and orientation of vertical vias between channels of successive elastomer layers.

The inventors of the present invention have succeeded in etching vias through GE RTV 615 layers using a solution of Tetrabutylammonium fluoride in organic solvent. Gold serves as the etch blocking material, with gold removed selective to GE RTV 615 utilizing a $KI/I_2/H_2O$ mixture.

Alternatively, vertical vias between channels in successive elastomer layers could be formed utilizing a negative mask technique. In this approach, a negative mask of a metal foil is patterned, and subsequent formation of an etch blocking layer is inhibited where the metal foil is present. Once the etch blocking material is patterned, the negative metal foil mask is removed, permitting selective etching of the elastomer as described above.

In yet another approach, vertical vias could be formed in an elastomer layer using ablation of elastomer material through application of radiation from an applied laser beam.

In still another approach, vertical vias can be formed by physically punching out a hole in the elastomer material. For example, FIG. 82A shows a cross-sectional view of two layer microfabricated elastomer device 8700 having a flow channel 8702 formed in lower elastomer layer 8704 and a control channel 8706 in an upper elastomer layer 8708. First vertical via 8710 enables fluid communication between control channel 8706 and upper surface 8708a of upper elastomer layer 8708. Second vertical via 8712 enables fluid communication between flow channel 8702 and upper surface 8708a of upper elastomer layer 8708.

FIGS. 82B and 82C show perspective views of steps in the fabrication of the microfabricated elastomer device of FIG. 82A. Specifically, in FIG. 82B, first via 8710 could be formed by coring molded elastomer layer 8708 with rigid hollow member 8714 such as a steel capillary tube, before assembly of the structure. In order to ensure proper alignment between first via 8710 and control channel 8706, upper elastomer layer 8708 could be punctured by the rigid hollow member 8714 from control channel side 8708b.

Vertical vias in communication with the flow channel of the underlying flow channel could then be formed once the molded and cored upper elastomer layer is placed over the lower elastomer layer. Specifically, as shown in FIG. 82C, the second via allowing fluid communication between flow channel 8702 and top surface 8708a of upper elastomer layer 8708 could be formed by punching rigid hollow member 8714 through both lower and upper elastomer layers 8704 and 8708, respectively. Again, starting this coring process from the flow channel side 8704a of the lower elastomer layer 8704 would ensure proper alignment of the second via with flow channel 8702.

Via formation by physical coring or punching of the elastomer material offers a number of advantages. One is simplicity, as placement of the vias is controlled by physical manipulation of the coring device, and complex lithography/etching steps are not required. Another advantage of the coring method is that flexibility of the elastomer allows a rigid tube having a diameter slightly larger than the coring device to be inserted into the via. The cored elastomer will grip the larger-sized tubing, securing it in place within the via and creating a tight seal.

While the above approach is described in connection with the synthesis of biopolymers, the invention is not limited to this application. The present invention could also function in a wide variety of combinatorial chemical synthesis approaches.

Other Applications:

Advantageous applications of the present monolithic microfabricated elastomeric valves and pumps are numerous. Accordingly, the present invention is not limited to any particular application or use thereof. In preferred aspects, the following uses and applications for the present invention are contemplated.

1. Cell/DNA Sorting

The present microfluidic pumps and valves can also be used in flow cytometers for cell sorting and DNA sizing. Sorting of objects based upon size is extremely useful in many technical fields.

For example, many assays in biology require determination of the size of molecular-sized entities. Of particular importance is the measurement of length distribution of DNA molecules in a heterogeneous solution. This is commonly done using gel electrophoresis, in which the molecules are separated by their differing mobility in a gel matrix in an applied electric field, and their positions detected by absorption or emission of radiation. The lengths of the DNA molecules are then inferred from their mobility.

While powerful, electrophoretic methods pose disadvantages. For medium to large DNA molecules, resolution, i.e. the minimum length difference at which different molecular lengths may be distinguished, is limited to approximately 10% of the total length. For extremely large DNA molecules, the conventional sorting procedure is not workable. Moreover, gel electrophoresis is a relatively lengthy procedure, and may require on the order of hours or days to perform.

The sorting of cellular-sized entities is also an important task. Conventional flow cell sorters are designed to have a flow chamber with a nozzle and are based on the principle of hydrodynamic focusing with sheath flow. Most conventional cell sorters combine the technology of piezo-electric drop generation and electrostatic deflection to achieve droplet generation and high sorting rates. However, this approach offers some important disadvantages. One disadvantage is that the complexity, size, and expense of the sorting device requires that it be reusable in order to be cost-effective. Reuse can in turn lead to problems with residual materials causing contamination of samples and turbulent fluid flow.

Therefore, there is a need in the art for a simple, inexpensive, and easily fabricated sorting device which relies upon the mechanical control of fluid flow rather than upon electrical interactions between the particle and the solute.

FIG. 36 shows one embodiment of a sorting device in accordance with the present invention. Sorting device 3600 is formed from a switching valve structure created from channels present in an elastomeric block. Specifically, flow channel 3602 is T-shaped, with stem 3602a of flow channel 3602 in fluid communication with sample reservoir 3604 containing sortable entities 3606 of different types denoted by shape (square, circle, triangle, etc.). Left branch 3602b of flow channel 3602 is in fluid communication with waste reservoir 3608. Right branch 3602c of flow channel 3602 is in communication with collection reservoir 3610.

Control channels 3612a, 3612b, and 3612c overlie and are separated from stem 3602a of flow channel 3602 by elastomeric membrane portions 3614a, 3614b, and 3614c respectively. Together, stem 3602a of flow channel 3602 and control channels 3612a, 3612b, and 3612c form first peristaltic pump structure 3616 similar to that described at length above in connection with FIG. 24a.

Control channel 3612d overlies and is separated from right branch 3602c of flow channel 3602 by elastomeric membrane portion 3614d. Together, right branch 3602c of flow channel 3602 and control channels 3612d forms first valve structure 3618a. Control channel 3612e overlies and is separated from left branch 3602c of flow channel 3602 by elastomeric membrane portion 3614e. Together, left branch 3602c of flow channel 3602 and control channel 3612e forms second valve structure 3618b.

As shown in FIG. 36, stem 3602a of flow channel 3602 narrows considerably as it approaches detection widow 3620 adjacent to the junction of stem 3602a, right branch 3602b, and left branch 3602c. Detection window 3620 is of sufficient width to allow for uniform illumination of this region. In one embodiment, the width of the stem narrows from 100 µm to 5 µm at the detection window. The width of the stem at the detection window can be precisely formed using the soft lithography or photoresist encapsulation fabrication techniques described extensively above, and will be depend upon the nature and size of the entity to be sorted.

Operation of sorting device in accordance with one embodiment of the present invention is as follows.

The sample is diluted to a level such that only a single sortable entity would be expected to be present in the detection window at any time. Peristaltic pump 3616 is activated by flowing a fluid through control channels 3612a-c as described extensively above. In addition, second valve structure 3618b is closed by flowing fluid through control channel 3612e. As a result of the pumping action of peristaltic pump 3616 and the blocking action of second valve 3618b, fluid flows from sample reservoir 3604 through detection window 3620 into waste reservoir 3608. Because of the narrowing of stem 3604, sortable entities present in sample reservoir 3604 are carried by this regular fluid flow, one at a time, through detection window 3620.

Radiation 3640 from source 3642 is introduced into detection window 3620. This is possible due to the transmissive property of the elastomeric material. Absorption or emission of radiation 3640 by sortable entity 3606 is then detected by detector 3644.

If sortable entity 3606a within detection window 3620 is intended to be segregated and collected by sorting device 3600, first valve 3618a is activated and second valve 3618b is deactivated. This has the effect of drawing sortable entity 3606a into collection reservoir 3610, and at the same time transferring second sortable entity 3606b into detection window 3620. If second sortable entity 3602b is also identified for collection, peristaltic pump 3616 continues to flow fluid through right branch 3602c of flow channel 3602 into collection reservoir 3610. However, if second entity 3606b is not to be collected, first valve 3618a opens and second valve 3618b closes, and first peristaltic pump 3616 resumes pumping liquid through left branch 3602b of flow channel 3602 into waste reservoir 3608.

While one specific embodiment of a sorting device and a method for operation thereof is described in connection with FIG. 36, the present invention is not limited to this embodiment. For example, fluid need not be flowed through the flow channels using the peristaltic pump structure, but could instead be flowed under pressure with the elastomeric valves merely controlling the directionality of flow. In yet another embodiment, a plurality of sorting structures could be assembled in series in order to perform successive sorting operations, with the waste reservoir of FIG. 36 simply replaced by the stem of the next sorting structure.

Moreover, a high throughput method of sorting could be employed, wherein a continuous flow of fluid from the sample reservoir through the window and junction into the waste reservoir is maintained until an entity intended for collection is detected in the window. Upon detection of an entity to be collected, the direction of fluid flow by the pump structure is temporarily reversed in order to transport the desired particle back through the junction into the collection reservoir. In this manner, the sorting device could utilize a higher flow rate, with the ability to backtrack when a desired entity is detected. Such an alternative high throughput sorting technique could be used when the entity to be collected is rare, and the need to backtrack infrequent.

Sorting in accordance with the present invention would avoid the disadvantages of sorting utilizing conventional electrokinetic flow, such as bubble formation, a strong dependence of flow magnitude and direction on the composition of the solution and surface chemistry effects, a differential mobility of different chemical species, and decreased viability of living organisms in the mobile medium.

2. Semiconductor Processing

Systems for semiconductor gas flow control, (particularly for epitaxial applications in which small quantities of gases are accurately metered), are also contemplated by the present invention. For example, during fabrication of semiconductor devices solid material is deposited on top of a semiconductor substrate utilizing chemical vapor deposition (CVD). This is accomplished by exposing the substrate to a mixture of gas precursor materials, such that these gases react and the resulting product crystallizes on top of the substrate.

During such CVD processes, conditions must be carefully controlled to ensure uniform deposition of material free of defects that could degrade the operation of the electrical device. One possible source of nonuniformity is variation in the flow rate of reactant gases to the region over the substrate. Poor control of the gas flow rate can also lead to variations in the layer thicknesses from run to run, which is another source of error. Unfortunately, there has been a significant problem in controlling the amount of gas flowed into the processing chamber, and maintaining stable flow rates in conventional gas delivery systems.

Accordingly, FIG. 37A shows one embodiment of the present invention adapted to convey, at precisely-controllable flow rates, processing gas over the surface of a semiconductor wafer during a CVD process. Specifically, semiconductor wafer 3700 is positioned upon wafer support 3702 located within a CVD chamber. Elastomeric structure 3704 containing a large number of evenly distributed orifices 3706 is positioned just above the surface of wafer 3700.

A variety of process gases are flowed at carefully controlled rates from reservoirs 3708a and 3708b, through flow channels in elastomeric block 3704, and out of orifices 3706. As a result of the precisely controlled flow of process gases above wafer 3700, solid material 3710 having an extremely uniform structure is deposited.

Precise metering of reactant gas flow rates utilizing valve and/or pump structures of the present invention is possible for several reasons. First, gases can be flowed through valves that respond in a linear fashion to an applied actuation pressure, as is discussed above in connection with FIGS. 21A and 21B. Alternatively or in addition to metering of gas flow using valves, the predictable behavior of pump structures in accordance with the present invention can be used to precisely meter process gas flow.

In addition to the chemical vapor deposition processes described above, the present technique is also useful to control gas flow in techniques such as molecular beam epitaxy and reactive ion etching.

3. Micro Mirror Arrays

While the embodiments of the present invention described thus far relate to operation of a structure composed entirely of elastomeric material, the present invention is not limited to this type of structure. Specifically, it is within the scope of the present invention to combine an elastomeric structure with a conventional, silicon-based semiconductor structure.

For example, further contemplated uses of the present microfabricated pumps and valves are in optical displays in which the membrane in an elastomeric structure reflects light either as a flat planar or as a curved surface depending upon whether the membrane is activated. As such, the membrane acts as a switchable pixel. An array of such switchable pixels, with appropriate control circuitry, could be employed as a digital or analog micro mirror array.

Accordingly, FIG. 38 shows an exploded view of a portion of one embodiment of a micro mirror array in accordance with the present invention.

Micro mirror array 3800 includes first elastomer layer 3802 overlying and separated from and underlying semiconductor structure 3804 by second elastomer layer 3806. Surface 3804a of semiconductor structure 3804 bears a plurality of electrodes 3810. Electrodes 3810 are individually addressable through conducting row and column lines, as would be known to one of ordinary skill in the art.

First elastomeric layer 3802 includes a plurality of intersecting channels 3822 underlying an electrically conducting, reflecting elastomeric membrane portion 3802a. First elastomeric layer 3802 is aligned over second elastomeric layer 3806 and underlying semiconductor device 3804 such that points of intersection of channels 3822 overlie electrodes 3810.

In one embodiment of a method of fabrication in accordance with the present invention, first elastomeric layer 3822 may be formed by spincoating elastomeric material onto a mold featuring intersecting channels, curing the elastomer, removing the shaped elastomer from the mold, and introducing electrically conducting dopant into surface region of the shaped elastomer. Alternatively as described in connection with FIGS. 7C-7G above, first elastomeric layer 3822 may be formed from two layers of elastomer by inserting elastomeric material into a mold containing intersecting channels such that the elastomeric material is flush with the height of the channel walls, and then bonding a separate doped elastomer layer to the existing elastomeric material to form a membrane on the top surface.

Alternatively, the first elastomeric layer 3802 may be produced from electrically conductive elastomer, where the electrical conductivity is due either to doping or to the intrinsic properties of the elastomer material.

During operation of reflecting structure 3800, electrical signals are communicated along a selected row line and column line to electrode 3810a. Application of voltage to electrode 3810a generates an attractive force between electrode 3810a and overlying membrane 3802a. This attractive force actuates a portion of membrane 3802a, causing this membrane portion to flex downward into the cavity resulting from intersection of the channels 3822. As a result of distortion of membrane 3802a from planar to concave, light is reflected differently at this point in the surface of elastomer structure 3802 than from the surrounding planar membrane surface. A pixel image is thereby created.

The appearance of this pixel image is variable, and may be controlled by altering the magnitude of voltage applied to the electrode. A higher voltage applied to the electrode will increase the attractive force on the membrane portion, causing further distortion in its shape. A lower voltage applied to the electrode will decrease the attractive force on the membrane, reducing distortion in its shape from the planar. Either of these changes will affect the appearance of the resulting pixel image.

A variable micro mirror array structure as described could be used in a variety of applications, including the display of images. Another application for a variable micro mirror array structure in accordance with an embodiment of the present invention would be as a high capacity switch for a fiber optics communications system, with each pixel capable of affecting the reflection and transfer of a component of an incident light signal.

While the above embodiment describes a composite, elastomer/semiconductor structure that is utilized as a miromirror array, the present invention is not limited to this particular embodiment.

For example, another optical application for embodiments of the present invention relate to switchable Bragg mirrors. Bragg mirrors reflect a specific range of wavelengths of incident light, allowing all other wavelengths to pass. A Bragg mirror in accordance with an embodiment of the present invention was fabricated by sputter depositing a mirror comprising thirty alternating 1 µm thick layers of SiO and $Si_3N_4$ over a 30 µm thick RTV elastomer membrane, that in turn overlied a control channel having a depth of 10 µm and a width of 100 µm. Following passivation of the mirror surface with additional RTV elastomer, application of a control pressure of 15 psi to the control channel caused the membrane to deform and allows certain wavelengths to pass. This result is shown in FIG. 65, which plots intensity of light at 490 nm passing through the mirror versus switching cycle. A Bragg mirror in accordance with embodiments of the present invention could be utilized for a variety of purposes, including optical filtering.

4. Refracting Structures

The micro-mirror array structure just described controls reflection of incident light. However, the present invention is not limited to controlling reflection. Yet another embodiment of the present invention enables the exercise of precise control over refraction of incident light in order to create lens and filter structures.

FIG. 39 shows one embodiment of a refractive structure in accordance with the present invention. Refractive structure 3900 includes first elastomeric layer 3902 and second elastomeric layer 3904 composed of elastomeric material capable of transmitting incident light 3906.

First elastomeric layer 3902 has convex portion 3902a which may be created by curing elastomeric material formed over a micromachined mold having a concave portion. Second elastomeric layer 3904 has a flow channel 3905 and may be created from a micromachined mold having a raised line as discussed extensively above.

First elastomer layer 3902 is bonded to second elastomer layer 3904 such that convex portion 3902a is positioned above flow channel 3905. This structure can serve a variety of purposes.

For example, light incident to elastomeric structure 3900 would be focused into the underlying flow channel, allowing the possible conduction of light through the flow channel. Alternatively, in one embodiment of an elastomeric device in accordance with the present invention, fluorescent or phosphorescent liquid could be flowed through the flow channel, with the resulting light from the fluid refracted by the curved surface to form a display.

FIG. 40 shows another embodiment of a refractive structure in accordance with the present invention. Refractive structure 4000 is a multilayer optical train based upon a Fresnel lens design. Specifically, refractive structure 4000 is composed of four successive elastomer layers 4002, 4004, 4006, and 4008, bonded together. The upper surfaces of each of first, second, and third elastomer layers 4002, 4004, and 4006 bear uniform serrations 4010 regularly spaced by a distance X that is much larger than the wavelength of the incident light. Serrations 4010 serve to focus the incident light, and may be formed through use of a micromachined mold as described extensively above. First, second, and third elastomer layers 4002, 4004, and 4006 function as Fresnel lenses as would be understood of one of ordinary skill in the art.

Fourth elastomeric layer 4008 bears uniform serrations 4012 having a much smaller size than the serrations of the overlying elastomeric layers. Serrations 4012 are also spaced apart by a much smaller distance Y than the serrations of the overlying elastomeric layers, with Y on the order of the wavelength of incident light such that elastomeric layer 4008 functions as a diffraction grating.

FIG. 41 illustrates an embodiment of a refractive structure in accordance with the present invention which utilizes difference in material refractive index to primarily accomplish diffraction. Refractive structure 4100 includes lower elastomeric portion 4102 covered by upper elastomeric portion 4104. Both lower elastomeric portion 4102 and upper elastomeric portion 4104 are composed of material transmitting incident light 4106. Lower elastomeric portion 4102 includes a plurality of serpentine flow channels 4108 separated by elastomeric lands 4110. Flow channels 4108 include fluid 4112 having a different refractive index than the elastomeric material making up lands 4110. Fluid 4112 is pumped through serpentine flow channels 4108 by the operation of pump structure 4114 made up of parallel control channels 4116*a* and 4116*b* overlying and separated from inlet portion 4108*a* of flow channel 4108 by moveable membrane 4118.

Light 4106 incident to refractive structure 4100 encounters a series of uniformly-spaced fluid-filled flow channels 4108 separated by elastomeric lands 4110. As a result of the differing optical properties of material present in these respective fluid/elastomer regions, portions of the incident light are not uniformly refracted and interact to form an interference pattern. A stack of refractive structures of the manner just described can accomplish even more complex and specialized refraction of incident light.

The refractive elastomeric structures just described can fulfill a variety of purposes. For example, the elastomeric structure could act as a filter or optical switch to block selected wavelengths of incident light. Moreover, the refractive properties of the structure could be readily adjusted depending upon the needs of a particular application.

For example, the composition (and hence refractive index) of fluid flowed through the flow channels could be changed to affect diffraction. Alternatively, or in conjunction with changing the identity of the fluid flowed, the distance separating adjacent flow channels can be precisely controlled during fabrication of the structure in order to generate an optical interference pattern having the desired characteristics.

Yet another application involving refraction by embodiments in accordance with the present invention is a tunable microlens structure. As shown in FIG. 66, tunable microlens structure 7100 comprises chamber 7102 connected to pneumatic control line 7104. Chamber 7102 may be formed by soft lithography of a transparent substrate such as RTV, which is then bonded to elastomer membrane 7106. Chamber 7102 is then filled with a fluid 7103 chosen for its index of refraction. When control line 7104 line is pressurized, membrane 7106 expands in a bulb over chamber 7102, creating a lens. Radius R of curvature of membrane 7106, and hence the focal length of the lens, may be controlled by varying the pressure in control line 7104 and therefore tuning the lens. Possible applications of such a lens might be the separate interrogation of different channel layers, or the scanning of a bulk sample. Since defining the lens structure is accomplished using photolithography, such lenses may be fabricated inexpensively and may be densely integrated on a fluidics device. Lenses may be made in a wide range of sizes, with diameters varying from 1 µm to 1 cm. Alignment issues are significantly reduced since lateral alignment is achieved by lithography, and vertical alignment is achieved by tuning.

5. Normally-Closed Valve Structure

FIGS. 7B and 7H above depict a valve structure in which the elastomeric membrane is moveable from a first relaxed position to a second actuated position in which the flow channel is blocked. However, the present invention is not limited to this particular valve configuration.

FIGS. 42A-42J show a variety of views of a normally-closed valve structure in which the elastomeric membrane is moveable from a first relaxed position blocking a flow channel, to a second actuated position in which the flow channel is open, utilizing a negative control pressure.

Figure 42A:
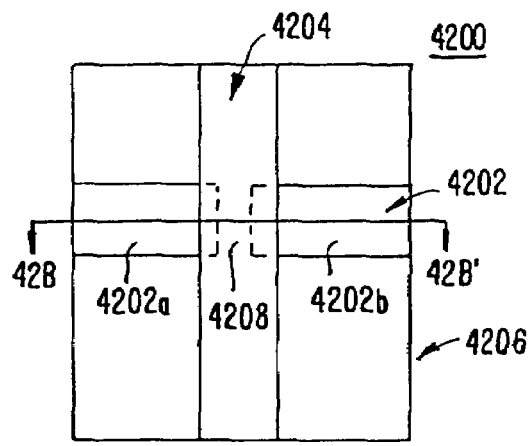
Figure 42D:
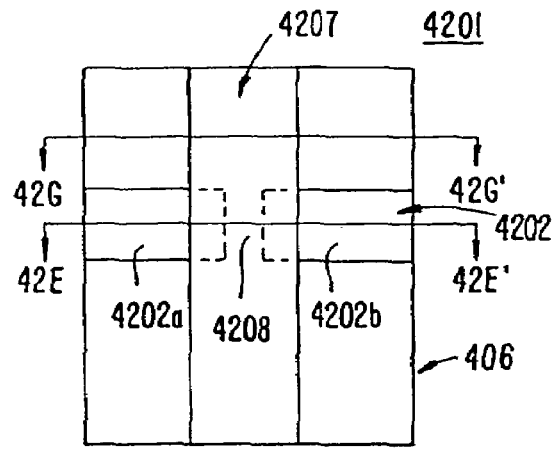
Figure 42B:
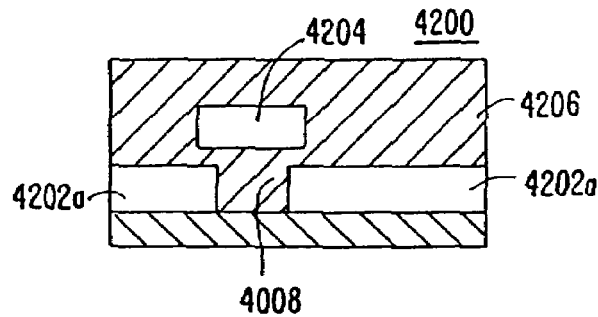
Figure 42E:
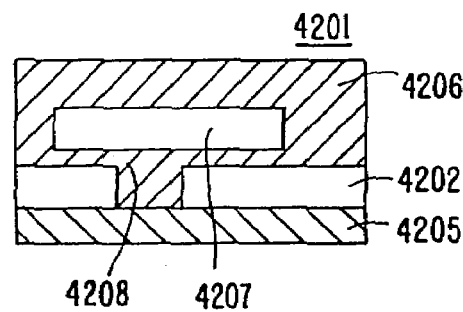

FIG. 42A shows a plan view, and FIG. 42B shows a cross sectional view along line 42B-42B', of normally-closed valve 4200 in an unactuated state. Flow channel 4202 and control channel 4204 are formed in elastomeric block 4206 overlying substrate 4205. Flow channel 4202 includes a first portion 4202*a* and a second portion 4202*b* separated by separating portion 4208. Control channel 4204 overlies separating portion 4208. As shown in FIG. 42B, in its relaxed, unactuated position, separating portion 4008 remains positioned between flow channel portions 4202*a* and 4202*b*, interrupting flow channel 4202.

Figure 42C:
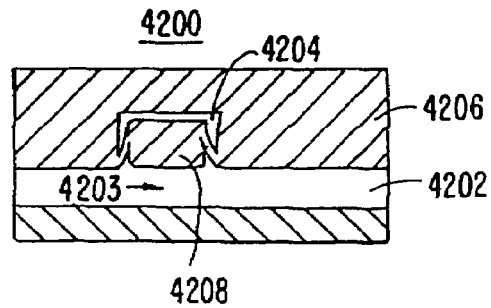
Figure 42F:
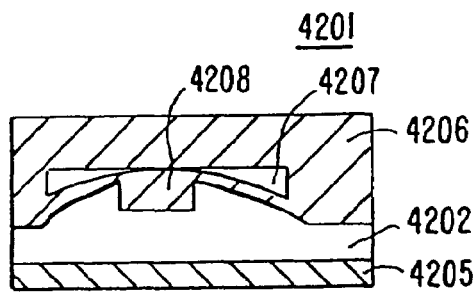

FIG. 42C shows a cross-sectional view of valve 4200 wherein separating portion 4208 is in an actuated position. When the pressure within control channel 4204 is reduced to below the pressure in the flow channel (for example by vacuum pump), separating portion 4208 experiences an actuating force drawing it into control channel 4204. As a result of this actuation force membrane 4208 projects into control channel 4204, thereby removing the obstacle to a flow of material through flow channel 4202 and creating a passageway 4203. Upon elevation of pressure within control channel 4204, separating portion 4208 will assume its natural position, relaxing back into and obstructing flow channel 4202.

The behavior of the membrane in response to an actuation force may be changed by varying the width of the overlying control channel. Accordingly, FIGS. 42D-42H show plan and cross-sectional views of an alternative embodiment of a normally-closed valve 4201 in which control channel 4207 is substantially wider than separating portion 4208. As shown in cross-sectional views FIG. 42E-F along line 42E-42E' of FIG. 42D, because a larger area of elastomeric material is required to be moved during actuation, the actuation force necessary to be applied is reduced.

Figure 42I:
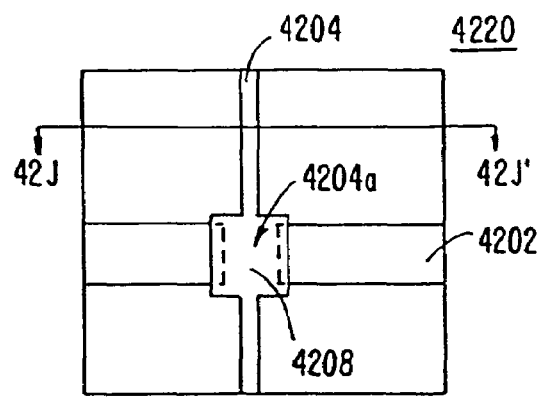
Figure 42G:
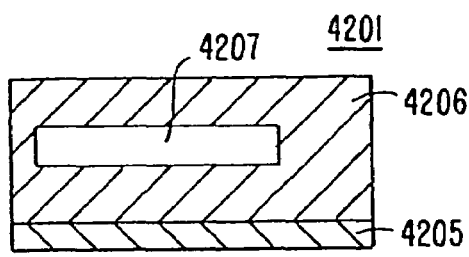
Figure 42J:
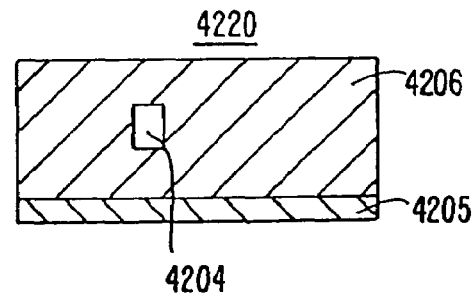
Figure 42H:
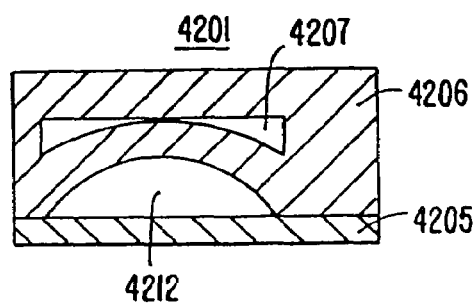

FIGS. 42G and H show a cross-sectional views along line 40G-40G' of FIG. 40D. In comparison with the unactuated valve configuration shown in FIG. 42G, FIG. 42H shows that reduced pressure within wider control channel 4207 may under certain circumstances have the unwanted effect of pulling underlying elastomer 4206 away from substrate 4205, thereby creating undesirable void 4212.

Accordingly, FIG. 42I shows a plan view, and 42J a cross-sectional view along line 42J-42J' of FIG. 42I, of valve structure 4220 which avoids this problem by featuring control line 4204 with a minimum width except in segment 4204a overlapping separating portion 4208. As shown in FIG. 42J, even under actuated conditions the narrower cross-section of control channel 4204 reduces the attractive force on the underlying elastomer material 4206, thereby preventing this elastomer material from being drawn away from substrate 4205 and creating an undesirable void.

While a normally-closed valve structure actuated in response to pressure is shown in FIGS. 42A-42J, a normally-closed valve in accordance with the present invention is not limited to this configuration. For example, the separating portion obstructing the flow channel could alternatively be manipulated by electric or magnetic fields, as described extensively above.

6. Separation of Materials

In a further application of the present invention, an elastomeric structure can be utilized to perform separation of materials. FIG. 43 shows one embodiment of such a device.

Separation device 4300 features an elastomeric block 4301 including fluid reservoir 4302 in communication with flow channel 4304. Fluid is pumped from fluid reservoir 4306 through flow channel 4308 by peristaltic pump structure 4310 formed by control channels 4312 overlying flow channel 4304, as has been previously described at length. Alternatively, where a peristaltic pump structure in accordance with the present invention is unable to provide sufficient back pressure, fluid from a reservoir positioned outside the elastomeric structure may be pumped into the elastomeric device utilizing an external pump.

Flow channel 4304 leads to separation column 4314 in the form of a channel packed with separation matrix 4316 behind porous frit 4318. As is well known in the art of chromatography, the composition of the separation matrix 4316 depends upon the nature of the materials to be separated and the particular chromatography technique employed. The elastomeric separation structure is suitable for use with a variety of chromatographic techniques, including but not limited to gel exclusion, gel permeation, ion exchange, reverse phase, hydrophobic interaction, affinity chromatography, fast protein liquid chromatography (FPLC) and all formats of high pressure liquid chromatography (HPLC). The high pressures utilized for HPLC may require the use of urethane, dicyclopentadiene or other elastomer combinations.

Samples are introduced into the flow of fluid into separation column 4314 utilizing load channel 4319. Load channel 4319 receives fluid pumped from sample reservoir 4320 through pump 4321. Upon opening of valve 4322 and operation of pump 4321, sample is flowed from load channel 4319 into flow channel 4304. The sample is then flowed through separation column 4314 by the action of pump structure 4312. As a result of differential mobility of the various sample components in separation matrix 4316, these sample components become separated and are eluted from column 4314 at different times.

Upon elution from separation column 4314, the various sample components pass into detection region 4324. As is well known in the art of chromatography, the identity of materials eluted into detection region 4324 can be determined utilizing a variety of techniques, including but not limited to fluorescence, UV/visible/IR spectroscopy, radioactive labeling, amperometric detection, mass spectroscopy, and nuclear magnetic resonance (NMR).

A separation device in accordance with the present invention offers the advantage of extremely small size, such that only small volumes of fluid and sample are consumed during the separation. In addition, the device offers the advantage of increased sensitivity. In conventional separation devices, the size of the sample loop will prolong the injection of the sample onto the column, causing width of the eluted peaks to potentially overlap with one another. The extremely small size and capacity of the load channel in general prevents this peak diffusion behavior from becoming a problem.

The separation structure shown in FIG. 43 represents only one embodiment of such a device, and other structures are contemplated by the present invention. For example, while the separation device of FIG. 43 features a flow channel, load loop, and separation column oriented in a single plane, this is not required by the present invention. One or more of the fluid reservoir, the sample reservoir, the flow channel, the load loop, and the separation column could be oriented perpendicular to one another and/or to the plane of the elastomeric material utilizing via structures whose formation is described at length above in connection with FIG. 35A-D.

7. Cell Pen/Cell Cage/Cell Grinder

In yet a further application of the present invention, an elastomeric structure can be utilized to manipulate organisms or other biological material. FIGS. 44A-44D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 44C:
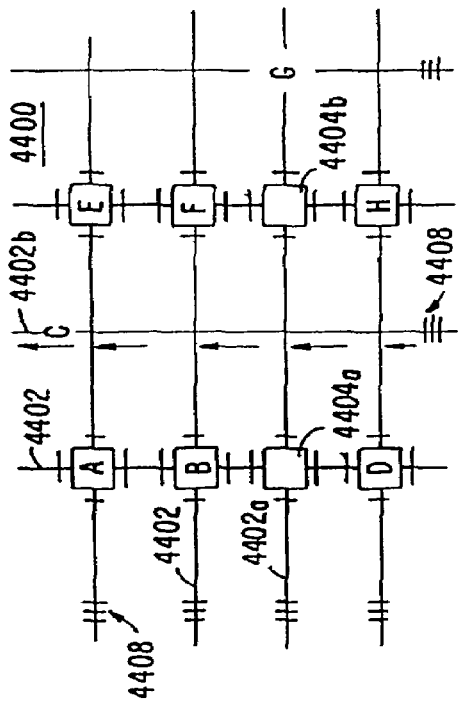
Figure 44D:
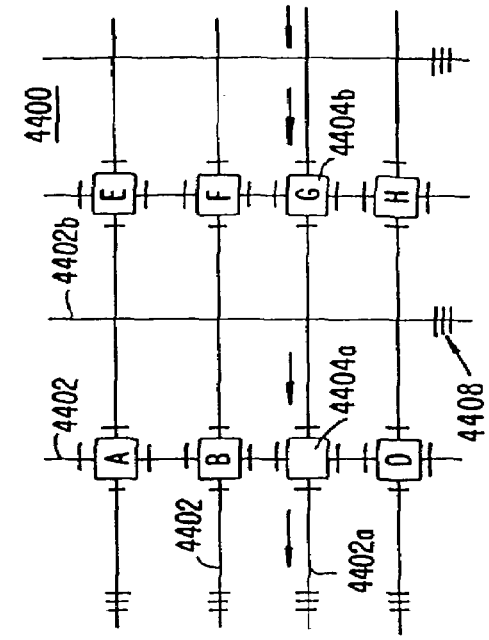
Figure 44A:
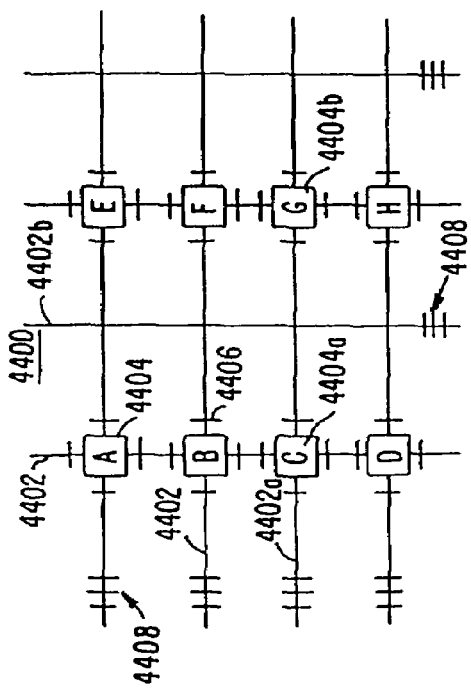
Figure 44B:
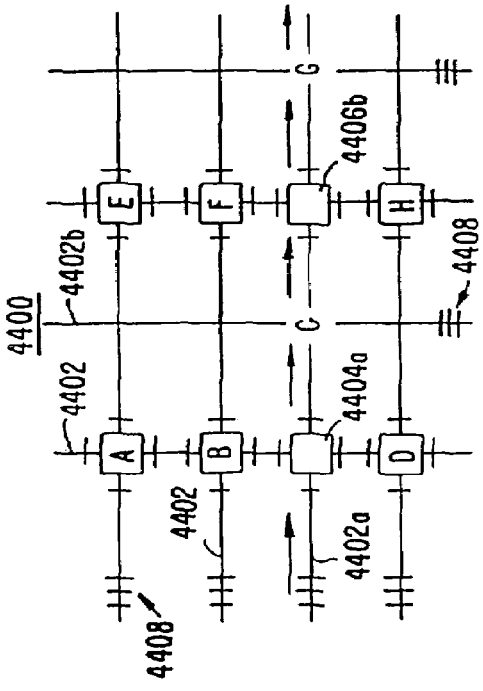

Cell pen array 4400 of FIG. 44A has been loaded with cells A-H that have been previously sorted, perhaps by a sorting structure as described above in conjunction with FIG. 36. FIGS. 44B-44C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 44D shows that second cell G is moved back into its prior position in cell pen array 4400 by reversing the direction of liquid flow through horizontal flow channel 4402a.

The cell pen array 4404 described above is capable of storing materials within a selected, addressable position for ready access. However, living organisms such as cells may require a continuous intake of foods and expulsion of wastes in order to remain viable. Accordingly, FIGS. 45A and 45B show plan and cross-sectional views (along line 45B-45B') respectively, of one embodiment of a cell cage structure in accordance with the present invention.

Cell cage 4500 is formed as an enlarged portion 4500a of a flow channel 4501 in an elastomeric block 4503 in contact with substrate 4505. Cell cage 4500 is similar to an individual cell pen as described above in FIGS. 44A-44D, except that ends 4500b and 4500c of cell cage 4500 do not completely enclose interior region 4500a. Rather, ends 4500a and 4500b of cage 4500 are formed by a plurality of retractable pillars 4502. Pillars 4502 may be part of a membrane structure of a normally-closed valve structure as described extensively above in connection with FIGS. 42A-42J.

Specifically, control channel 4504 overlies pillars 4502. When the pressure in control channel 4504 is reduced, elastomeric pillars 4502 are drawn upward into control channel 4504, thereby opening end 4500b of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500a in order to sustain cell(s) stored therein. Pillars 4502 on opposite end 4500c are similarly configured beneath second control channel 4506 to permit opening of the cage and removal of the cell as desired.

Under certain circumstances, it may be desirable to grind/disrupt cells or other biological materials in order to access component pieces.

Accordingly, FIGS. 46A and 46B show plan and cross sectional views (along line 46B-46B') respectively, of one embodiment of cell grinder structure 4600 in accordance with the present invention. Cell grinder 4600 includes a system of interdigitated posts 4602 within flow channel 4604 which close together upon actuation of integral membrane 4606 by overlying control channel 4608. By closing together, posts 4602 crush material present between them.

Posts 4602 may be spaced at intervals appropriate to disrupt entities (cells) of a given size. For disruption of cellular material, spacing of posts 4602 at an interval of about 2 µm is appropriate. In alternative embodiments of a cell grinding structure in accordance with the present invention, posts 4602 may be located entirely on the above-lying membrane, or entirely on the floor of the control channel.

The cross-flow channel architecture illustrated shown in FIGS. 44A-44D can be used to perform functions other than the cell pen just described. For example, the cross-flow channel architecture can be utilized in mixing applications.

This is shown in FIGS. 69A-B, which illustrate a plan view of mixing steps performed by a microfabricated structure in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

As shown in FIG. 69A, valve pair 7408a-b is initially opened while valve pair 7408c-d is closed, and fluid sample 7410 is flowed to intersection 7412 through flow channel 7402. Valve pair 7408c-d is then actuated, trapping fluid sample 7410 at intersection 7412.

Next, as shown in FIG. 69B, valve pairs 7408a-b and 7408c-d are opened, such that fluid sample 7410 is injected from intersection 7412 into flow channel 7404 bearing a cross-flow of fluid. The process shown in FIGS. 69A-B can be repeated to accurately dispense any number of fluid samples down cross-flow channel 7404.

The cross-flow injection structure illustrated in FIGS. 69A-69B includes two sets of control lines, one for controlling the valve pairs disposed along each axis. However, in certain applications it may be valuable to be able to independently actuate valves positioned along the flow channels.

In order to accomplish such independent valve actuation, it may be useful to form the elastomeric structure from three elastomer layers. This embodiment is illustrated in connection with FIG. 78, which shows a plan view of a row of a flow channel array featuring independently-controllable valves.

Specifically, flow channel array 8300 comprises a first set of parallel flow channels 8304 and second set of parallel flow channels 8306 (only one of which is shown in FIG. 77) formed in an intermediate elastomer layer. Intersection of the first parallel flow channels 8304 with the second parallel flow channels 8306 defines an array of junctions 8308.

Each flow channel junction 8308 is surrounded by valves 8310 governing the flow of material into and out of the junction. First and second control channels 8312 and 8314 are defined by recesses in a first elastomer layer that underlies the intermediate elastomer layer and overlies a substrate. The overlap of flow channel 8304 over first control channel 8312 defines bottom valves 8310a. The overlap of flow channel 8306 over second control channel 8314 defines left valves 8310b.

Third and fourth control channels 8316 and 8318 are defined by recesses in a second elastomer layer that overlies the intermediate elastomer layer. The overlap of third control channel 8316 and flow channel 8304 defines top valves 8310c. The overlap of fourth control channel 8318 and flow channel 8306 defines right valves 8310d.

During operation of structure 8300, first material 8320 may be flowed along flow channels 8306 while top and bottom valves 8310c and 8310a remain closed. Next, right and left valves 8310d, 8310b may be closed, trapping material 8320 in inter-junction regions 8306a of flow channels 8306. Upon opening of top and bottom valves 8310c and 8310a, second material 8324 may be flowed along flow channels 8306.

Fourth control channel 8318 may then be deactuated, selectively opening right valves 8310d, and thereby placing the second material 8324 present at junctions 8308 in contact with the first material 8322 present in inter-junction regions 8306a of flow channels 8306. In the manner just described, the intersection of perpendicular sets of parallel flow channels may be utilized to create an array of segregated chemical environments. One application for such a structure is in high throughput crystallization of materials, as described below.

Independent control over each of the valves surrounding a flow channel junction (as described in FIG. 77) would be difficult to achieve utilizing a structure formed from only two elastomer layers, owing to an inability to provide independently actuatable, non-intersecting control lines in a single elastomer layer. The provision of control lines both above and below a flow channel thus may enable design and fabrication of flow structures exhibiting a complexity and flexibility of operation not realizable utilizing only a single control layer.

8. Pressure Oscillator

In yet a further application of the present invention, an elastomeric structure can be utilized to create a pressure oscillator structure analogous to oscillator circuits frequently employed in the field of electronics. FIG. 47 shows a plan view of one embodiment of such a pressure oscillator structure.

Pressure oscillator 4700 comprises an elastomeric block 4702 featuring flow channel 4704 formed therein. Flow channel 4704 includes an initial portion 4704a proximate to pressure source 4706, and a serpentine portion 4704b distal from pressure source 4706. Initial portion 4704a is in contact with via 4708 in fluid communication with control channel 4710 formed in elastomeric block 4702 above the level of flow channel 4704. At a location more distal from pressure source 4706 than via 4708, control channel 4710 overlies and is separated from flow channel 4704 by an elastomeric membrane, thereby forming valve 4712 as previously described.

Pressure oscillator structure 4700 operates as follows. Initially, pressure source 4706 provides pressure along flow channel 4704 and control channel 4710 through via 4708. Because of the serpentine shape of flow channel 4704*b*, pressure is lower in region 4704*b* as compared with flow channel 4710. At valve 4712, the pressure difference between serpentine flow channel portion 4704*b* and overlying control channel 4710 eventually causes the membrane of valve 4712 to project downward into serpentine flow channel portion 4704*b*, closing valve 4712. Owing to the continued operation of pressure source 4706 however, pressure begins to build up in serpentine flow channel portion 4704*b* behind closed valve 4712. Eventually the pressure equalizes between control channel 4710 and serpentine flow channel portion 4704*b*, and valve 4712 opens.

Given the continuos operation of the pressure source, the above-described build up and release of pressure will continue indefinitely, resulting in a regular oscillation of pressure. Such a pressure oscillation device may perform any number of possible functions, including but not limited to timing.

9. Side-Actuated Valve

While the above description has focused upon microfabricated elastomeric valve structures in which a control channel is positioned above and separated by an intervening elastomeric membrane from an underlying flow channel, the present invention is not limited to this configuration. FIGS. 48A and 48B show plan views of one embodiment of a side-actuated valve structure in accordance with one embodiment of the present invention.

FIG. 48A shows side-actuated valve structure 4800 in an unactuated position. Flow channel 4802 is formed in elastomeric layer 4804. Control channel 4806 abutting flow channel 4802 is also formed in elastomeric layer 4804. Control channel 4806 is separated from flow channel 4802 by elastomeric membrane portion 4808. A second elastomeric layer (not shown) is bonded over bottom elastomeric layer 4804 to enclose flow channel 4802 and control channel 4806.

FIG. 48B shows side-actuated valve structure 4800 in an actuated position. In response to a build up of pressure within control channel 4806, membrane 4808 deforms into flow channel 4802, blocking flow channel 4802. Upon release of pressure within control channel 4806, membrane 4808 would relax back into control channel 4806 and open flow channel 4802.

While a side-actuated valve structure actuated in response to pressure is shown in FIGS. 48A and 48B, a side-actuated valve in accordance with the present invention is not limited to this configuration. For example, the elastomeric membrane portion located between the abutting flow and control channels could alternatively be manipulated by electric or magnetic fields, as described extensively above.

10. Additional Applications

The following represent further aspects of the present invention: present valves and pumps can be used for drug delivery (for example, in an implantable drug delivery device); and for sampling of biological fluids (for example, by storing samples sequentially in a column with plugs of spacer fluid therebetween, wherein the samples can be shunted into different storage reservoirs, or passed directly to appropriate sensor(s). Such a fluid sampling device could also be implanted in the patient's body.

The present systems can also be used for devices which relieve over-pressure in vivo using a micro-valve or pump. For example, an implantable bio-compatible micro-valve can be used to relieve over-pressures in the eye which result from glaucoma. Other contemplated uses of the present switchable micro-valves include implantation in the spermatic duct or fallopian tube allowing reversible long-term or short-term birth control without the use of drugs.

Further uses of the present invention include DNA sequencing whereby the DNA to be sequenced is provided with a polymerase and a primer, and is then exposed to one type of DNA base (A, C, T, or G) at a time in order to rapidly assay for base incorporation. In such a system, the bases must be flowed into the system and excess bases washed away rapidly. Pressure driven flow, gated by elastomeric micro-valves in accordance with the present invention would be ideally suited to allow for such rapid flow and washing of reagents.

Other contemplated uses of the present micro-valve and micro-pump systems include uses with DNA chips. For example, a sample can be flowed into a looped channel and pumped around the loop with a peristaltic action such that the sample can make many passes over the probes of the DNA array. Such a device would give the sample that would normally be wasted sitting over the non-complimentary probes the chance to bind to a complimentary probe instead. An advantage of such a looped-flow system is that it would reduce the necessary sample volume, and thereby increase assay sensitivity.

Further applications exist in high throughput screening in which applications could benefit by the dispensing of small volumes of liquid, or by bead-based assays wherein ultrasensitive detection would substantially improve assay sensitivity.

Another contemplated application is the deposition of array of various chemicals, especially oligonucleotides, which may or may not have been chemically fabricated in a previous action of the device before deposition in a pattern or array on a substrate via contact printing through fluid channel outlets in the elastomeric device in close proximity to a desired substrate, or by a process analogous to ink-jet printing.

The present microfabricated elastomeric valves and pumps could also be used to construct systems for reagent dispensing, mixing and reaction for synthesis of oligonucleotides, peptides or other biopolymers.

Further applications for the present invention include ink jet printer heads, in which small apertures are used to generate a pressure pulse sufficient to expel a droplet. An appropriately actuated micro-valve in accordance with the present invention can create such a pressure pulse. The present micro-valves and pumps can also be used to digitally dispense ink or pigment, in amounts not necessarily as small as single droplets. The droplet would be brought into contact with the medium being printed on rather than be required to be fired through the air.

Yet further uses of the present invention would take advantage of the ready removal and reattachment of the structure from an underlying substrate such as glass, utilizing a glass substrate patterned with a binding or other material. This allows separate construction of a patterned substrate and elastomer structure. For instance, a glass substrate could be patterned with a DNA microarray, and an elastomer valve and pump structure sealed over the array in a subsequent step.

11. Additional Aspects of the Invention

The following represent further aspects of the present invention: the use of a deflectable membrane to control flow of a fluid in a microfabricated channel of an elastomeric structure; the use of elastomeric layers to make a microfabricated elastomeric device containing a microfabricated movable portion; and the use of an elastomeric material to make a microfabricated valve or pump.

A miciofabricated elastomeric structure in accordance with one embodiment of the present invention comprises an elastomeric block formed with microfabricated recesses therein, a portion of the elastomeric block deflectable when the portion is actuated. The recesses comprise a first microfabricated channel and a first microfabricated recess, and the portion comprises an elastomeric membrane deflectable into the first microfabricated channel when the membrane is actuated. The recesses have a width in the range of 10 µm to 200 µm and the portion has a thickness of between about 2 µm and 50 µm. The microfabricated elastomeric structure may be actuated at a speed of 100 Hz or greater and contains substantially no dead volume when the portion is actuated.

A method of actuating an elastomeric structure comprises providing an elastomeric block formed with first and second microfabricated recesses therein, the first and second microfabricated recesses separated by a membrane portion of the elastomeric block deflectable into one of the first and second recesses in response to an actuation force, and applying an actuation force to the membrane portion such that the membrane portion is deflected into one of the first and the second recesses.

A method of microfabricating an elastomeric structure in accordance with one embodiment of the present invention comprises forming a first elastomeric layer on a substrate, curing the first elastomeric layer, and patterning a first sacrificial layer over the first elastomeric layer. A second elastomeric layer is formed over the first elastomeric layer, thereby encapsulating the first patterned sacrificial layer between the first and second elastomeric layers, the second elastomeric layer is cured, and the first patterned sacrificial layer is removed selective to the first elastomeric layer and the second elastomeric layer, thereby forming at least one first recess between the first and second layers of elastomer.

An alternative embodiment of a method of fabricating further comprises patterning a second sacrificial layer over the substrate prior to forming the first elastomeric layer, such that the second patterned sacrificial layer is removed during removal of the first patterned sacrificial layer to form at least one recess along a bottom of the first elastomeric layer.

A microfabricated elastomeric structure in accordance with one embodiment of the present invention comprises an elastomeric block, a first channel and a second channel separated by a separating portion of the elastomeric structure, and a microfabricated recess in the elastomeric block adjacent to the separating portion such that the separating portion may be actuated to deflect into the microfabricated recess. 66. Deflection of the separating portion opens a passageway between the first and second channels.

A method of controlling fluid or gas flow through an elastomeric structure comprises providing an elastomeric block, the elastomeric block having first, second, and third microfabricated recesses, and the elastomeric block having a first microfabricated channel passing therethrough, the first, second and third microfabricated recesses separated from the first channel by respective first, second and third membranes deflectable into the first channel, and deflecting the first, second and third membranes into the first channel in a repeating sequence to peristaltically pump a flow of fluid through the first channel.

A method of microfabricating an elastomeric structure comprises microfabricating a first elastomeric layer, microfabricating a second elastomeric layer; positioning the second elastomeric layer on top of the first elastomeric layer; and bonding a bottom surface of the second elastomeric layer onto a top surface of the first elastomeric layer.

12. Alternative Device Fabrication Methods

FIGS. 1-7A and 8-18 above show embodiments of multilayer soft lithography and encapsulation methods, respectively, for fabricating elastomer structures in accordance with the present invention. However, these fabrication methods are merely exemplary, and variations on these techniques may be employed to create elastomer structures.

For example, FIGS. 3 and 4 show fabrication of an elastomer structure utilizing multilayer soft lithography techniques, wherein the recess-bearing face of the upper elastomer layer is placed on top of the non-recess-bearing face of the lower elastomer layer. However, the present invention is not limited to this configuration.

FIG. 50 shows elastomeric structure 5410 featuring an alternative orientation of elastomeric layers, wherein recess-bearing faces 5400 and 5402 of first and second elastomer layers 5404 and 5406 are respectively placed into contact to create a larger-sized channel 5408. Alternatively, FIG. 51 shows an orientation of elastomeric layers wherein non-recess bearing faces 5500 and 5502 are placed into contact, such that recesses are present on opposite sides of the structure. Such an elastomer structure 5512 could be sandwiched between substrates 5508 and 5510 to produce channels 5504 and 5506 that cross-over each other.

FIGS. 52A-52D show various views of steps for constructing a fluid channel bridging structure utilizing encapsulation methods. Specifically, FIG. 52A shows a cross-sectional view of the formation of lower elastomeric portion 5600 of bridging structure 5602. FIG. 52B shows a cross-sectional view of the formation of upper elastomeric portion 5604 of the bridging structure. FIG. 52C shows assembly of upper and lower elastomeric portions 5604 and 5600 to form bridging structure 5602, wherein fluid flowing in channel 5606 bridges over cross-channel 5608 through vias 5610 and 5612 and bridge portion 5614 as shown by the arrows. FIG. 52D shows a plan view of bridging structure 5602, with bridge portion 5614 of the upper elastomeric is shown in solid, and the features in the underlying lower elastomer layer are shown in outline. This structure requires the formation of vias in the lower layer, but allows multiple liquid streams to flow in a single layer and cross over one another without mixing.

13. Composite Structures

As discussed above in conjunction with the micromirror array structure of FIG. 38, the fabricated elastomeric structures of the present invention may be combined with non-elastomeric materials to create composite structures. Fabrication of such composite structures is now discussed in further detail.

FIG. 53A shows a cross-sectional view of one embodiment of a composite structure in accordance with the present invention. FIG. 53A shows composite valve structure 5700 including first, thin elastomer layer 5702 overlying semiconductor-type substrate 5704 having channel 5706 formed therein. Second, thicker elastomer layer 5708 overlies first elastomer layer 5702. Actuation of first elastomer layer 5702 to drive it into channel 5706, will cause composite structure 5700 to operate as a valve.

While FIG. 53A depicts the walls and floor of the flow channel formed in the substrate material, the invention is not limited to this particular configuration. Other features could also be defined in the substrate, including but not limited to wells or fluid-containing chambers.

FIG. 53B shows a cross-sectional view of a variation on the theme of FIG. 53A, wherein thin elastomer layer 5802 is sandwiched between two hard, semiconductor substrates 5804 and 5806, with lower substrate 5804 featuring channel 5808. Again, actuation of thin elastomer layer 5802 to drive it into channel 5808 will cause composite structure 5810 to operate as a valve.

The structures shown in FIGS. 53A-B may be fabricated utilizing either the multilayer soft lithography or encapsulation techniques described above. In the multilayer soft lithography method, the elastomer layer(s) would be formed and then placed over the semiconductor substrate bearing the channel or other feature. In the encapsulation method, the channel would be first formed in the semiconductor substrate, and then the channel would be filled with a sacrificial material such as photoresist. The elastomer would then be formed in place over the substrate, with removal of the sacrificial material producing the channel overlaid by the elastomer membrane. As is discussed in detail below in connection with bonding of elastomer to other types of materials, the encapsulation approach may result in a stronger seal between the elastomer membrane component and the underlying nonelastomer substrate component.

As shown in FIGS. 53A-B, a composite structure in accordance with embodiments of the present invention may include a hard substrate that bears a passive feature such as a channels or chambers. However, the present invention is not limited to this approach, and the underlying hard substrate may bear active features that interact with an elastomer component bearing a recess.

This is shown in FIG. 54, wherein composite structure 5900 includes elastomer component 5902 containing recess 5904 having walls 5906 and ceiling 5908. Ceiling 5908 forms flexible membrane portion 5909. Elastomer component 5902 is sealed against substantially planar nonelastomeric component 5910 that includes active device 5912. Active device 5912 may interact with material present in recess 5904 and/or flexible membrane portion 5909.

In the micromirror array embodiment previously described in conjunction with FIG. 38, the underlying substrate contained active structures in the form of an electrode array. However, many other types of active structures may be present in the nonelastomer substrate. Active structures that could be present in an underlying hard substrate include, but are not limited to, resistors, capacitors, photodiodes, transistors, chemical field effect transistors (chem FET's), amperometric/coulometric electrochemical sensors, fiber optics, fiber optic interconnects, light emitting diodes, laser diodes, vertical cavity surface emitting lasers (VCSEL's), micromirrors, accelerometers, pressure sensors, flow sensors, CMOS imaging arrays, CCD cameras, electronic logic, microprocessors, thermistors, Peltier coolers, waveguides, resistive heaters, chemical sensors, strain gauges, inductors, actuators (including electrostatic, magnetic, electromagnetic, bimetallic, piezoelectric, shape-memory-alloy based, and others), coils, magnets, electromagnets, magnetic sensors (such as those used in hard drives, superconducting quantum interference devices (SQUIDS) and other types), radio frequency sources and receivers, microwave frequency sources and receivers, sources and receivers for other regions of the electromagnetic spectrum, radioactive particle counters, and electrometers.

As is well known in the art, a vast variety of technologies can be utilized to fabricate active features in semiconductor and other types of hard substrates, including but not limited to printed circuit board (PCB) technology, CMOS, surface micromachining, bulk micromachining, printable polymer electronics, and TFT and other amorphous/polycrystalline techniques as are employed to fabricate laptop and flat screen displays.

A composite structure in accordance with one embodiment of the present invention comprises a nonelastomer substrate having a surface bearing a first recess, a flexible elastomer membrane overlying the non-elastomer substrate, the membrane able to be actuated into the first recess, and a layer overlying the flexible elastomer membrane.

An embodiment of a method of forming a composite structure comprises forming a recess in a first nonelastomer substrate, filling the recess with a sacrificial material, forming a thin coat of elastomer material over the nonelastomer substrate and the filled recess, curing the elastomer to form a thin membrane, and removing the sacrificial material.

A composite structure in accordance with an alternative embodiment of the present invention comprises an elastomer component defining a recess having walls and a ceiling, the ceiling of the recess forming a flexible membrane portion, and a substantially planar nonelastomer component sealed against the elastomer component, the nonelastomer component including an active device interacting with at least one of the membrane portion and a material present in the recess.

A method of fabricating a composite structure comprising forming a recess in an elastomer component, the recess including walls and a ceiling, the ceiling forming a flexible membrane portion, positioning a material within the recess, forming a substantially planar nonelastomer component including an active device, and sealing the elastomer component against the nonelastomer component, such that the active device may interact with at least one of the membrane portion and the material.

A variety of approaches can be employed to seal the elastomeric structure against the nonelastomeric substrate, ranging from the creation of a Van der Waals bond between the elastomeric and nonelastomeric components, to creation of covalent or ionic bonds between the elastomeric and nonelastomeric components of the composite structure. Example approaches to sealing the components together are discussed below, approximately in order of increasing strength.

A first approach is to rely upon the simple hermetic seal resulting from Van der Waals bonds formed when a substantially planar elastomer layer is placed into contact with a substantially planar layer of a harder, non-elastomer material. In one embodiment, bonding of RTV elastomer to a glass substrate created a composite structure capable of withstanding up to about 3-4 psi of pressure. This may be sufficient for many potential applications.

A second approach is to utilize a liquid layer to assist in bonding. One example of this involves bonding elastomer to a hard glass substrate, wherein a weakly acidic solution (5 µl HCl in $H_2O$, pH 2) was applied to a glass substrate. The elastomer component was then placed into contact with the glass substrate, and the composite structure baked at 37° C. to remove the water. This resulted in a bond between elastomer and non-elastomer able to withstand a pressure of about 20 psi. In this case, the acid may neutralize silanol groups present on the glass surface, permitting the elastomer and non-elastomer to enter into good Van der Waals contact with each other.

Exposure to ethanol can also cause device components to adhere together. In one embodiment, an RTV elastomer material and a glass substrate were washed with ethanol and then dried under Nitrogen. The RTV elastomer was then placed into contact with the glass and the combination baked for 3 hours at 80° C. Optionally, the RTV may also be exposed to a vacuum to remove any air bubbles trapped between the slide and the RTV. The strength of the adhesion between elastomer and glass using this method has withstood pressures in excess of 35 psi. The adhesion created using this method is not permanent, and the elastomer may be peeled off of the glass, washed, and resealed against the glass. This ethanol washing approach can also be employed used to cause successive layers of elastomer to bond together with sufficient strength to resist a pressure of 30 psi. In alternative embodiments, chemicals such as other alcohols or diols could be used to promote adhesion between layers.

An embodiment of a method of promoting adhesion between layers of a microfabricated structure in accordance with the present invention comprises exposing a surface of a first component layer to a chemical, exposing a surface of a second component layer to the chemical, and placing the surface of the first component layer into contact with the surface of the second elastomer layer.

A third approach is to create a covalent chemical bond between the elastomer component and functional groups introduced onto the surface of a nonelastomer component. Examples of derivitization of a nonelastomer substrate surface to produce such functional groups include exposing a glass substrate to agents such as vinyl silane or aminopropyltriethoxy silane (APTES), which may be useful to allow bonding of the glass to silicone elastomer and polyurethane elastomer materials, respectively.

A fourth approach is to create a covalent chemical bond between the elastomer component and a functional group native to the surface of the nonelastomer component. For example, RTV elastomer can be created with an excess of vinyl groups on its surface. These vinyl groups can be caused to react with corresponding functional groups present on the exterior of a hard substrate material, for example the Si—H bonds prevalent on the surface of a single crystal silicon substrate after removal of native oxide by etching. In this example, the strength of the bond created between the elastomer component and the nonelastomer component has been observed to exceed the materials strength of the elastomer components.

The discussion of composite structures has so far focused upon bonding an elastomer layer to an underlying non-elastomer substrate. However, this is not required by the present invention.

As previously described, a microfabricated elastomer structure may be sliced vertically, often preferably along a channel cross section. In accordance with embodiments of the present invention, a non-elastomer component may be inserted into the elastomer structure that has been opened by such a cut, with the elastomer structure then resealed. One example of such an approach is shown in FIGS. 57A-57C, which illustrates cross-sectional views of a process for forming a flow channel having a membrane positioned therein. Specifically, FIG. 57A shows a cross-section of a portion of device 6200 including elastomer membrane 6202 overlying flow channel 6204, and elastomer substrate 6206.

FIG. 57B shows the results of cutting device 6200 along vertical line 6208 extending along the length of flow channel 6204, such that halves 6200a and 6200b are formed. FIG. 57C shows insertion of permeable membrane element 6210 between halves 6200a and 6200b, followed by attachment of halves 6200a and 6200b to permeable membrane 6210. As a result of this configuration, the flow channel of the device actually comprises channel portions 6204a and 6204b separated by permeable membrane 6210.

The structure of FIG. 57C could be utilized in a variety of applications. For example, the membrane could be used to perform dialysis, altering the salt concentration of samples in the flow channel. The membrane of the structure of FIG. 57C could also be used to purify samples. Yet another potential application for the structure of FIG. 57C is to isolate the products of a reaction, for example to remove a product from an enzymatic reaction in order to avoid product inhibition. Depending upon the composition of the membrane, an organic solvent may be present on one side of the membrane while an aqueous buffer is present on the other side of the membrane. Yet another possible function of the membrane would be to bind particular chemical moieties such as proteins, peptides or DNA fragments for purification, catalysis or analysis.

An embodiment of a method of fabricating an elastomeric structure comprises cutting the first elastomer structure along a vertical section to form a first elastomer portion and a second elastomer portion; and bonding the first elastomer structure to another component.

14. Priming of Flow Channels

One potentially useful property of elastomeric structures is their permeability to gases. Specifically, elastomer materials may permit diffusion of certain gas species, while preventing diffusion of liquids. This characteristic may be very useful in manipulating small volumes of fluid.

For example, fluidic devices having complex channel architectures in general must address issues of priming the channels. As fluid is initially injected into a complicated channel structure, it follows the path of least resistance and may leave some regions of the structure unfilled. It is generally difficult or impossible to fill dead-end regions of the structure with liquid.

Accordingly, one approach of the present invention exploits gas permeability of certain elastomer materials to fill channel structures including dead end channels and chambers. In accordance with one embodiment of a method for priming a microfluidic structure, initially all but one of the channel entries into the structure are plugged. A neutral buffer is then injected into the remaining channel and maintained under pressure. The pressurized buffer fills the channels, compressing in front of it any gas present in the channel. Thus compressed, gas trapped in the channel is forced to diffuse out of the structure through the elastomer.

In this manner, a liquid sample may be introduced into the flow channels of a microfabricated device without producing unwanted pockets of gas. By injecting a liquid sample under pressure into the flow channels of a microfluidic device and then maintaining the injection pressure for a given time, the liquid sample fills the channel and any gas resulting pockets within the channel diffuse out of the elastomer material. According to this method, the entire microfluidic structure may rapidly be filled from a single via. Dead end chambers filled with liquid utilizing this method may be employed in storage, metering, and mixing applications.

The gas permeability of elastomer materials may result in the introduction of gases into flow channels where pneumatic (air-driven) actuation systems are employed. Such pneumatic valves may be operated at high control pressures in order to withstand high back pressures. Under such operating conditions, gas may diffuse across a relatively thin membrane, thereby introducing bubbles into the flow channel. Such unwanted diffusion of air through the membrane can be avoided by utilizing a control medium to which the elastomer is much less permeable, i.e. a gas which diffuses much more slowly through the elastomer or a liquid. As described above, control lines function well to transmit a control pressure when filled with water or oil, and do not introduce bubbles into the flow channels. Furthermore, using the priming method described above, it is possible to fill dead end control channels with fluid and hence no modification of an existing air-driven control structure would be required.

An embodiment of a method of filling a microfabricated elastomeric structure with fluid in accordance with the present invention comprises providing an elastomer block having a flow channel, the elastomer block comprising an elastomer material known to be permeable to a gas. The flow channel is filled with the gas, fluid is injected under pressure into the flow channel, and gas remaining in the flow channel is permitted to diffuse out of the elastomer material.

15. Metering by Volume Exclusion

Many high throughput screening and diagnostic applications call for accurate combination of and of different reagents in a reaction chamber. Given that it is frequently necessary to prime the channels of a microfluidic device in order to ensure fluid flow, it may be difficult to ensure mixed solutions do not become diluted or contaminated by the contents of the reaction chamber prior to sample introduction.

Volume exclusion is one technique enabling precise metering of the introduction of fluids into a reaction chamber. In this approach, a reaction chamber may be completely or partially emptied prior to sample injection. This method reduces contamination from residual contents of the chamber contents, and may be used to accurately meter the introduction of solutions in a reaction chamber.

Figure 58A:
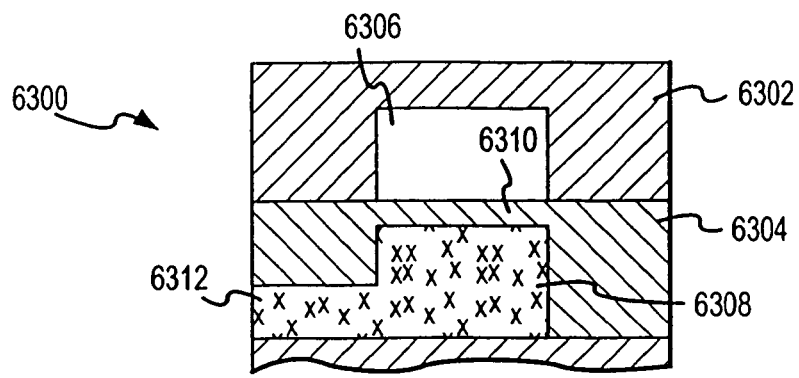

Specifically, FIGS. 58A-58D show cross-sectional views of a reaction chamber in which volume exclusion is employed to meter reactants. FIG. 58A shows a cross-sectional view of portion 6300 of a microfluidic device comprising first elastomer layer 6302 overlying second elastomer layer 6304. First elastomer layer 6302 includes control chamber 6306 in fluid communication with a control channel (not shown). Control chamber 6306 overlies and is separated from dead-end reaction chamber 6308 of second elastomer layer 6304 by membrane 6310. Second elastomer layer 6304 further comprises flow channel 6312 leading to dead-end reaction chamber 6308. As previously described, first reactant X may be introduced under pressure into dead-end reaction chamber 6308.

Figure 58B:
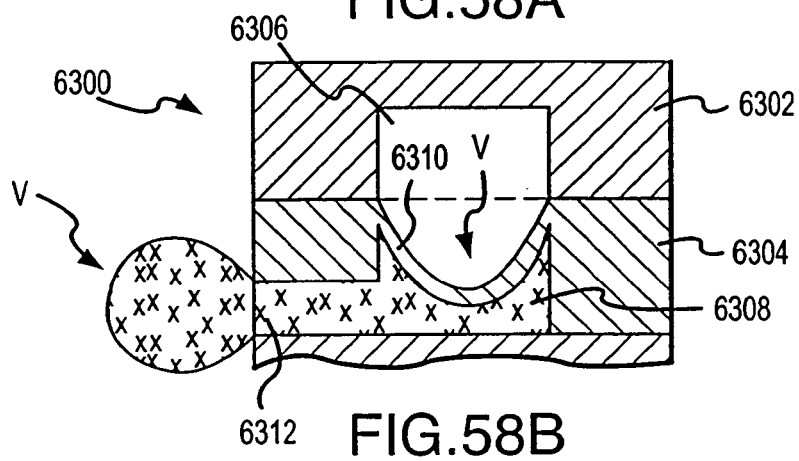

FIG. 58B shows the result of a pressure increase within control chamber 6306. Specifically, increased control chamber pressure causes membrane 6310 to flex downward into reaction chamber 6308, reducing by volume V the effective volume of reaction chamber 6308. This in turn excludes an equivalent volume V of reactant from reaction chamber 6308, such that volume V of first reactant X is output from flow channel 6312. The exact correlation between a pressure increase in control chamber 6306 and the volume of material output from flow channel 6312 can be precisely calibrated.

Figure 58C:
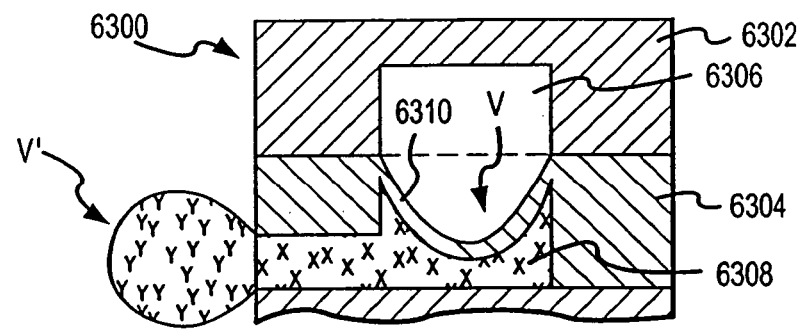

As shown in FIG. 58C, while elevated pressure is maintained within control chamber 6306, volume V' of second reactant Y is placed into contact with flow channel 6312 and reaction chamber 6308.

Figure 58D:
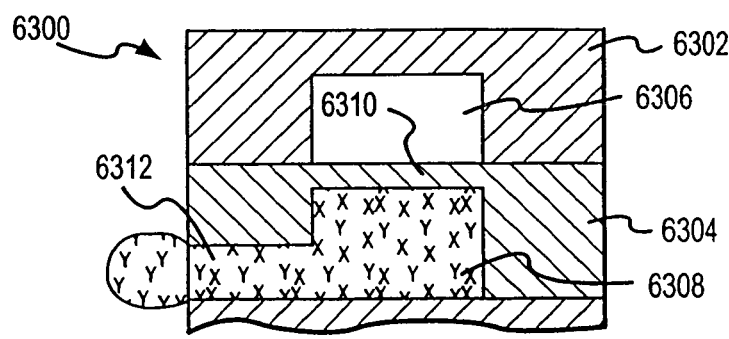

In the next step shown in FIG. 58D, pressure within control chamber 6306 is reduced to original levels. As a result, membrane 6310 relaxes and the effective volume of reaction chamber 6308 increases. Volume V of second reactant Y is sucked into the device. By varying the relative size of the reaction and control chambers, it is possible to accurately mix solutions at a specified relative concentration. It is worth noting that the amount of the second reactant Y that is sucked into the device is solely dependent upon the excluded volume V, and is independent of volume V' of Y made available at the opening of the flow channel.

While FIGS. 58A-58D show a simple embodiment of the present invention involving a single reaction chamber, in more complex embodiments parallel structures of hundreds or thousands of reaction chambers could be actuated by a pressure increase in a single control line.

Moreover, while the above description illustrates two reactants being combined at a relative concentration that fixed by the size of the control and reaction chambers, a volume exclusion technique could be employed to combine several reagents at variable concentrations in a single reaction chamber. One possible approach is to use several, separately addressable control chambers above each reaction chamber. An example of this architecture would be to have ten separate control lines instead of a single control chamber, allowing ten equivalent volumes to be pushed out or sucked in.

Another possible approach would utilize a single control chamber overlying the entire reaction chamber, with the effective volume of the reaction chamber modulated by varying the control chamber pressure. In this manner, analog control over the effective volume of the reaction chamber is possible. Analog volume control would in turn permit the combination of many solutions reactants at arbitrary relative concentrations.

An embodiment of a method of metering a volume of fluid in accordance with the present invention comprises providing a chamber having a volume in an elastomeric block separated from a control recess by an elastomeric membrane, and supplying a pressure to the control recess such that the membrane is deflected into the chamber and the volume is reduced by a calibrated amount, thereby excluding from the chamber the calibrated volume of fluid.

16. Protein Crystallization

As just described, embodiments of microfabricated elastomeric devices in accordance with the present invention permit extremely precise metering of fluids for mixing and reaction purposes. However, precise control over metering of fluid volumes can also be employed to promote crystallization of molecules such as proteins.

Protein recrystallization is an important technique utilized to identify the structure and function of proteins. Recrystallization is typically performed by dissolving the protein in an aqueous solution, and then deliberately adding a countersolvent to alter the polarity of the solution and thereby force the protein out of solution and into the solid phase. Forming a high quality protein crystal is generally difficult and sometimes impossible, requiring much trial and error with the identities and concentrations of both the solvents and the counter solvents employed.

Accordingly, FIG. 67 shows a plan view of protein crystallization system that allows mass recrystallization attempts. Protein crystallization system 7200 comprises control channel 7202 and flow channels 7204*a*, 7204*b*, 7204*c*, and 7204*d*. Each of flow channels 7204*a*, 7204*b*, 7204*c*, and 7204*d* feature dead-end chambers 7206 that serve as the site for recrystallization. Control channel 7202 features a network of control chambers 7205 of varying widths that overlie and are separated from chambers 7206 by membranes 7208 having the same widths as control chambers 7205. Although not shown to clarify the drawing, a second control featuring a second network of membranes may be utilized to create stop valves for selectively opening and closing the openings to dead-end chambers 7206. A full discussion of the function and role of such stop valves is provided below in conjunction with FIG. 70.

Operation of protein crystallization system 7200 is as follows. Initially, an aqueous solution containing the target protein is flushed through each of flow channels 7204a, 7204b, 7204c, and 7204d, filling each dead-end chamber 7206. Next, a high pressure is applied to control channel 7202 to deflect membranes 7208 into the underlying chambers 7206, excluding a given volume from chamber 7206 and flushing this excluded volume of the original protein solution out of chamber 7206.

Next, while pressure is maintained in control channel 7202, a different countersolvent is flowed into each flow channel 7204a, 7204b, 7204c, and 7204d. Pressure is then released in control line 7202, and membranes 7208 relax back into their original position, permitting the formerly excluded volume of countersolvent to enter chambers 7206 and mix with the original protein solution. Because of the differing widths of control chambers 7205 and underlying membranes 7208, a variety of volumes of the countersolvent enters into chambers 7206 during this process.

For example, chambers 7206a in the first two rows of system 7200 do not receive any countersolvent because no volume is excluded by an overlying membrane. Chambers 7106b in the second two rows of system 7200 receive a volume of countersolvent that is 1:5 with the original protein solution. Chambers 7206c in the third two rows of system 7200 receive a volume of countersolvent that is 1:3 with the original protein solution. Chambers 7206d in the fourth two rows of system 7200 receive a volume of countersolvent that is 1:2 with the original protein solution, and chambers 7206e in the fifth two rows of system 7200 receive a volume of countersolvent that is 4:5 with the original protein solution.

Once the countersolvent has been introduced into the chambers 7206, they may be resealed against the environment by again applying a high pressure to control line 7202 to deflect the membranes into the chambers. Resealing may be necessary given that recrystallization can require on the order of days or weeks to occur. Where visual inspection of a chamber reveals the presence of a high quality crystal, the crystal may be physically removed from the chamber of the disposable elastomer system.

While the above description has described a protein crystallization system that relies upon volume exclusion to meter varying amounts of countersolvent, the invention is not limited to this particular embodiment. Accordingly, FIG. 70 shows a plan view of protein crystallization system wherein metering of different volumes of countersolvent is determined by photolithography during formation of the flow channels.

Protein crystallization system 7500 comprises flow channels 7504a, 7504b, 7504c, and 7504d. Each of flow channels 7504a, 7504b, 7504c, and 7504d feature dead-end chambers 7506 that serve as the site for recrystallization.

System 7500 further comprises two sets of control channels. First set 7502 of control channels overlie the opening of chambers 7506 and define stop valves 7503 that, when actuated, block access to chambers 7506. Second control channels 7505 overlie flow channels 7504a-d and define segment valves 7507 that, when actuated, block flow between different segments 7514 of a flow channel 7404.

Operation of protein crystallization system 7500 is as follows. Initially, an aqueous solution containing the target protein is flushed through each of flow channels 7504a, 7504b, 7504c, and 7504d, filling dead-end chambers 7506.

Next, a high pressure is applied to control channel 7502 to actuate stop valves 7503, thereby preventing fluid from entering or exiting chambers 7506.

While maintaining stop valves 7503 closed, each flow channel 7504a-d is then filled with a different countersolvent. Next, second control line 7505 is pressurized, isolating flow channels 7504a-d into segments 7514 and trapping differing volumes of countersolvent. Specifically, as shown in FIG. 70 segments 7514 are of unequal volumes. During formation of protein crystallization structure 7500 by soft lithography, photolithographic techniques are employed to define flow channels 7504a-d having segments 7514 of different widths 7514a and lengths 7514b.

Thus, when pressure is released from first control line 7502 and stop valves 7503 open, a different volume of countersolvent from the various segments 7514 may diffuse into chambers 7506. In this manner, precise dimensions defined by photolithography can be employed to determine the volume of countersolvent trapped in the flow channel segments and then introduced to the protein solution. This volume of countersolvent in turn establishes the environment for crystallization of the protein.

A protein crystallization system in accordance with one embodiment of the present invention comprises an elastomeric block including a microfabricated chamber having a volume and receiving a protein solution, and a microfabricated flow channel in fluid communication with the chamber, the flow channel receiving a countersolvent and introducing a fixed volume of countersolvent to the chamber.

17. Pressure Amplifier

As discussed above, certain embodiments of microfabricated elastomer devices according to the present invention utilize pressures to control the flow of fluids. Accordingly, it may be useful to include within the device structures that enable the amplification of applied pressures in order to enhance these effects.

FIGS. 59A and 59B show cross-sectional and plan views respectively, of an embodiment of a linear amplifier constructed utilizing microfabrication techniques in accordance with the present invention. Pressure amplifier 6400 comprises first (control) elastomer layer 6402 overlying second (amplifying) elastomer layer 6404 that in turn overlies third (flow) elastomer layer 6406. Third elastomer layer 6406 in turn overlies substrate 6409.

Third elastomer layer 6406 encloses flow channel 6408 separated from overlying amplifying elastomer layer 6404 by membrane 6410. Pyramidal amplifying element 6412 includes lower surface 6414 in contact with membrane 6410 and upper surface 6416 in contact with first elastomer layer 6402. Area $A_1$ of upper surface 6416 of pyramidal amplifying element 6412 is larger than area $A_2$ of lower surface 6414.

As a result of application of a pressure $p_1$ in control channel 6415 of first elastomer layer 6402, a force $F_1$ is communicated to upper surface 6416 of pyramid structure 6412. Pyramid 6412 in turn transfers force $F_1$ to lower surface 6414 having a smaller area. Since the force is equal to pressure multiplied by area (F=pA), and since the force applied to the top of pyramid structure 6412 is equal to the force exerted by the base of pyramid structure 6412, $p_1 A_1 = p_2 A_2$. Since $A_1 > A_2$, membrane 6410 will experience an amplified pressure $p_2$, $p_2 > p_1$. The resulting amplifying factor can be estimated by simply comparing the two areas $A_1$ and $A_2$:

$$p_2/p_1 \sim A_1/A_2, \text{ where} \quad (2)$$

$p_2/p_1$=pressure amplifying factor.

Equation (2) is an approximation due to the elasticity of the amplifier structure itself, which will generally act to reduce the amplifying effect.

An example of a method for fabricating a pressure amplifier structure is now provided. A first, control elastomer layer featuring a control channel of width 200 λm and height 10 μm is fabricated utilizing 5A: 1B PDMS over a mold. A second, flow elastomer layer featuring a rounded flow channel of width 50 μm and height 10 μm is similarly fabricated by spinning 5A:1B PDMS on a mold at 4000 rpm for 60 sec, generating a membrane having a thickness of 15 μm.

The third, amplifying elastomer layer is formed by providing a 3" silicon wafer of lattice type <100> bearing an oxide layer of thickness 20,000 Å oxide layer (Silicon Quest International). A pattern of photoresist 5740 (Shipley Microelectronics) reflecting the dimension of the upper surface (in this case a square having sides 200 μm) of the pyramidal amplification structure is then formed. Using the patterned photoresist as a mask, oxide of the wafer exposed by the photoresist pattern is etched with HF.

Next, the patterned oxide layer is utilized as a mask for the removal of exposed underlying silicon to form a mold for the pyramidal amplifying structure. Specifically, exposed silicon on the wafer is wet etched at 80° C. with 30% KOH (w/v), resulting in formation of a trench having a walls inclined at an angle of 54.7°. The etch rate of silicon utilizing this chemistry is 1 μm/min, allowing precise control over the depth of the trench and hence the height of the amplifying structure molded and the resulting amplification factor. In this example, etching for 20 min resulting in a 20 μm deep etch was employed.

After etching of the silicon is completed, the photoresist is removed with acetone and the oxide layer is etched away with HF. Afterward, the silicon mold is treated with Trimethylchlorosilane (TMCS, Sigma) and 20A: 1B RTV is spun at 2000 rpm for 60 sec onto the silicon mold including the etched trench, and then baked for 60 min at 80° C. Next, the control layer is aligned over the amplifying layer. The two layers are baked together for an additional hour. The two layers are peeled of carefully from the (amplifier) mold and are aligned on the flow channel. After an additional one hour baking the complete device is removed from the mold.

FIG. 59C shows a photograph of the finally assembled device in the open state. FIG. 59D shows a photograph of the finally assembled device in the closed state in response to application of a pressure of 18 psi pressure to control channel 6415, resulting in an amplification factor of approximately 1.3.

An embodiment of a pressure amplifier in accordance with the present invention comprises an elastomeric block formed with first and second microfabricated recesses therein, and an amplifier structure having a first surface area in contact with the first recess and a second surface area in contact with the second recess. The first surface area is larger than the second surface area such that a pressure in the first recess is communicated by the amplifier structure as an amplified pressure to the second recess.

A method for amplifying a pressure in a flow channel of a microfabricated elastomer structure comprises providing an elastomer block including a first recess in contact with a first area of an amplifier structure and second recesses in contact with a second area of the amplifier structure, applying a pressure to the first area; and communicating the pressure to the second area, the second area smaller than the first area such that the pressure communicated to the second recess is amplified.

18. Check Valve

One potentially useful structure in conventional fluid handling devices is a check valve which permits the flow of fluid in only one direction through a conduit. FIGS. 61A and 61B show plan and cross-sectional views, respectively, of a microfabricated one-way valve structure in accordance with an embodiment of the present invention. Microfabricated structure 6600 includes flow channel 6602 formed in elastomer 6604. Left portion 6602a and right portion 6602b of flow channel 6602 are in fluid communication with each other through one-way valve 6606.

Specifically, microfluidic one-way valve 6606 permits fluid to flow in direction M→through flow channel 6602 and moveable flap 6608, but not in opposite direction ←N. Flap 6608 is integral with ceiling 6602c of flow channel 6602 and does not contact bottom 6602d or sides 6602e of flow channel 6602, thus allowing flap 6608 to swing freely. Flap 6608 is able to seal against left portion 6602a of flow channel 6602 because it is both larger in width and in height than the cross-section of the right channel portion. Alternatively, the walls of the right channel may feature protuberances that inhibit movement of the flap.

Valve 6606 operates passively, relying upon channel geometry and the properties of the elastomer rather than upon external forces. Specifically, as fluid flows from left to right in direction M→, flap 6608 is able to swing open into right hand side 6602b of flow channel. However, when the direction of fluid flow reverses to ←N, flap 6608 seals against the opening of left hand side 6602a of flow channel 6602.

Figure 62A:
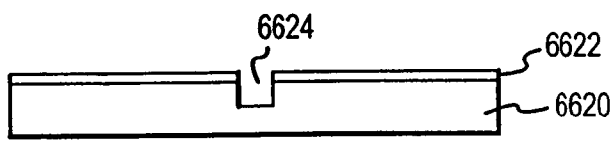
Figure 62B:
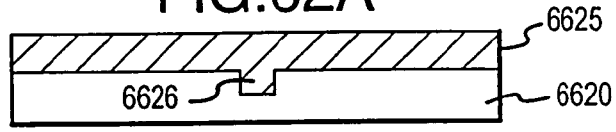
Figure 62C:
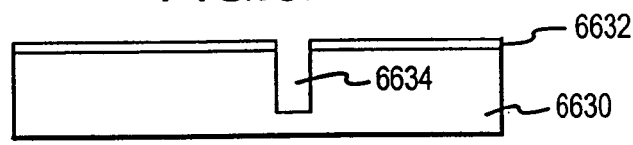
Figure 62D:
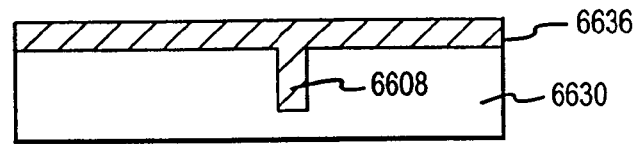
Figure 62E:
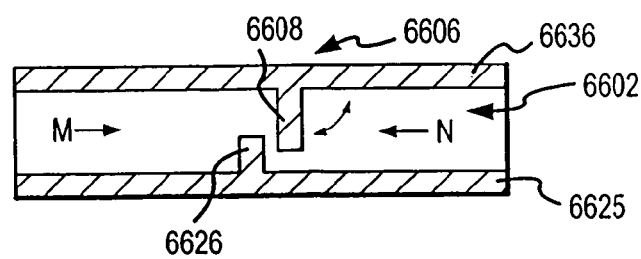

FIGS. 62A-62E show cross-sectional views of a process for fabricating a one way valve in accordance with the present invention. In FIG. 62A, first micomachined silicon mold 6620 is formed using first patterned photoresist layer 6622 defining first recess 6624 that will in turn define bottom-sealing portion 6626 of the flow channel. In FIG. 62B, elastomer is poured onto mold 6620 and solidified, such that removal of first molded piece 6625 produces elevated bottom-sealing portion 6626. In FIG. 62C, second micromachined silicon mold 6630 is formed using second patterned photoresist layer 6632 defining second recess 6634 that will in turn define the ceiling and the flap of the flow channel. In FIG. 62D, elastomer is poured onto second mold 6630 and cured, such that removal of second molded piece 6636 includes projecting flap 6608. In FIG. 62E, first molded piece 6625 and second molded piece 6636 are bonded together to produce intervening flow channel 6602 and one-way valve 6606.

A one-way valve in accordance with an embodiment of the present invention comprises a microfabricated channel formed in an elastomeric block, a flap integral with the elastomeric block projecting into the channel and blocking the channel, the flap deflectable to permit fluid to flow in only a first direction.

19. Fluidics

Fluidics refers to techniques which utilize flowing fluids as a signal bearing medium, and which exploit properties of fluid dynamics for modification (switching, amplification) of those signals. Fluidics is analogous to electronics, wherein a flow of electrons is used as the signal bearing medium and electromagnetic properties are utilized for signal switching and amplification.

Accordingly, another application of microfabricated structures of the present invention is in fluidics circuits. One embodiment of a fluidic logic device in accordance with the present invention comprises an elastomeric block, and a plurality of microfabricated channels formed in the elastomeric block, each channel containing a pressure or flow representing a signal, a change in the pressure or flow in a first channel resulting in a change in the pressure or fluid flow in a second channel consistent with a logic operation.

Fluidic logic structures in accordance with embodiments of the present invention offer the advantage of compact size. Another advantage of fluidic logic structures of the present invention is their potential use in radiation resistant applications. A further advantage of fluidic logic circuits is that, being non-electronic, such fluidic logic circuitry may not be probed by electro magnetic sensors, thus offering a security benefit.

Yet another advantage of fluidic logic circuits is that they can be readily integrated into microfluidic systems, enabling "onboard" control and reducing or eliminating the need for an external control means. For instance, fluidic logic could be used to control the speed of a peristaltic pump based on the downstream pressure, thus allowing direct pressure regulation without external means. Similar control using an external means would be much more complicated and difficult to implement, requiring a separate pressure sensor, transduction of the pressure signal into an electrical signal, software to control the pump rate, and external hardware to transduce the control signal into pneumatic control.

One fundamental logic structure is a NOR gate. The truth table for a NOR logic structure is given below in TABLE 2:

TABLE 2

NOR Gate Truth Table

| INPUT 1 | INPUT 2 | OUTPUT |
|---------|---------|--------|
| high    | high    | low    |
| high    | low     | low    |
| low     | high    | low    |
| low     | low     | high   |

One simple embodiment of a NOR gate structure fabricated in accordance with the present invention comprises a flow channel including an inlet portion and an outlet portion, at least two control channels adjacent to the flow channel and separated from the first channel by respective first and second elastomer membranes, such that application of pressures to the control channels deflects at least one of the first and second membranes into the flow channel to reflect a pressure at the outlet consistent with a NOR-type truth table.

FIG. 63 shows a plan view of an alternative embodiment of a NOR logic structure in accordance with the present invention that is fabricated from pressure amplifier structures. NOR gate 6900 comprises input flow channels 6902 and 6904 that contain a pressurized flow of fluid. Control channels 6906 and 6908 are orthogonal to and overlie flow channels 6902 and 6904, forming valves 6910a, 6910b, 6910c, and 6910d. After passing underneath control channels 6906 and 6908, flow channels 6902 and 6904 merge to form a single output flow channel 6912. NOR gate 6900 operates as follows.

Where an input pressure signal to each of control lines 6906 and 6908 is low, valves 6910a-d are open and fluid flows freely through flow channels 6902 and 6904, resulting in a high combined pressure at output flow channel 6912. Where a pressure higher than that present in flow channels 6902 and 6904 is introduced into first control line 6906, valves 6910a and 6910b both close, resulting in a low pressure at output flow channel 6912. Similarly, where a pressure higher than that present in flow channels 6902 and 6904 is introduced into second control line 6908, one way valves 6910c and 6910d close, and the output at output flow channel 6912 is also low. Of course, application of high pressures in both control lines 6906 and 6908 still results in a low pressure at output 6912.

NOR gate 6900 can be linked with other logic devices to form more complex logic structures. For example, FIG. 63 shows the output of first NOR gate 6900 serves as one of the inputs (control lines) for second NOR gate 6950, which is likely formed in an elastomer layer underlying first NOR gate 6900. It may be necessary to amplify the pressure output from first NOR gate 6900 in order to achieve the necessary control.

Moreover, signal amplification in accordance with embodiments of the present invention can be utilized to maintain control pressure signals and information-carrying (flow) pressures at approximately the same magnitude, Such approximately parity between information and control signals is one hallmark of conventional digital electronics control systems Absent the use of amplified control pressures, fluidics applications in accordance with embodiments of the present invention would generally require control pressures larger than the flow pressures, in order to control the flows of fluids through the device. However, using pressure amplification in accordance with embodiments of the present invention, pressures in the control and flow channels of a fluidics circuit can be of approximately the same order of magnitude.

Another basic building block of logic structures such as AND and OR gates is the diode. Accordingly, FIG. 64 shows a plan view of one embodiment of an AND gate structure fabricated utilizing fluidic check valves in accordance with the present invention as diodes. The truth table for an AND logic structure is given below in TABLE 3:

TABLE 3

AND Gate Truth Table

| INPUT 1 | INPUT 2 | OUTPUT |
|---------|---------|--------|
| high    | high    | high   |
| high    | low     | low    |
| low     | high    | low    |
| low     | low     | low    |

Operation in accordance with this truth table is possible utilizing structure 7000 of FIG. 64. Specifically, AND gate structure 7000 includes inlet portion 7002a flow channel 7002 in fluid communication with outlet portion of flow channel 7002b through flow resistor 7004. First and second control channels 7006 and 7008 are in communication with flow channel 7002 at junction 7002c immediately upstream of flow resistor 7004 through first one way valve 7010 and second one way valve 7012 respectively.

Only where first control channel 7006 and second control channel 7008 are pressurized (each corresponding to a high logic state) will a high pressure flow emerge from flow channel output portion 7002b. Where the pressure in first control channel 7006 is low, the pressure in second control channel 7008 is low, or the pressures in both first and second control channels 7006 and 7008 are low, fluid entering device 7000 through inlet 7002a will encounter back pressure from flow resistor 7004 at junction 7002c, and in response flow out through one or both of one way valves 7010 and 7012 and respective control channels 7006 and 7008. More complex logic structures can be created by connecting an AND gate with other logic structures in various combinations.

An embodiment of a microfluidic structure in accordance with the present invention comprises an underlying substrate and a first elastomer layer overlying the substrate, the first elastomer layer bearing in a bottom surface a first recess. A second elastomer layer overlies the first elastomer layer, the second elastomer layer bearing in a bottom surface a second recess having an arched ceiling. A membrane portion of the first elastomer layer is defined between the first recess and the second recess, the membrane portion deflectable upward into the second recess to conform with and seal against the arched ceiling.

An embodiment of a microfluidic structure in accordance with the present invention comprises an underlying substrate and a first elastomer layer overlying the substrate, the first elastomer layer bearing a first recess in its bottom surface. A second elastomer layer overlies the first elastomer layer, the second elastomer bearing a second recess in its bottom surface. A third elastomer layer overlies the second elastomer layer, the third elastomer layer bearing a third recess in its bottom surface such that a first deflectable membrane is defined from a portion of the first elastomer layer between the first recess and the second recess, and a second deflectable membrane is defined from a portion of the second elastomer layer between the second recess and the third recess.

An embodiment of a method of fabricating an microfabricated elastomeric device in accordance with the present invention comprises forming an nonelastomeric mold having a plurality of features of differing heights, and providing uncured elastomer material over the nonelastomeric mold. The elastomer material is cured and removed from the mold, such that the cured elastomer material exhibits recesses of different depths corresponding to the heights of the mold features. The cured elastomer material is placed onto a substrate to define a channel between the recess and the substrate, and a molded elastomer layer is placed over the cured elastomer material.

An embodiment of a microfluidic structure in accordance with the present invention comprises an underlying substrate, and a first elastomer layer overlying the substrate, the first elastomer layer bearing a flow channel in its bottom surface. A second elastomer layer overlies the first elastomer layer, the second elastomer bearing a serpentine control channel in a bottom surface. The serpentine channel overlaps the flow channel in at least three locations to define at least three deflectable membranes between the flow channel and the control channel, such that application of a high pressure signal to the control channel causes deflection of the membranes downward into the flow channel in a sequence to cause a flow of material present within the flow channel.

An alternative embodiment of a microfluidic structure in accordance with the present invention comprises an underlying substrate and a first elastomer layer overlying the substrate, the first elastomer layer bearing a serpentine control channel in a bottom surface. A second elastomer layer overlies the first elastomer layer, the second elastomer layer bearing a flow channel in a bottom surface. The flow channel overlaps the serpentine control channel in at least three locations to define at least three deflectable membranes between the control channel and the flow channel, such that application of a high pressure signal to the control channel causes deflection of the membranes upward into the flow channel in a sequence to cause a flow of material present within the flow channel.

An embodiment of a method of causing a flow of material through a microfluidic structure comprises disposing a flow channel in a first elastomer layer. A serpentine control channel is disposed in a second elastomer layer adjacent to the first elastomer layer, the control channel overlapping the flow channel in at least three locations to define first, second, and third deflectable membranes between the flow channel and the serpentine control channel. A high pressure signal is applied to the flow channel to cause the first, second, and third membranes to deflect into the flow channel in a peristaltic pumping sequence.

An embodiment of a method of forming a via in a microfabricated elastomer structure in accordance with the present invention comprises placing an elastomer material in contact with a mold comprising raised features, and curing the elastomer material. The cured elastomer material is removed from the mold. The cured elastomer material is punctured with a rigid hollow member, and the rigid hollow member is removed from the cured elastomer material to reveal a first via opening in fluid communication with the first recess.

An embodiment of a microfluidic structure in accordance with the present invention comprises an underlying substrate and a first elastomer layer overlying the substrate, the first elastomer layer bearing in a bottom surface a first recess, the first recess patterned in a plurality of channels splitting into a plurality of parallel branches, the parallel branches reuniting. A second elastomer layer overlies the first elastomer layer, the second elastomer layer bearing in a bottom surface a second recess, the second recess patterned in a plurality of parallel channels oriented orthogonal to the parallel branches. Membrane portions of the first elastomer layer are defined between a widened portion of the parallel channels and the underlying parallel branches, the membrane portions deflectable into the parallel branches to control a flow of fluid through the parallel branches.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention.

For example, other researchers have proposed alternative approaches to the microfabrication of microfluidic devices employing elastomer materials. U.S. Pat. Nos. 5,705,018 and 6,007,309 to Hartley, generally describe a microfluidic structure having flow channels microfabricated within a nonelastomeric substrate. An elastomer membrane overlying the flow channel is electrostatically actuated to deflect into the flow channel to cause a flow of fluid therethrough.

U.S. Pat. No. 5,376,252 to Ekstrom, generally describes a microfluidic structure featuring base layer alternating with patterned, elastomeric spacing layers. Duffy et al., "rapid Prototyping of Microfluidic Systems in Poly(dimethylsiloxane)", *Analytical Chemistry* 70(23):4974-4984 (1998), propose a microfluidic system utilizing a molded nonelastomer layer as a master for rapid prototyping of elastomer layers having channels and reservoirs.

In "A Pneumatically Actuated Micro Valve with a Silicon Rubber Membrane for Integration with Fluid-Handling Systems," *Proceedings of Transducers '95, the 8th International Conference on Solid-State Sensors and Actuators, and Eurosensors IX* (Sweden, June 1995) vol. 2, pp. 284-286, Vieider et al. describe a microfluidic pump structure comprising an moveable elastomeric portion supporting a silicon plunger structure able to be pneumatically driven to close a flow channel. In "A Microvalve System Fabricated by Thermoplastic Molding," *Journal of Micromechanics and Microengineering*, vol. 5, no. 2, June 1995, pp. 169-171, Fahrenberg et al. describe the thermonpneumatic actuation of a valve comprising a polyimide membrane.

In "A MEMS Thermopneumatic Silicone Membrane Valve," *Proceedings of the IEEE* 10*th Annual Workshop of Micro Electro Mechanical Systems* (Japan, January 1997) pp. 114-118, Yang et al. describe fabrication of a microfluidic valve structure by curing a silicone membrane cured against a nonelastomer (Si/SiN) bridge that was subsequently removed by etching. In "Smallest Dead Volume Microvalves for Integrated Chemical Analyzing Systems," *Proceedings of Transducers* '91, *the* 1991 *International Conference on Solid-State Sensors and Actuators*, (San Francisco, June 1991) pp. 1052-1055, Shoji et al. describe a microfluidic valve structure having a membrane of polymerized negative photoresist material that is actuated piezoelectrically.

In "A Titanium-Nickel Shape-Memory Alloy Actuated Micropump," *Proceedings of Transducers* '97, *the* 1997 *International conference on Solid-State Sensors and Actuators* (Chicago, 1997), vol. 1, pp. 361-364, Benard et al. describe use of polyimide check valves in conjunction with a microfabricated valve structure utilizing actuation of a nonelastomer membrane. In "Simulation Studies of Diffuser and Nozzle Elements for Valve-less Micropumps," *Proceedings of Transducers* '97, *the* 1997 *International Conference on Solid-State Sensors and Actuators* (Chicago, June 1997) vol. 2, pp. 1039-1042, Olsson et al. describe use of silicon molds to form electroplated nickel molds, that were in turn utilized to fabricate an injection molded plastic pump and valve structures.

In addition, much prior effort has gone into exploring microfluidic structures employing moveable components composed of nonelastomer material, such as thin layers of micromachined silicon. One example of this approach is the normally-closed valve structure described by Jerman, "Electrically-Activated, Normally-Closed Diaphragm Valve", *Proceedings of Transducers* '91 *in the* 1991 *International Conference on Solid State Sensors and Actuators* (San Francisco, June 1991) pp. 1045-1048. The structure of Jerman comprises a thick nonelastomer membrane linked to surrounding material by a thinner $SiO_2$ hinge that allows deflection of the membrane.

Accordingly, the various microfluidic structures, methods, applications, and architectural approaches described herein are generally applicable to all types of microfluidic handling devices, and are not limited to use with the multilayer elastomeric structures detailed herein.

It is intended that the invention not be limited to the particular embodiment disclosed as the best mode contemplated for carrying out this invention, but that the invention will include all embodiments and equivalents falling within the scope of the claims.

The following pending patent applications contain subject matter related to the instant application and are hereby incorporated by reference: U.S. nonprovisional patent application Ser. No. 09/970,122, entitled "Apparatus and Methods for Conducting Cell Assays and High Throughput Screening", filed Oct. 2, 2001; and U.S. nonprovisional patent application Ser. No. 09/724,548, entitled "Integrated Active Flux Microfluidic Devices and Methods", filed Nov. 28, 2000.

What is claimed is:

1. A method of forming a via in a microfabricated elastomer structure comprising:
   placing an elastomer material in contact with a mold comprising raised features;
   curing the elastomer material;
   removing the cured elastomer material from the mold
   puncturing the cured elastomer material with a rigid hollow member; and
   removing the rigid hollow member from the cured elastomer material to reveal a first via opening in fluid communication with the first recess.

2. The method of claim 1 wherein the cured elastomer material is punctured by the rigid hollow member at a recess corresponding to a location of the raised mold feature, thereby ensuring alignment of the via with the recess.

3. The method of claim 1 further comprising:
   placing the cured, punctured elastomer material onto a top surface of a second cured elastomer material bearing a second recess corresponding to a location of raised features of a second mold structure; and
   puncturing the second cured elastomer material and the first cured elastomer material at the second recess; and
   removing the rigid hollow member to reveal a second via in fluid communication with the second recess.

4. The method of claim 3 further comprising:
   placing the cured and punctured elastomer layers onto a top surface of an additional cured elastomer layer bearing a further recess corresponding to a location of raised features of a further mold structure; and
   puncturing the additional cured elastomer layer and the cured and punctured elastomer layers at the further recess; and
   removing the rigid hollow member to reveal an additional via in fluid communication with the further recess.

* * * * *

UNITED STATES PATENT AND TRADEMARK OFFICE
CERTIFICATE OF CORRECTION

PATENT NO. : 7,250,128 B2 Page 1 of 1
APPLICATION NO. : 11/111264
DATED : July 31, 2007
INVENTOR(S) : Unger et al.

It is certified that error appears in the above-identified patent and that said Letters Patent is hereby corrected as shown below:

Column 1, lines 32-35, delete "Work described herein has been supported, in part, by National Institute of Health grant HG-01642-02. The United States Government may therefore have certain rights in the invention.", and insert --This invention was made with government support under grant no. HG-01642-02 awarded by the National Institute of Health. The government has certain rights in the invention.--.

Signed and Sealed this

Twenty-ninth Day of July, 2008

JON W. DUDAS
*Director of the United States Patent and Trademark Office*